US010842808B2

(12) United States Patent
Remaud-Simeon et al.

(10) Patent No.: US 10,842,808 B2
(45) Date of Patent: Nov. 24, 2020

(54) POLYPEPTIDE HAVING THE CAPACITY TO FORM ALPHA-1,3 GLUCOSYL UNIT BRANCHINGS ON AN ACCEPTOR

(71) Applicants: INSTITUT NATIONAL DE LA RECHERCHE AGRONOMIQUE (INRA), Paris (FR); INSTITUT NATIONAL DES SCIENCES APPLIQUEES DE TOULOUSE, Toulouse (FR); CENTRE NATIONAL DE LA RECHERCHE SCIENTIFIQUE (CNRS), Paris (FR)

(72) Inventors: Magali Remaud-Simeon, Ramonville (FR); Marlene Vuillemin, Toulouse (FR); Claire Moulis, Vieillevigne (FR); Pierre Monsan, Mondonville (FR); Sandrine Morel, Auzeville-Tolosane (FR)

(73) Assignees: INSTITUT NATIONAL DE RECHERCHE POUR L'AGRICULTURE, L'ALIMENTATION ET L'ENVIRONNEMENT, Paris (FR); INSTITUT NATIONAL DES SCIENCES APPLIQUEES DE TOULOUSE, Toulouse (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 14 days.

(21) Appl. No.: 15/712,173

(22) Filed: Sep. 22, 2017

(65) Prior Publication Data
US 2018/0104274 A1  Apr. 19, 2018

Related U.S. Application Data

(62) Division of application No. 14/898,991, filed as application No. PCT/EP2014/001644 on Jun. 17, 2014, now abandoned.

(30) Foreign Application Priority Data

Jun. 17, 2013  (FR) ..................................... 13 01402

(51) Int. Cl.
| | |
|---|---|
| A61K 38/00 | (2006.01) |
| A61K 31/715 | (2006.01) |
| C12P 19/04 | (2006.01) |
| C12P 19/10 | (2006.01) |
| C12P 19/18 | (2006.01) |
| C08B 37/02 | (2006.01) |
| C12P 19/08 | (2006.01) |
| C12N 9/10 | (2006.01) |
| C08L 5/02 | (2006.01) |

(52) U.S. Cl.
CPC ........ *A61K 31/715* (2013.01); *C08B 37/0021* (2013.01); *C08L 5/02* (2013.01); *C12N 9/1051* (2013.01); *C12P 19/04* (2013.01); *C12P 19/08* (2013.01); *C12P 19/10* (2013.01); *C12P 19/18* (2013.01); *C12Y 204/01005* (2013.01); *C12Y 204/01* (2013.01)

(58) Field of Classification Search
None
See application file for complete search history.

(56) References Cited

PUBLICATIONS

Brison et al., "Synthesis of dextrants with controlled amounts of alpha-1,2 linkages using the transglucosidase GBD-CD2," Appl Microbio Biotechnol (2010) 86:545-554.
Cantarel et al., "The Carbohydrate-Active EnZymes database (CAZy): an expert resource for Glycogenomics," Nucleic Acids Research, 2009, vol. 37, D233-D238.
Chung et al., "Glucooligosaccharides from Leuconostoc mesenteroides B-742 (ATCC 13146): A potential prebiotic," Journal of Industrial Microbiology & Biotechnology, (2002), 29, 196-199.
Chung et al., "Efficacy of Leuconostoc mesenteroides (ATCC 13146) Isomaltooligosaccharides as a Poultry Prebiotic," 2004 Poultry Science Association, Inc, pp. 1302-1306.
Cote et al., "The formation of α-d-(1→3) branch linkages by an exocellular glucansucrase from Leuconostoc mesenteroides NRRL B-742*," Carbohydrate Research, 119(1982), 141-156.
Daude et al.,"Sucrose analogs: an attractive (bio)source for glycodiversification," Nat. Prod. Rep., 2012, 29, 945-960.
Hosang et al., "Cloning and Sequencing of the alphal->6 Dextransucrase Gene from Leuconostoc mensenteoides B-742CB," . Microbio. Biotechnol. (2000), 10(4), 559-563.
Irague et al., "Structure and Property Engineering of α-d-Glucans Synthesized by Dextransucrase Mutants," Biomacromolecules, 2012, 13, 187-195.
Jeanes et al., "Characterization and Classification of Dextrans from Ninety-six Strains of Bacteria," Oct. 20, 1954, pp. 5041-5052.
Kang et al., "Directed evolution of a dextransucrase for increased constitutive activity and the synthesis of a highly branched dextran," Journal of Molecular Catalysis B: Enzymatic 26 (2003) 167-176.

(Continued)

*Primary Examiner* — Thomas S Heard
(74) *Attorney, Agent, or Firm* — Nixon & Vanderhye

(57) ABSTRACT

Polypeptides having the ability to specifically form connections of glucosyl units in alpha 1,3 on an acceptor having at least one hydroxyl moiety are presented. The polypeptides include i) the pattern I of sequence SEQ ID NO: 1, ii) the pattern II of sequence SEQ ID NO: 2, iii) the pattern III of sequence SEQ ID NO: 3, and iv) the pattern IV of sequence SEQ ID NO: 4, or derivates from one or several of said patterns, wherein the polypeptide furthermore has an aspartic residue (D) at position 5 of the pattern II (SEQ ID NO: 2), a glutamic acid residue (E) at position 6 of the pattern III (SEQ ID NO: 3) and an aspartic acid residue (D) at position 6 of the pattern IV (SEQ ID NO: 4). Methods for producing acceptors connected to glucosyl units in alpha 1,3 using the polypeptides are also provided.

3 Claims, 8 Drawing Sheets

Specification includes a Sequence Listing.

(56) References Cited

PUBLICATIONS

Kang et al., "Bioengineering of Leuconostoc mesenteroides Glucansucrases That Gives Selected Bond Formation for Glucan Synthesis and/or Acceptor-Product Synthesis," J. Agric. Food Chem., 2011, 59, 4148-4155.

Leemhuis et al., "Glucansucrases: Three-dimensional structures, reactions, mechanism, alpha-glucan analysis and their implications in biotechnology and food applications," Journal of Biotechnology 163 (2013) 250-272.

Moulis et al., "Understanding the Polymerization Mechanism of Glycoside-Hydrolase Family 70 Glucansucrases," The Journal of Biological Chemistry, vol. 281, No. 42, pp. 31254-31267, Oct. 20, 2006.

Remaud et al., Charaterization of aplha-(1->3) Branched Oligosaccharides Synthesized by Acceptor Reaction with the Extracellular Glucosyltransferases from L. Mesenteroides NRRL B-742, J. Carbohydrate Chemistry, 11(3) 359-378 (1992).

Seymour et al., "Structural Analysis of Leuconostoc Dextrans Containing 3-O-α-d-Glucosylated α-d-Glucosyl Residues in both linear-chain and branch-point positions, or only in branch-poibnt positions, by methylation and by 13C-N.M.R. Spectroscopy," Carbohydrate Research 74 (1979), 41-62).

Sumner et al., "A Method for Determination of Saacharase Activity," pp. 51-54, Oct. 6, 1934, Department of Physiology and Biochemistry, Cornell University.

POLYPEPTIDE HAVING THE CAPACITY TO FORM ALPHA-1,3 GLUCOSYL UNIT BRANCHINGS ON AN ACCEPTOR

The present international application claims priority of application FR 13/01402 filed on 17 Jun. 2013, which is incorporated herein by reference.

FIELD OF THE INVENTION

The present invention relates to an isolated polypeptide having the ability to form connections of glucosyl units in alpha 1,3 on an acceptor, a polynucleotide encoding said polypeptide, its use in a production process of acceptors connected to glucosyl units in alpha 1,3, said acceptors connected to glucosyl units in alpha 1,3 and the use thereof.

BACKGROUND OF THE INVENTION

Glucosyltransferases are enzymes capable of catalysing the synthesis of glucose polymers from an inexpensive substrate, such as sucrose, alone or in the presence of an acceptor of glucosyl units comprising at least one hydroxyl moiety. Within these acceptor molecules, the glucosyl units are coupled by glycosidic linkages of variable nature ($\alpha$-1,6, $\alpha$-1,4, $\alpha$-1,2 or $\alpha$-1,3).

The transglucosylases (or glucan saccharases) belonging to the family 70 of glycoside hydrolases (database: *Carbohydrate Active Enzymes database* and CANTAREL et al, *Nucleic Acids Res., Vol.* 37, p: D233-238 2009) are enzymes naturally produced by lactic acid bacteria of the genera *Leuconostoc, Lactobacillus, Streptococcus* or *Weissela*. Starting from their substrate, in particular sucrose, a renewable and cheap substrate, these enzymes catalyse the synthesis of homopolymers of glucosyl units (glucans) generally of very high molecular weight and having various structures ($\alpha$-1,6/$\alpha$-1,4/$\alpha$-1,2 and/or $\alpha$-1,3) glycosidic bonds. Also, if hydroxylated molecules are added to the reaction medium on top of the donor of glucosyl units, these enzymes may also include these molecules at the detriment of the synthesis of polymer, resulting in a wide range of oligosaccharides and/or gluco-conjugates.

From the work described in JEANES et al. (1954), describing the purification and the characterisation of glucans produced by 96 strains of *Leuconostoc* sp., those produced by the strain *Leuconostoc mesenteroides* NRRL B-742 are known (also found in *L. mesenteroides* ATCC 13146, and since reclassified in *L. citreum* NRRL B-742). In effect, it produces two types of glucans: the fraction S and the fraction L.

The first glucan is composed of 50% of $\alpha$-1,6 bonds in its main chain and 50% in of connections in $\alpha$-1,3 (fraction S). Successive studies of the latter glucan described in JEANES & SEYMOUR (*Carbonate Research,* vol. 74, p: 31-40), COTE & ROBYT (*Carbohydrate Research,* vol. 119, p: 141-156, 1983) and REMAUD et al (*J. Carbohydrate Chemistry,* vol. 11 (3), 1992) showed that the latter had an original comb-like structure. More specifically, each glucosyl unit of the straight chain in this structure was branched in $\alpha$-1,3 by a single glucosyl unit.

The second glucan (fraction L) produced by the same strain was composed of 73% of $\alpha$-1,6 bonds and 14% of $\alpha$-1,4 bonds at branching points (SEYMOUR et al., *Carbohydrate Research, vol.* 74, p: 41-62, 1979).

These various studies have shown that the strain *L. citreum* NRRL B-742 has several coding genes for transglucosylases responsible for the synthesis of glucans; which have different specificities. In the presence of extracts of this strain, it was thus possible to produce gluco-oligosaccharides which proved to have strong prebiotic properties stimulating the growth of *Bifidobacterium* sp. and of *Lactobacillus* sp. eg (CHUNG & DAY, *Journal of Industrial Microbiology & Biotechnology,* vol. 29, p: 196-199, 2002; CHUNG & DAY, *Poultry Science,* vol. 83, p: 1302-1306, 2004; brevet U.S. Pat. No. 7,772,212).

Now, although this strain has been known for more than fifty years, the enzymes responsible for the synthesis of these glucans are still not known. It must indeed be understood that if some of these enzymes are extracellular; others, however, remain strongly associated with the cells, including the enzyme responsible for the glucans with a high content of $\alpha$-1,3 bonds (REMAUD et al., 1992). This strong association to the bacterial cells ensures that its purification and detailed characterisation could not be performed.

In 2000, Kim et al. described the cloning in *E. coli* of a transglucosylase resulting from this strain, called DsrB-742. The characterisation of the gene in question showed that it had 95% similarity with that of the already characterised DSR-B in *L. citreum* NRRL B-1299 and had a polymerisation activity of the glucosyl units in $\alpha$-1,6, but no specific connection activity in $\alpha$-1,3.

Finally, the identification and the biochemical characterisation of the enzyme responsible for the synthesis of comb-like glucans (S) compounds of 50% of connections in $\alpha$-1,3 therefore had remained totally unsuccessful so far.

SUMMARY OF THE INVENTION

Figure 1:
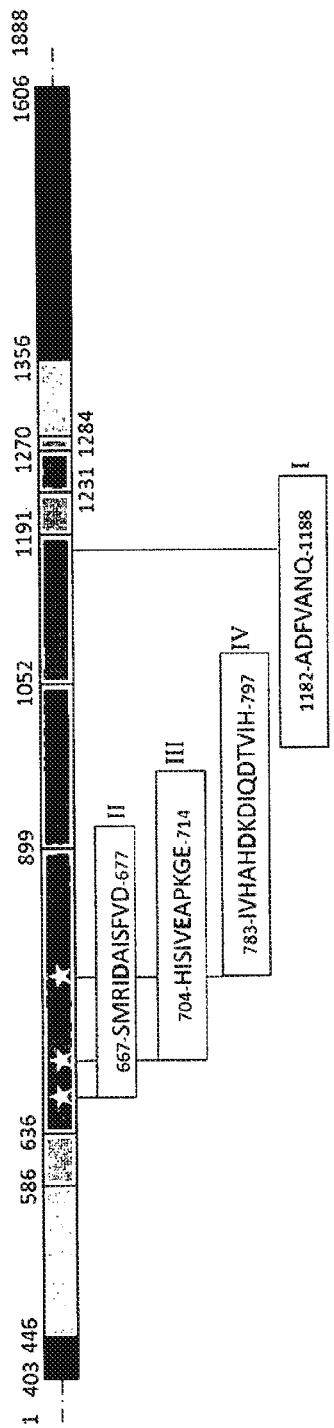
FIG. 1 shows the primary structure of the reference protein $\alpha$-1,3 BrS resulting from the strain *L. citreum* NRRL B-742.

The inventors have now demonstrated that the synthesis of comb-like dextrans by the strain *L. citreum* NRRL B-742 was due to the action, not of one but of two separate transglucosylases: one responsible for the synthesis of a linear dextran, and the other responsible for connections in $\alpha$-1,3 on these linear chains that act as acceptor molecules. The inventors have therefore identified a polypeptide having an enzymatic activity which had never been described before, responsible for specific connections of glucosyl units in $\alpha$-1,3 on acceptor molecules, e.g. such as dextrans. Note further that the inventors were able to control the connection rate of these glycosyl units. Finally, the inventors were able to identify two orthologues of this protein sequences in two other strains of *Leuconostoc*.

So this is the first natural branching enzyme described for a transglucosylase which, by sequence analysis, ranks in the family GH-70. Furthermore, the synthesis of polysaccharides connected with controlled rates of glucosyl units linked in alpha-1,3 has never been described, and no such connected product existed hitherto on the market.

This type of bonds in alpha-1,3 confers resistance to the action of degradative enzymes such as glycoside hydrolases such as dextranases, glucoamylases, amylases and particularly the digestive enzymes of the human tract thus increasing the lifetime of the acceptor molecule to which they are associated, and conveying to the gluco-oligosaccharides new physicochemical and/or prebiotic properties, which prove interesting in terms of industrial applications.

Prebiotics are non-digestible food ingredients that arrive intact in the colon where they are then specifically metabolised by a certain, so-called "beneficial" category of the intestinal microbiota (human or animal). Compared with probiotics, prebiotics take precedence over the probiotics on the market for nutraceuticals, including through improved resistance to digestive barrier, potentially cheaper production costs and easier incorporation in food preparations.

In addition to their action on the intestinal flora, the so-called prebiotic molecules can also be metabolised by other commensal flora, such as skin or vaginal flora, and participate in the development of a so-called "beneficial" plant according to the same principles as those cited above.

These prebiotics include (from a perspective commercial) under the name of isomaltooligosaccharides all the glucose oligosaccharides composed mainly of α-1,6 bonds in the main chain and variable rates in α-1,4; α-1.3 and/or α-1,2 bonds. They are found naturally in various fermented products like miso, sake, soy sauce and honey. They can be industrially produced by starch hydrolysates by means of α-transglucosylases. In this case, the IMOS contain exclusively α-1,6 and α-1,4 bonds. However, these products can also be synthesised by acceptor reaction using the transglucosylases of the family GH-70. In this case, the product may also contain α-1,3 and α-1,2 bonds in addition to the α-1,6 and α-1,4 bonds, depending on the binding specificity of the glucansucrase used. These connections (α-1,3 or α-1,2) are rare in nature, and impart to the molecules particularly interesting prebiotic properties, because they are even more difficult to digest than the other IMOS (including by certain pathogens that can partially recognise the α-1,6/α-1,4 IMOS).

The discovery made by the inventors makes it possible to consider the synthesis of a wide variety of polysaccharides having new and controlled structures and properties.

Thus, the inventors have demonstrated that the product obtained according to the reaction of their enzyme in the presence of sucrose and a linear dextran of molecular weight 1500 Da provides a polysaccharide having improved resistance to the action of digestive enzymes. The properties of this new polysaccharide as a prebiotic are therefore likely to be comparable to those of isomaltooligosaccharides or glucooligosaccharides connected in α-1,2.

Finally, such new polysaccharides may find use as prebiotic or as biopolymers, in the preparation of industrial formulations. Among the biopolymers, the polysaccharides (especially of plant origin, but also increasingly of microbial origin) can be used as texturising agents or stabilizers for various types of industrial products. An example of use of these biopolymers includes preparing readily degradable bioplastics. They could then replace the use of polymers of synthetic origin.

DETAILED DESCRIPTION OF THE INVENTION

A first object of the invention relates to an isolated polypeptide having the ability to form connections of glucosyl units in alpha 1,3 on an acceptor comprising at least one hydroxyl moiety and wherein said polypeptide comprises:

1) The pattern I of sequence SEQ ID NO: 1
2) The pattern II of sequence SEQ ID NO: 2
3) The pattern III of sequence SEQ ID NO: 3
4) The pattern IV of sequence SEQ ID NO: 4 or derivatives from one or several of said patterns; wherein said polypeptide furthermore has the aspartic residue (D) in position 5 of the pattern II (SEQ ID NO: 2), the glutamic acid residue (E) at position 6 of the pattern III (SEQ ID NO: 3) and the aspartic acid residue (D) in position 6 of the pattern IV (SEQ ID NO: 4).

These three amino acids can be readily identified by the skilled person, given the sequence homologies between enzymes with similar activities, such as representing the "catalytic triad" which is essential for the transglucosylase activity of the enzymes of the family GH 70 (LEEMHUIS et al., *Journal of Biotechnology*, vol. 163(2), p: 250-72, 2013).

In the polypeptide described above, the sequence SEQ ID NO: 1 is such that $ADX_1VANQ$ with $X_1$ corresponds to F or Y; the sequence SEQ ID NO: 2 is such that $SX_2RIDAISFVD$ with $X_2$ corresponds to M or I; the sequence SEQ ID NO: 3 is such that $HX_3SIVEAX_4X_5X_6X_7$ with $X_3$ corresponds to V or I, $X_4$ corresponds to P or S, $X_5$ corresponds to K or A, $X_6$ corresponds to G or D, $X_7$ corresponds to E or Q; the sequence SEQ ID NO: 4 is such that $IVHAHDKDIQDX_8VX_9X_{10}$ with $X_8$ corresponds to T or A, $X_9$ corresponds to S or I and $X_{10}$ corresponds to H or N.

Preferably, the pattern I has the sequence SEQ ID NO: 17 (ADFVANQ), the pattern II has the sequence SEQ ID NO: 18 (SMRIDAISFVD), the pattern III has the sequence SEQ ID NO: 19 (HISIVEAPKGE) and the pattern IV has the sequence SEQ ID NO: 20 (IVHAHDKDIQDTVIH).

Preferably, a polypeptide according to the invention is a polypeptide comprising the sequence SEQ ID NO: 5 (positions 636 to 1270 of the sequence SEQ ID NO: 9, domains A and C+, a part of the domain B) an orthologue, a derivative or a fragment thereof, preferably comprising the sequence SEQ ID NO: 6 (positions 586 to 1284 of the sequence SEQ ID NO: 9, comprising the entire domains A, B and C), an orthologue, a derivative or a fragment thereof.

Also advantageously, a polypeptide of the invention is a polypeptide comprising the sequence SEQ ID NO: 7 (positions 446 to 1356 of the sequence SEQ ID NO: 9, domains A, B, C and IV) an orthologue, a derivative or a fragment thereof, preferably comprising the sequence SEQ ID NO: 8 (positions 403 to 1606 of the sequence SEQ ID NO: 9, domains A, B, C, IV and V according to the homology with the transglucosylase GTF-180 of *L. reuteri* 180), an orthologue, a derivative or a fragment thereof.

Such a polypeptide may include the polypeptide truncated at its C-terminus (position 1313) of sequence SEQ ID NO: 12 (entire domains A, B and C).

Finally, a polypeptide of the invention is a polypeptide comprising or consisting of the sequence SEQ ID NO: 9 (entire sequence of the enzyme), an orthologue, a derivative or a fragment thereof.

The sequence SEQ ID NO: 9 corresponds to a polypeptide according to the invention, isolated from the strain *Leuconostoc citreum* NRRL B-742 (ATCC 13146), previously known as *Leuconostoc mesenteroides* NRRL B-742.

The term "orthologue" refers to a polypeptide having the same activity as the polypeptide of sequence SEQ ID NO: 9 of the strain *Leuconostoc citreum* NRRL742; wherein the polypeptide has an amino acid sequence that differs by at least one residue from the sequence SEQ ID NO: 9 and was isolated from a strain other than those mentioned above. More generally, by orthologue is meant a polypeptide having the same activity as the polypeptide of sequence SEQ ID NO: 9 isolated from a given bacterial strain which is derived from the same unique sequence as the polypeptide of sequence SEQ ID NO: 9 isolated from the strain *Leuconostoc citreum* NRRL B-742, which unique sequence is derived from the last common ancestor of these two strains.

Such orthologues include the sequences SEQ ID NO: 14 and SEQ ID NO: 16.

Advantageously, this orthologue was isolated from a bacterial strain belonging to the leuconostocaceae family, which includes the genera *Leuconostoc, Oenococcus* and *Weissela* Now this orthologue is preferentially isolated from a bacterial strain belonging to the genus *Leuconostoc,* or from the group consisting of *Leuconostoc argentinum, Leuconostoc carnosum, Leuconostoc citreum, Leuconostoc gasicomitatum, inhae, Leuconostoc kimchii,* and *Leuconostoc pseudomesenteroides.*

More simply, such an orthologue will have a sequence identity of at least 50 or 60% with the reference sequence including SEQ ID NO: 9, preferably at least 65%, 70%, 75%, 80% or 85%, and even more preferably at least 90%, 95%, 97%, 98% or 99% with the reference sequence.

By "derivative" is referred to a pattern or a polypeptide whose sequence has an identity percentage of at least 80%, for examples at least 85%, preferably at least 90%, and most preferably at least 95% with the reference sequence, namely a specific pattern (I, II, III or IV) or a polypeptide according to the invention, preferably with a polypeptide of sequence SEQ ID NO: 9.

Naturally, such a derivative of the polypeptide according to the present invention will have the enzymatic activity described above.

By "identity percentage between two polypeptide sequences" is meant the percentage of identical amino acids between two sequences to be compared, obtained with the best possible alignment of said sequences. This percentage is purely statistical and the differences between the two sequences are randomly distributed over the entire length of the amino acid sequences.

By "best possible alignment or optimal alignment" is meant the alignment for obtaining the highest percentage of identity. Sequence comparisons between two amino acid sequences are usually performed by comparing said sequences once they have been aligned in the best possible alignment; the comparison is then performed on comparison segments in order to identify and compare similarity regions. The best possible alignment to perform comparison can be performed using the local alignment algorithm developed by SMITH & WATERMAN (*Ad. App. Math.,* vol. 2, p: 482, 1981), using the overall alignment algorithm developed by NEEDLEMAN & WUNSCH (*J. Mol. Biol.,* vol. 48, p: 443, 1970), using the similarity method developed by PEARSON & LIPMAN (*Proc. Natl. Acd. Sci. USA,* vol. 85, p: 2444, 1988), using computer programs based on these algorithms (GAP, BESTFIT, BLAST P, BLAST N, FASTA, TFASTA, Genetics Computer Group, 575 Science Dr., Madison, Wis. USA), using multiple alignment algorithms MUSCLE (Edgar, Robert C., Nucleic Acids Research, vol. 32, p: 1792, 2004) ou CLUSTAL (Goujon M, McWilliam H, Li W, Valentin F, Squizzato S, Paern J, Lopez R. Nucleic acids research 2010 July, 38 Suppl: W695-9). To get the best possible alignment, we shall use preferably the BLAST program with the BLOSUM 62 matrix or the PAM matrix 30. The percentage identity is determined by comparing the two sequences aligned optimally, whereas said sequences may include additions or deletions in relation to the reference sequence so as to obtain the best possible alignment between these two sequences. The percentage identity is calculated by determining the number of identical positions between the two sequences, by dividing the number obtained by the total number of positions compared and by multiplying the result obtained 100 to generate the percentage identity between these two sequences.

By "fragment" is meant a polypeptide comprising the four units as described above and having a sequence of at least 150 amino acids, by way of example at least 450 amino acids, by way of example at least 700 amino acids, and particularly preferably a polypeptide of at least 1000 amino acids.

Preferably by fragment is meant a polypeptide comprising the domains A, B and C as the sequence SEQ ID NO: 12.

The terms "amino acid" and "amino acid" in the sense of the present invention correspond to any amino acid naturally present or to their residues. The amino acids may be identified either by their one-letter abbreviation, or by their three-letter abbreviation. (Asp D aspartic acid; Ile I isoleucine; Thr T threonine; Leu L Leucine; Ser S serine; Tyr tyrosine Y; Glu E glutamic acid; Phe F phenylalanine; Pro P proline; His H histidine; Gly G glycine; Lys K lysine; Ala A alanine; Arg R arginine; Cys C cystein; Trp W tryptophan; Val V valine; Gln Q glutamine; Met M methionine; Asn N asparagine). According to the present invention, the natural amino acids can be replaced by chemically modified amino acids.

The determination of the enzymatic activity of the polypeptide according to the invention can be determined by methods known to those skilled in the art, such as by use of the High Performance Liquid Chromatography Technique on reaction products with the polypeptide of the invention (MOULIS et al., *J. Biol. Chem,* 2006) or assay of reducing sugars by the method in dinitrosalycilic acid (SUMNER & HOWELL, 1935). More specifically, this enzymatic activity is expressed in glucansucrase units which represents the amount of enzyme which liberates one µmol of fructose per minute at 30° C. with a concentration of 100 g·L-1 sucrose and a buffer at pH 5.2 comprising 50 mM sodium acetate. This activity is preferably determined by measuring the initial rate of production of reducing sugars (fructose) by using the DNS method (SUMNER & HOWELL). To do this, a standard range of 0-2 g·L-1 of fructose is established. During kinetics, 100 µl of reaction medium are then sampled and the reaction is stopped by adding an equal volume of reagent. The samples were then heated for 5 min at 95° C., cooled in ice, diluted in half with water and the absorbance is read at 540 nm.

The polypeptide is "isolated" in the sense of the present invention inasmuch as it was removed from its original environment (the environment in which it is naturally located). For example, a polypeptide present naturally in a cell is not isolated. The same polypeptide separated from the other adjacent polypeptides within the cell in which it is naturally present, most commonly by a purification process, is isolated.

According to a preferred embodiment, the substrate of the polypeptide according to the invention is selected from the group consisting of α-D-glucopyranosyl fluoride, p-nitrophenyl α-D-glucopyranoside, α-D-glucopyranosyl α-L-sorofuranoside, lactulosucrose and sucrose, preferably sucrose which is the natural substrate.

The "sucrose" consists of an α-D-glucopyranosyl unit and a β-D-fructofuranosyl unit associated by a link (alpha1-beta2). Hydrolysis of sucrose leads to a mixture of glucose and fructose.

By "glucosyl unit" is meant the residue resulting from the cleavage of sucrose, which is temporarily associated with the enzyme in the form of a β-glucosyl-enzyme and that is transferred to an acceptor comprising a hydroxyl moiety by forming a glycosidic bond with that hydroxyl moiety.

By "connection in alpha-1,3" is meant according to the invention a glucoside bond of condensation between the —OH function of the carbon located in position 1 of a first sugar and an —OH function of carbon located in position 3 of another sugar, said glucosidic bond being formed in an alpha configuration.

By "connection of glucosyl units in alpha-1,3" is meant a glucoside bond in alpha 1,3 between an acceptor according to the invention comprising at least one hydroxyl moiety and a glucosyl unit derived from the hydrolysis of sucrose by the polypeptide of the invention.

By "acceptor" according to the invention is meant any organic molecule comprising at least one free hydroxyl moiety (—OH), which acceptor is added to the reaction medium on top of the donor substrate of glucosyl units.

Such acceptor may be selected from the carbohydrate and non-carbohydrate acceptors.

Examples of non-carbohydrate acceptors include, but without being limited thereto, alcohols, polyols, phenolic compounds or still amino acids.

Examples of carbohydrate acceptors are preferably polysaccharides or more generally acceptor comprising glycosyl units.

According to a preferred embodiment, an acceptor according to the invention is a carbohydrate acceptor, preferably the latter will include glucosyl units.

Still according to a preferred embodiment, an acceptor of the invention includes polysaccharides. By polysaccharide is meant a sugar polymer containing n sugar units wherein n is an integer greater than or equal to 3.

Advantageously, these polysaccharides are composed exclusively of monomers of (glucans), and they may be linear or branched. These polysaccharides may correspond either to the α-glucans or to β-glucans.

The α-glucans are glucose polymers linked together in a α position. Examples of α-glucans may include dextran (more than 50% of α-1,6 bonds in the main chain), dextran branched in α-1,2 (by the action of a α-1,2 "branching sucrase"), alternan (alternate α-1,6 and α-1,3 bonds in the main chain), mutan (more than 50% of α-1,3 bonds), reuteran (α-1,4 and α-1,6 bonds in the main chain), the starch (α-1,4 and α-1,6-glucan), amylopectine (α-1, 4 and α-1,6-glucan), was glycogen (α-1,4-glucan), amylopectin (α-1,4 and α-1,6-glucan) and p (α-1,4 and α-1,6-glucan).

The β-glucans are glucose polymers linked together in β position. Examples of β-glucans include cellulose (β-1,4-glucane), curdlan (β-1,3-glucane), laminarin (β-1,3-et β-1,6-glucan), lentinan (β-1,6:β-1,3-glucan), pamylon, pleuran (β-1,3-et β-1,6-glucan) and zymosan (β-1,3-glucan).

Now, a preferred acceptor would be an α-glucan such as amylose, starch, amylopectin, dextran, glycogen or pullulan, dextrans branched in α-1,2, alternan, mutan and reuteran.

According to a particularly preferred embodiment, an acceptor according to the invention is a dextran, a polymer whose glucosyl units are connected together by alpha 1-6 bonds. This polymer may also include branches consisting of alpha-1,2 or 1,3 or 1,4 bonds.

Dextrans used as an acceptor according to the invention have a molecular weight (MW) between 300 and $10^9$ Dalton (Da), preferably between $10^3$ and $10^9$ Da and even more preferably between 1000 and $2.10^6$ Da.

The advantage of the invention lies in that the polypeptide as described above is responsible for the formation of connecting glucosyl units in the alpha-1,3 position of an acceptor.

Preferably, the polypeptide according to the invention has the ability to form connections of glucosyl units in alpha 1,3 on an acceptor at a rate between 1 and 50%, preferably between 5% and 40%, and more preferably still between 10 and 40%.

Even more preferably, the polypeptide according to the invention has the ability to form connections of glucosyl units in alpha 1,3 on an acceptor at a maximum rate of 50%.

Another object of the invention concerns an isolated polynucleotide encoding a polypeptide as defined above, a fragment or a derivative thereof.

According to the invention, said polynucleotide is a DNA or RNA molecule.

By "polynucleotide" is meant broadly a DNA molecule such as for instance a cDNA (complementary DNA) or genomic or synthetic DNA, or an RNA molecule, such as a messenger RNA or synthetic RNA, as well as analogues of DNA or RNA containing non-natural nucleotide analogues, non-natural internucleotide linkages, or both. Preferably, said polynucleotide is a DNA molecule. The polynucleotides may have any topological conformation, such as linear or circular.

In a preferred embodiment of the invention, said polynucleotide is defined by the sequence SEQ ID NO: 10.

Another object of the invention relates to an expression vector comprising a polynucleotide as described above.

By "vector" is meant any vehicle capable of facilitating the transfer of a polynucleotide into a cell. In general, the vectors of the invention include, without limitation thereto, plasmids, cosmids, phagemids or other vehicles derived from viral or bacterial sources that have been manipulated for insertion or incorporation of a nucleotide sequence.

The choice of vectors usable in the context of the present invention is vast. They can be cloning and/or expression vectors. In general, they are known to those skilled in the art and many of them are commercially available but it is also possible to construct them or to modify them by genetic engineering techniques.

Preferably, the vectors according to the invention are plasmid vectors, also known as plasmids. The plasmids were widely described in the prior art and are well known to the skilled person (see eg SANBROOK et al., "Molecular Cloning: A Laboratory Manual," Second Edition, Cold Spring Harbor Laboratory Press, 1989). Examples include the most commonly used plasmids such as pBR322, pUC18, pUC19, pRC/CMV, SV40 and pBlueScript, pET-53-DEST, pET-55-DEST, pBAD49-DEST, pET-60-DEST. The plasmids can be designed by the use of restriction enzymes and ligation reactions or recombination systems to remove or insert specific DNA fragments. The plasmids in which the nucleotide sequences are inserted, are in the form of a single or double stranded, linear or circular DNA.

Preferably, a vector implemented in the context of the present invention contains a replication origin ensuring the initiation of replication in a producing cell and/or a host cell. It also contains the elements necessary for the expression of a polynucleotide of the invention, such as a promoter and a terminator. Examples of suitable promoter according to the invention include, but are not limited to, T7, araBAD, pLac, POX2, AOX (alcohol oxidase) promoters.

It may further comprise one or more selection gene(s) to select or identify the cells transformed or transfected with said vector (complementation of an auxotrophic mutation, a gene encoding resistance to an antibiotic . . . ). It can also comprise additional elements improving its maintenance and/or its stability in a given cell (cer sequence which promotes the monomeric maintenance of a plasmid, integration sequences into the cell genome).

The vector of the invention may optionally be associated with one or more substances improving the efficiency of transformation or transfection and/or the stability of the vector. These substances are widely documented in the literature accessible to those skilled in the art. By way of illustration but without limitation, they may be polymers, in particular cationic lipids, liposomes, nuclear proteins or neutral lipids. These substances may be used alone or in combination. One possible combination is a plasmid recombinant vector associated with cationic lipids (DOGS, DC-CHOL, spermine-chol, spermidine-chol, etc.) and neutral lipids (DOPE).

The polynucleotide, preferably the DNA molecule, in the expression vector is operatively linked to a promoter to direct the synthesis of RNA. For example, developers may be eukaryotic or prokaryotic promoters such as CMV immediate early, HSV thymidine kinase, early and late SV40, LTRs from retroviruses, and mouse metallothionein-I. The expression vector also contains a ribosome binding site for initiating the translation and a transcription vector. The vector should also include enhancer sequences of the expression.

By "operably linked to a promoter" is meant the link through which a promoter is located contiguously to the polynucleotide of the invention for controlling the expression of said sequence.

The term "promoter" is well known to those skilled in the art and refers to a DNA region adjacent to a gene to which RNA polymerase binds to start the transcription.

Another object of the invention also relates to a transformed host cell comprising a vector according to the invention.

For the purposes of the present invention, such a cell consists of any cell which can be transformed or transfected by an inventive vector as described above.

The cell is called "host cell" and may be a prokaryotic cell or a eukaryotic cell.

Preferably, the host cell transformed according to the invention is a prokaryotic cell selected from the group consisting of eubacteria, archaebacteria and cyanobacteria.

The bacterial expression systems can be used in the context of the present invention. Examples of bacterial host cells include bacteria of the genera *Escherichia* (e.g. *Escherichia coli*), *Pseudomonas* (e.g. *Pseudomonas fluorescens* or *Pseudomonas stutzerei*), *Proteus* (e.g. *P. mirabilis*), *Ralstonia* (such as *Ralstonia eutropha*), *Streptomyces*, *Staphylococcus* (eg *Streptomyces carnosus*), *Lactococcus* (eg *Lactoccocus lactis*), *Bacillus* (eg *Bacillus subtilis, Bacillus megaterium* or *Bacillus licheniformis*), *Lactobacillus* or *Leuconostoc* etc.

More preferably, the host cell transformed according to the invention is a eukaryotic cell selected from the group consisting of animal, fungal, yeast, and plant cells.

Yeast cells are also hosts cells which can be suitable in the scope of the invention. Examples of yeast host cells which may be used include, but are not limited to, *Saccharomyces cerevisiae, Schizosaccharomyces pombe, Klyveromyces lactis, Yarrowia lipolytica, Hansenula polymorpha* or *Pichia pastoris*.

Fungal expression systems are also conceivable within the scope of the present invention, such as *Aspergillus Niger, Chrysosporium lucknowense, Aspergillus* (e.g. *Aspergillus oryzae, Aspergillus Niger, Aspergillus nidulans,* etc.), *Podospora anserina* or *Trichoderma reesei*.

Other expression systems such as mammalian expression systems can also be used in the context of the invention, such as the NSO, CHO, BHK cell lines, transgenic systems of mammalian origin, but also the cells insect or viral expression systems such as bacteriophage M13, T7 or λ, or the expression systems Baculovirus Preferably, the host cell according to the present invention is a prokaryotic cell.

The terms "transformed host cell," "transformed" and "transformation" as defined in the present invention refer to the introduction of DNA into a cell. The introduction of a polynucleotide or a vector as described in the present invention into the host cell can be effected by methods well known to those skilled in the art such as the electroporation, heat shock on competent cells, recombination, conjugation, transfection by PEI, by calcium phosphate, transfection by DEAE dextran or still electroporation.

According to another object, the invention provides a composition comprising at least one polypeptide, one polynucleotide, one vector or one host cell as described above.

Another object of the invention relates to a method of producing a polypeptide as described above, said method comprises the steps of:
 a) inserting a polynucleotide or a vector as described previously in a host cell;
 b) culturing said cell obtained in step a); and
 c) extracting the polypeptide of the invention from the culture obtained in step b).

Step (a) of introducing a polynucleotide or a vector as described above into the host cell is accomplished by well-known processing techniques to those skilled in the art, such as transfection, lipofection, transformation by lithium acetate, biolistic transformation, transformation by PEI, protoplast fusion, liposome transformation, transformation by *Agrobacterium tumefaciens,* or still viral or adenoviral infections.

Extraction of the polypeptide of the invention is made from the culture of step (b) and produced by techniques well-known to those skilled in the art. If the host organism produces the polypeptide extracellularly, the culture supernatant is recovered by centrifugation and may be directly used for implementing the syntheses of products. If the expression is intracellular, the cells are centrifuged, concentrated, then lysed by means of lysozyme and detergents or crushed ultrasonically or treated by mechanical breakage using glass beads or FRENCH press.

If necessary, the extraction can consist of a purification of the polypeptide may be performed by affinity chromatography for chelating metals such as nickel or cobalt and using a tag (label) of type "Histidine" (6 successive histidines) fused to the polypeptide sequence as described above.

Another object of the invention relates to a process for producing acceptors connected to glucosyl units in alpha 1,3 comprising a rate of connections of such glucosyl units in alpha 1,3 between 1 and 50%, said method comprising the steps of:
 mixing in a reaction medium a polypeptide according to the invention, of a substrate of said polypeptide and an acceptor comprising at least one hydroxyl moiety; and ii) incubating said mixture obtained in step i) so as to obtain the connection of glucosyl units in alpha-1,3 on said acceptor.

The term "acceptor connected to glucosyl units in alpha 1,3" according to the invention an acceptor as defined above which are attached by the action of a polypeptide according to the invention of glucosyl units derived from the hydrolysis of the substrate.

According to a preferred embodiment, an acceptor connected to glucosyl units in alpha-1,3 according to the invention is selected from the group consisting of polysaccharides, preferably glucans, in particular α-glucans such as α-1,6 glucans (eg dextran).

According to a preferred embodiment and as described above, the substrate of the polypeptide according to the invention is selected from the group consisting of α-D-glucopyranosyl fluoride, p-nitrophenyl α-D-glucopyranoside, α-D-glucopyranosyl, α-L-sorofuranoside, lactulosucrose and sucrose, preferably sucrose.

According to a preferred embodiment, the method according to the invention allows to control the rate of alpha-1,3 connections of the acceptor by directly varying the ratio between the substrate concentration and the acceptor concentration.

According to a preferred embodiment of the invention, said method is characterised in that it is intended to obtain an acceptor connected to glucosyl units in alpha 1,3 at a rate between 1% and 50%, preferably between 5 and 40% and more preferably still between 10 and 40%. This variation is possible depending on the ratio between the concentration of the substrate to that of the free hydroxyl moieties of the acceptor molecule, or the ratio between the mass concentration of the substrate to that of the acceptor in the case of dextran and sucrose.

Advantageously, the concentrations of acceptor and substrate are adjusted so as to obtain a degree of connection between 35 and 50%, preferably between 35 and 40%. Typically, this degree of connection is obtained with a ratio greater than or equal to 1.

Advantageously, the concentrations of acceptor and of substrate are adjusted so as to obtain a degree of branching between 20 and 35%. Typically, this level of connection is achieved with a ratio of between 0.5 and 1.

Advantageously still, the concentrations of acceptor and substrate are adjusted so as to obtain a degree of branching less than 20%. Typically, this rate of connection is obtained with a ratio less than 0.5.

According to the invention, the rate of connection in alpha-1,3 obtained in the context of this method is considered in relation to all the sites available on said acceptor.

According to a particular embodiment, said method according to the invention further comprises a step c) of purification of acceptor connected to glucosyl units in alpha 1,3.

Still according to a particular embodiment, the method of the invention comprises a step d) of characterisation of the acceptors connected to glucosyl units in alpha-1,3 of the invention. Such a characterisation step may be performed by various methods well-known to those skilled in the art.

By way of example, high performance liquid chromatography technique (HPLC), mass spectrometry, nuclear magnetic resonance spectrometry (NMR), chemical techniques such as methylation and acetolysis or ELISA with monoclonal antibodies specific for alpha-1,3 bonds will be used.

Another object of the invention relates to an acceptor connected to glucosyl units in alpha-1,3 obtainable by the process as described above.

Said acceptor may not be a dextran.

Also advantageously, the rate of connection of said acceptor is less than 50%, preferably less than 40%.

The present patent application is also intended to cover the various possible uses of a polypeptide, a polynucleotide, a vector, a host cell and/or a composition of the invention as described above.

Thus, another object of the invention relates to the use of a polypeptide, a polynucleotide, a vector, a host cell and/or a composition according to the invention for the production of acceptors connected to glucosyl units in alpha-1,3.

Preferably, said acceptors are connected to glucosyl unit in alpha 1,3 at a rate between 1 and 50%, preferably between 5 and 40%, and most preferably still between 10 and 40%.

This patent application is also intended to cover the various possible uses of an acceptor connected to glucosyl units in alpha-1,3 of the invention.

The invention thus relates to the use of an acceptor connected to glucosyl units in alpha-1,3 produced from a polypeptide of the invention as a bulking agent, thickener, emulsifier, texturising agent and/or stabiliser in the preparation of industrial food, cosmetic, agrochemical, petrochemical and pharmaceutical formulations.

These applications consist of the use of these acceptors connected to glucosyl units in alpha-1,3 as biopolymers.

Examples of industrial formulations of the invention include without limitation bioplastics, but also the food formulations, such as bakery products, as well as formulations in the pharmaceutical sector.

Other examples of industrial formulations also include formulations for the construction, paint, paper, textile, plant protection, water treatment, oil industries.

The invention also relates to the non-therapeutic use of an acceptor connected to glucosyl units in alpha-1,3 as an agent prebiotic.

The acceptors connected to glucosyl units in alpha-1,3 produced according to the invention has the advantages of a better resistance to the digestive barrier, a better stability, potentially cheaper production costs and greater ease to be incorporated in food preparations.

Prebiotics are non-digestible food ingredients that arrive intact in the colon where they are then specifically metabolised by a certain, so-called "beneficial" category of the intestinal microbiota (human or animal).

Non-limiting examples of prebiotics effects include improved intestinal transit in animals and humans, improved absorption of minerals such as calcium, magnesium, zinc or even iron, reduced intestinal inflammation or still reduced growth of pathogens.

EXAMPLES

Example 1

Screening of New Enzymes in *L. citreum* NRRL B-742

After sequencing of the genome of the strain *L. citreum* NRRL B-742, a gene proved particularly original. Indeed the corresponding putative protein was found to have a sequence having a maximum of only 54% identity with the putative glycoside hydrolase *Leuconostoc fallax* KCTC 3537 whose sequence is available in the database, and referenced by the NCBI under number ZP_08312597. Now, any other protein sequence with significant identity could be identified.

This gene encodes a putative transglucosylase of 1888 amino acids, having the characteristic catalytic triad DED and the 4 conserved regions usually described in transglucosylases of family 70. The schematic representation of the protein is shown in FIG. 1 (based on the alignment of protein sequences with GTF180 with 5 domains: i) domain V (403-446 and 1356 to 1800), ii) domain IV (446-586 and 1284-1356), iii) domain A (catalytic) (636-899, 1052-1191 and 1231-1270), iv) domain B (586-636, 1191-1231 and 1270-1284) and v) domain C (899-1052). The catalytic amino acids (DED) are indicated with a star in the primary structure and are shown in bold and red in the different patterns II, III and IV.

Now, particularly original protein patterns were identified upstream and downstream of amino acids of the catalytic triad, usually in highly conserved regions (see table 1).

Due to the originality of this putative transglucosylase, it was decided to initiate cloning so as to begin its biochemical characterisation.

Simultaneously, a truncated form of the signal peptide and C-terminal, ΔPS ΔC-1313 SEQ ID NO: 13 and SEQ ID NO: 12 for the nucleic and protein sequences, respectively) of the protein has been cloned and expressed in the strain of *E. coli* BL21 DE3 star, allowing again a significant expression of the protein; which expression has proved almost twice higher than that of the wild-type protein.

Example 3

Reaction of a Polypeptide According to the Invention with Sucrose, a Dextran-Type Acceptor and the Enzyme Object of the Invention and Analysis of the Products of this Reaction To characterise the functional properties of this putative transglucosylase, the enzyme was first implemented on sucrose alone, a natural substrate of enzymes of the GH70 family.

TABLE 1

Sequence Alignment of conserved regions of the catalytic heart of the new transglucosylase (called α-1,3BrS in the table) and orthologues identified (from *Leuconostoc fallax* KCTC3537 and *Leuconostoc citreum* LBAE E16) with characterised enzymes and with known specificity of links

| GenBank | | | Pattern II | | Pattern III | | Pattern 2 | | Pattern 1 | Specificity |
|---|---|---|---|---|---|---|---|---|---|---|
| AAC63063.1 | GtfI [Sd] | 449 | SIRVDAVDNVD | 486 | HVSIVEAWSDN | 559 | FARAHDSEVQDLIRD | 931 | ADWVPDQ | α-1,3 |
| AAA88588.1 | GtfB [Sm] | 1011 | SIRVDAVDNVD | 1048 | HLSILEAWSDN | 1120 | FIRAHDSEVQDLIAD | 1488 | ADWVPDQ | |
| BAA26114.1 | GtfSI [Sm] | 473 | SIRVDAVDNVD | 510 | HLSILEAWSDN | 583 | FIRAHDSEVQDLIRD | 954 | ADWVPDQ | |
| AAU08015.1 | GtfA [Lr] | 1020 | SVRVDAPDNID | 1056 | HINILEDWNHA | 1128 | FVRAHDNNSQDQIQN | 1508 | ADWVPDQ | α-1,4/ |
| AAY86923.1 | GtfO [Lr] | 1020 | SVRVDAPDNID | 1056 | HINILEDWNSS | 1128 | FIRAHDNNSQDQIQN | 1508 | ADWVPDQ | α-1,6 |
| CAB65910.2 | Asr [Lm] | 631 | GIRVDAVDNVD | 668 | HLSILEDWNGK | 762 | FVRAHDYDAQDPIRK | 1168 | ADWVPDQ | α-1,6/ α-1,3 |
| ABQ83597.1 | GtfW [Lr] | 748 | GFRVDAADNID | 785 | HLVYNEGYHSG | 568 | FVTNHDQR-KNVINQ | 1216 | EDLVMNQ | α-4,6 |
| AAU08003.2 | GtfML4 [Lr] | 1012 | GFRVDAADNID | 1049 | HLSYNEGYHSG | 1121 | FVTNHDQR-KNLINR | 1479 | EDIVMNQ | |
| ABF85832.1 | DsrCB4 [Lc] | 526 | GIRVDAVDNVD | 563 | HLSILEDWSHN | 636 | FVRAHDSEVQTVIAQ | 1001 | ADWVPDQ | α-1,6 |
| CAB76565.1 | DsrC [Lm] | 498 | GIRVDAVDNVD | 535 | HLSILEDWSHN | 608 | FVRAHDSEVQTVIAQ | 973 | ADWVPDQ | |
| AAD10952.1 | DsrS [Lm] | 547 | GIRVDAVDNVD | 584 | HLSILEDWSHN | 657 | FVRAHDSEVQTVIAQ | 1023 | ADWVPDQ | |
| AAU08001.1 | GTF180 [Lr] | 1021 | GIRVDAVDNVD | 1058 | HINILEDWGWD | 1131 | FVRAHDSNAQDQIRQ | 1503 | ADWVPDQ | |
| CAD22883.1 | GBD-CD$_2$ [Lc] | 2206 | SIRIDAVDFIH | 2243 | HISLVEAGLDA | 2317 | IIHAHDKGVQEKVGA | 2688 | ADVVDNQ | α-1,2 |
| | α-1,3 BrS [Lc] | 667 | SMRIDAISFVD | 704 | HISIVEAPKGE | 783 | IVHAHDKDIQDTVIH | 1182 | ADFVANQ | |
| | α-1,3 BrS [*L. fallax*] | 734 | SIRIDAISFVD | 771 | HVSIVEASADQ | 845 | IVHAHDKDIQDAVSN | 1232 | ADYVANQ | |
| | α-1,3 BrS [*L. citreum* E16] | 667 | SMRIDAISFVD | 704 | HISIVEAPKGE | 783 | IVHAHDKDQIDTVIH | 1182 | ADFVANQ | |

Example 2

Production of a New Enzyme in *E. Coli*

The gene encoding this enzyme has been cloned into several vectors (pET 53, 55, 49 and 60) commercially available from NOVAGEN or I NVITROGEN, and expressed in different various of *E. coli* (TOP10, BL21AI, BL21 DE3 Star, Arctic Express DE3).

This cloning resulted in a consistent production of the protein. This production has helped initiate the experiments of biochemical characterisation to clarify the catalytic properties of the identified enzyme.

Unexpectedly, the chromatographic analyses (HPAEC-PAD, HPSEC) showed that the enzyme alone is only capable of hydrolysing the substrate in equimolar amounts of glucose and fructose. Now and from sucrose alone, this enzyme showed no ability to produce polymers of glucosyl units, as well as its truncated form.

It is interesting to note that to date, bioinformatic analyses on the primary structure of the GH of the family 70 would not predict this feature (structural determinants governing the ability—or not—of a transglucosylase polymerising are not yet known).

While nothing presaged that this protein had still an activity, the latter (as well as its truncated form) was also incubated in the presence of sucrose and a linear dextran (glucan composed exclusively of α-1,6 bonds) of a molecular weight of 1500 Da.

We incubated for 16 h at 30° C., enzyme in sucrose (from 25 g/L to 170 g/L) in the presence of dextrans of variable molecular weight (from 1500 Da to $2.10^6$ Da) and of varying concentration of 30 g/L to 100 g/L; the sucrose/acceptor (M/M) ratio varies depending on the desired connection rate in α-1,3. The reaction medium was buffered with a solution with final sodium acetate with 50 mM, pH 5.2. A sample at initial and final times of the reaction was conducted, heated at 95° C. for 5 minutes to stop the reaction and analysed by various chromatographic (HPAEC-PAD, HPSEC) and structural (proton NMR) techniques.

More specifically, monosaccharides, disaccharides, and small oligosaccharides (degree of polymerisation less than 20) were separated and quantified by HPAEC-PAD (High Performance Anion Exchange Chromatography with Pulsed Amperometric Detection) on column Dionex CarboPac PA-100. A sodium acetate gradient of 6 to 300 mM in 36 min, containing 150 mM of sodium hydroxide used to separate glucose, fructose, sucrose, leucrose, isomaltooligosaccharides, etc. Standard ranges of 5, 10, 15 and 20 mg·kg-1 of these sugars were performed to allow quantification. These samples were diluted for a total sugar concentration of 25 mg·kg-1.

Analyses by HPSEC (High Performance Size Exclusion Chromatography-) were used to estimate the molecular weight of oligosaccharide populations or of polymers synthesised during the reactions. The separation was done using two columns SHODEX (OH-Pack SB-805 and 802.5) arranged in series. Solutions of 1, 2.5, 5 and 10 gL-1 sucrose, fructose, maltoheptaose, Dextran 11.3 kDa, 68.4 kDa, 503 kDa, 2000 kDa served as benchmarks. The samples were diluted 10 times to reach a maximum concentration of 10 g·kg-1. A solution of 0.45 M $NaNO_3$+1% (v/v) ethylene glycol in 0.3 mL·min-1 is used as an eluent, and the samples should be diluted in the mobile phase. Column and precolumn were maintained at 70° C., detection is performed by refractometry.

For the NMR analyses, the synthesised polymers were stored at −80° C. overnight and then be freeze-dried (CHRIST ALPHA apparatus 2-4). 10 mg of the powder obtained are then dissolved in 0.5 mL of deuterated water and analysed by proton NMR. The 1H NMR spectra were acquired on a spectrometer BRUKER AVANCE (500 MHz). The data were then treated with the TOPSPIN 3.0 software.

Figure 2:
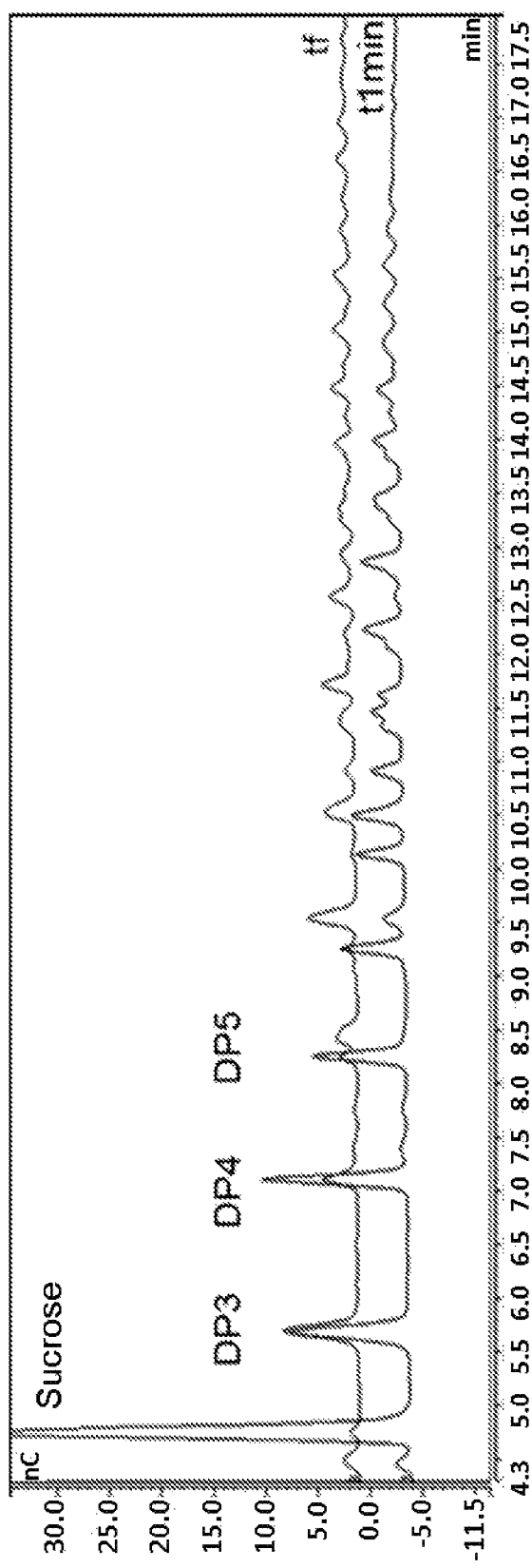
FIG. 2 shows profiles of chromatographic analyses by HPAEC-PAD.

FIG. 2 shows the HPAEC-PAD profiles of a reaction using dextran 1500 Da as an acceptor.

Figure 3:
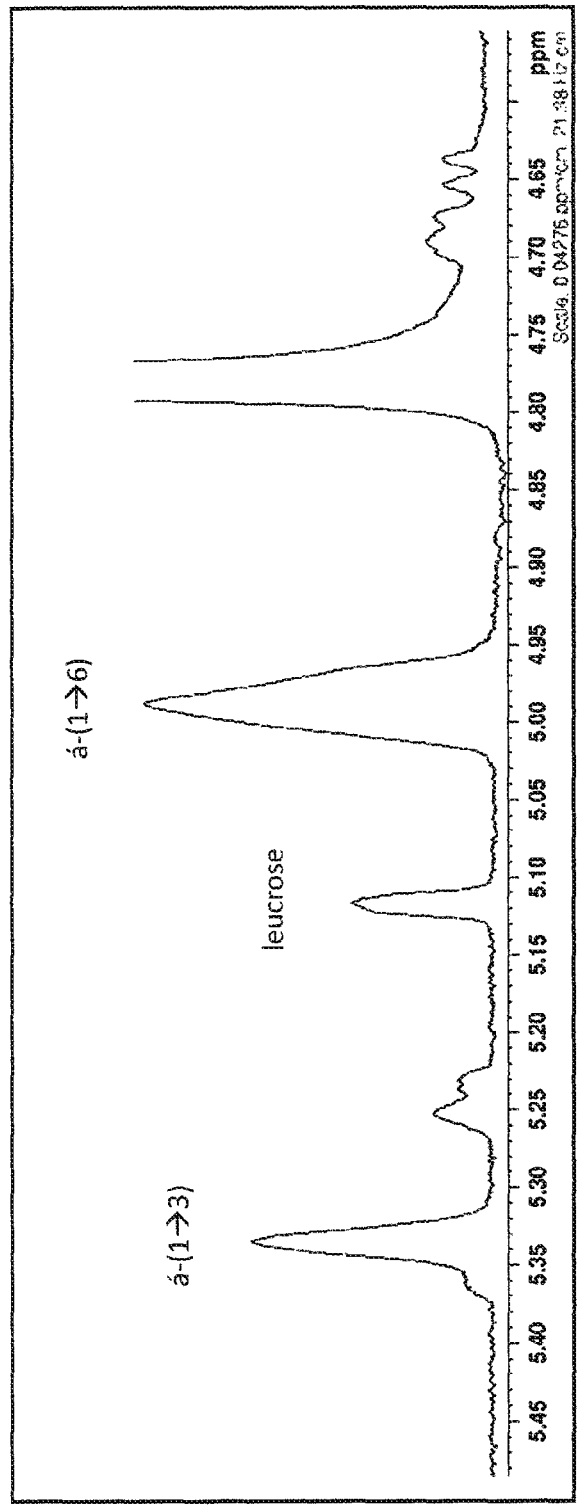
FIG. 3 shows an NMR profile.

FIG. 3 shows the profile NMR of dextran 1500 Da obtained at the end of incubation.

Figure 4:
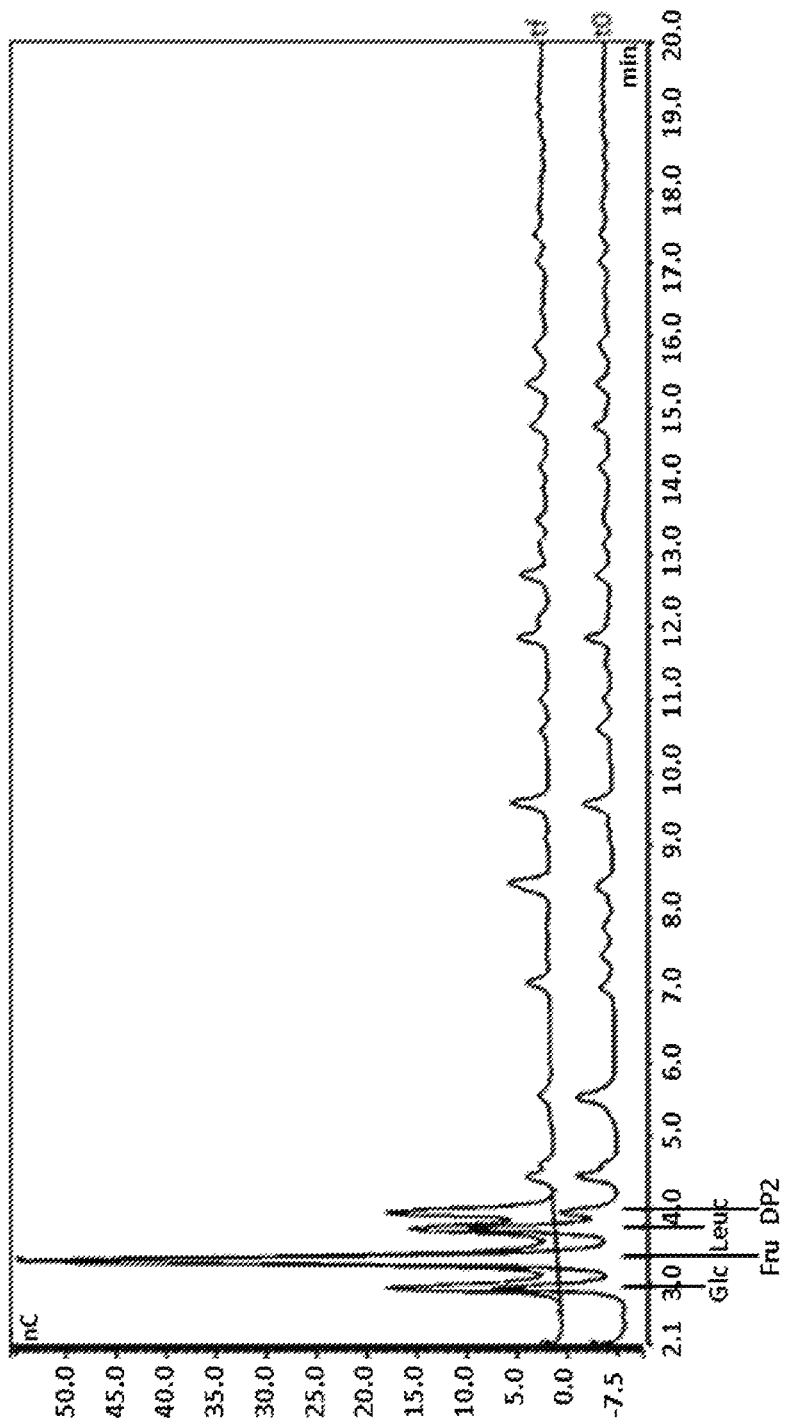
FIG. 4 shows profiles of chromatographic analyses by HPAEC-PAD.

FIG. 4 shows the HPAEC-PAD profiles of endodextranase digestion of the products of the sucrose+dextran 1500 Da acceptor reaction (to=1500 Da dextran connected in α-1,3).

While no polymerisation was observed in the presence of sucrose, the results revealed a characteristic modification of dextran. A more detailed analysis of chromatographic results and structural analyses by proton NMR show the synthesis of branches in α-1,3 on the acceptor molecule (FIGS. 2 and 3). In particular, the reaction product is resistant to the action of an endodextranase, an enzyme specific for the hydrolysis of α-1,6 bonds (FIG. 4). More broadly, these results suggest a resistance to the action of digestive enzymes, and therefore the existence of prebiotic properties comparable to those of isomaltooligosaccharides or gluco-oligosaccharides connected in α-1,2 (GOFFIN et al. *Crit Rev. Food Sci. Nutr.*, vol. 51(5), p: 394-409, 2011; SARBINI et al., *Appl. Environ. Microbiol.*, vol. 77(15), p: 5307-15, 2011).

The enzyme, as its truncated form, is particularly effective shown also to catalyse the transfer of glycosyl residues on isomaltooligosaccharides since the addition of dextran 1500 Da as an acceptor molecule in the reaction medium has the effect of multiplying the activity of the enzyme by a factor of 26 (compared to the activity measured on sucrose alone).

Finally, these results demonstrate that the identified protein is responsible for the connections in α-1,3 of the glucan corresponding to the proportion S and that a single enzyme, as was previously believed, is not the initiator of the synthesis of this specific glucan. Because of this activity, the corresponding gene encoding an "enzyme responsible for glucosylations specific by connection in α-1,3" is named α-1,3BrS.

Example 4

Influence of Changes in Concentration of Substrate/Acceptor on the Number of Connections Obtained in Alpha-1,3

Additional experiments have also shown that by varying the sucrose concentration relative to the concentration of dextran 1500 Da (donor/acceptor ratio), it is possible to control the degree of connection in α-1,3 of this the small dextran.

Figure 5:
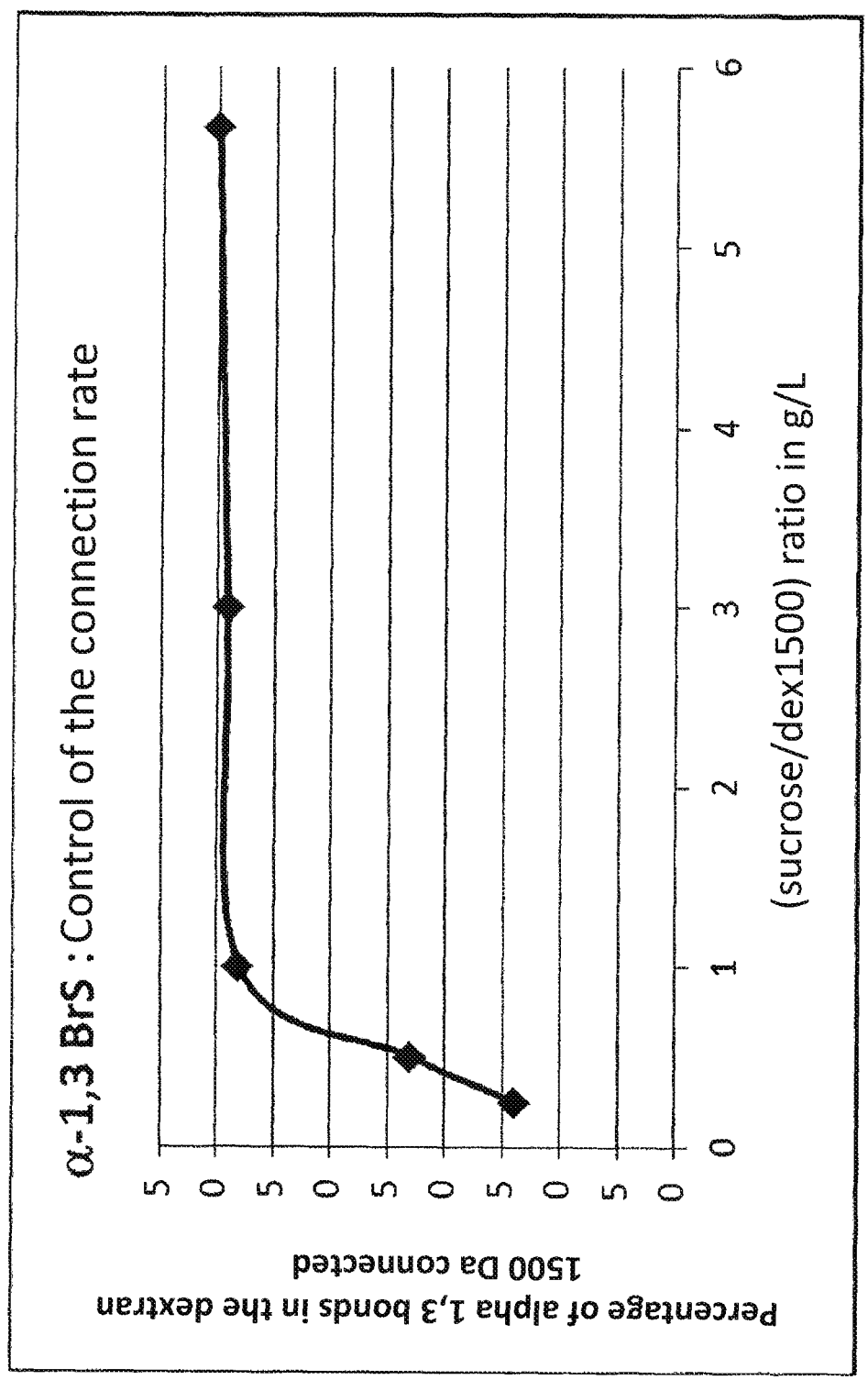
FIGS. 5 and 6 show the evolution of the rate of $\alpha$-1,3 bonds depending on the sucrose/hydroxylated acceptor ratio for the whole enzyme and the truncated enzyme respectively.

FIG. 5 shows the control of the rate of α-1,3 bonds according to the sucrose/dextran 1500 Da ratio (using mass concentrations).

Figure 6:
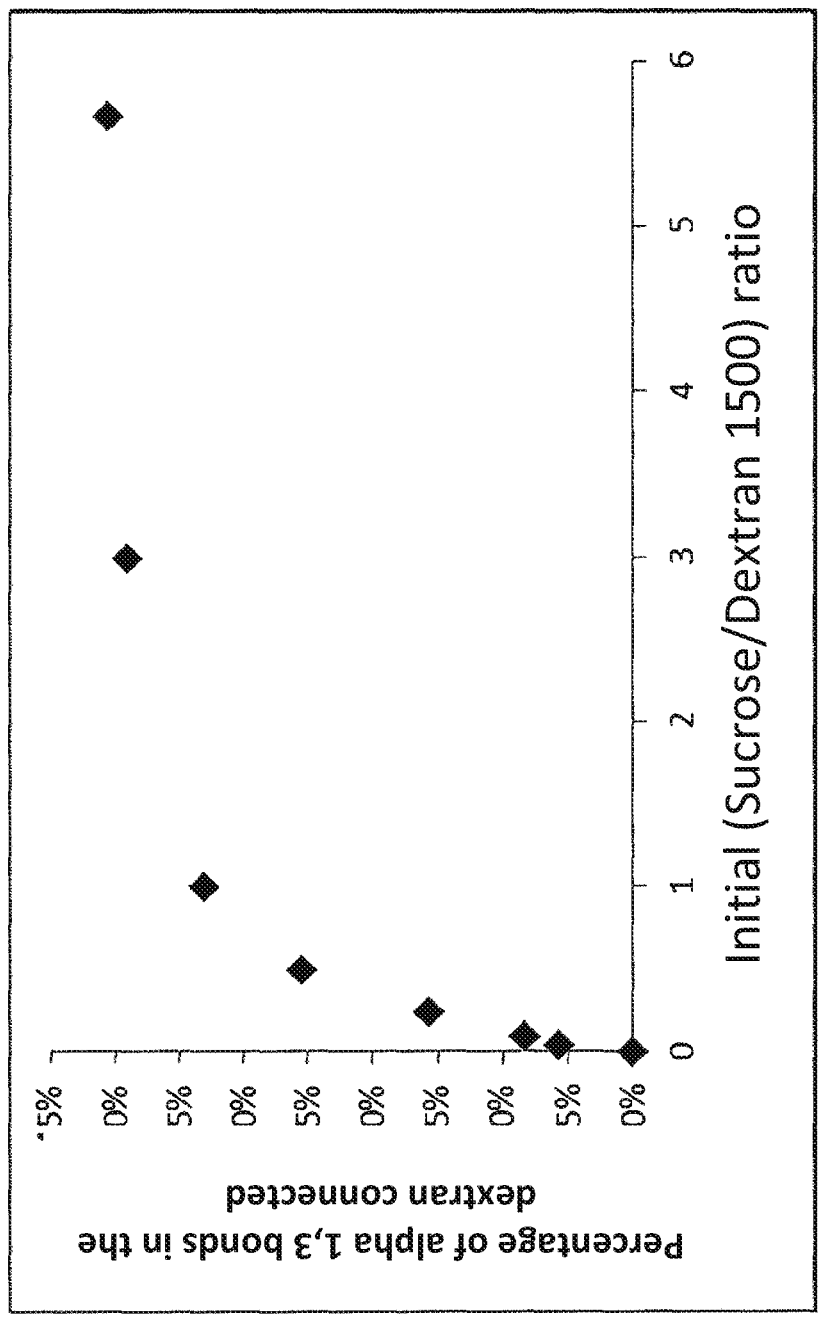

FIG. 6 also shows the control of the rate of α-1,3 bonds according to the sucrose/dextran 1500 Da ratio but with the truncated enzyme.

The results show that at a sucrose/Dextran 1500 ratio (equivalent to a substrate/hydroxyl moiety ratio) greater than or equal to 1, we arrive at a degree of substitution of about 40% and approaches 50% by increasing the substrate concentration. Now, by modulating this report, we come to reduce the substitution rate. Thus, for a ½ ratio, the substitution rate is slightly lower than 25%, and a ratio of ⅓, the rate of substitution rises and is slightly below 15%.

Note that the inventors on the same substrate with the truncated form came to the same results (FIG. 6), confirming that the truncated enzyme retains the same specificity as the whole shape.

Example 5

Dextran Acceptors

Figure 7:
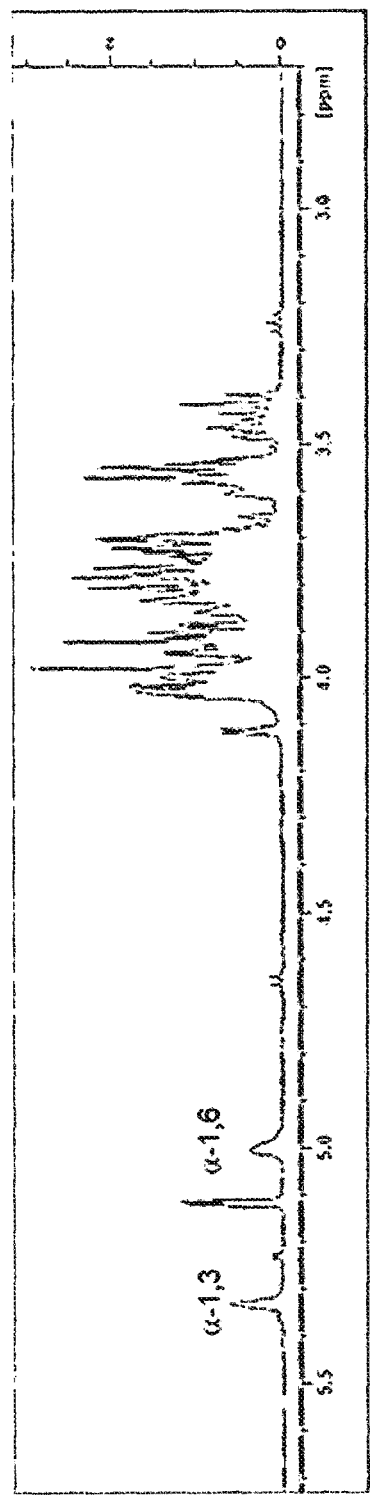
FIGS. 7 and 8 show an NMR spectrum.
Figure 8:
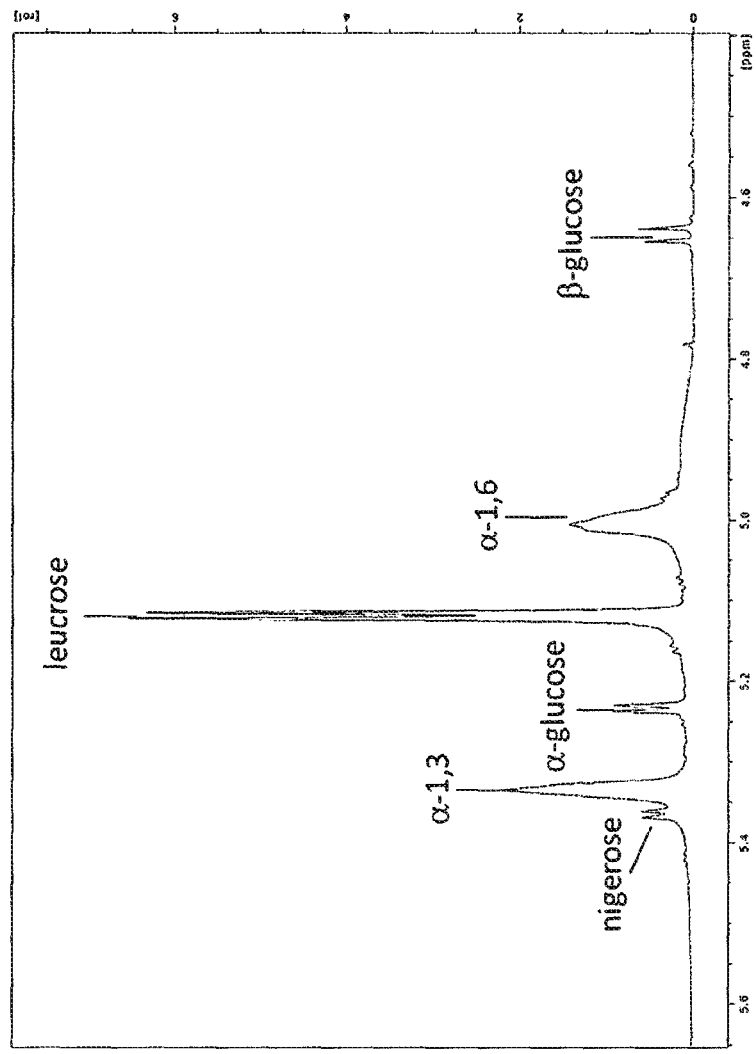

Moreover, the enzyme and its truncated form have proved capable of carrying out such connection reactions in α-1,3 over a wide range of higher molecular weight dextrans. Tests were performed out on particular dextran 68.4 kDa, 503 kDa and $2 \times 10^6$ Da. Based on proton NMR analyses, the high molecular weight dextrans have 50% of α-1,3 bonds (FIGS. 7 and 8). Here again we find the comb-like structure described in the '80s in the work on the native glucan produced by the strain.

FIGS. 7 and 8 show the NMR spectrum of dextran 68.4 kDa connected in α-1,3 obtained with the whole enzyme and the truncated enzyme respectively.

These results show that the α-1,3BrS is therefore able to recognise and connect many dextrans having a molecular weight between 1.5 and $2 \times 10^6$ kDa. We can therefore offer a range of products from small prebiotic gluco-oligosaccharides to high molecular weight polymers, with rates controlled (like) of connections in α-1,3.

Example 6

Identification of an Orthologue in *L. citreum*

With this characterisation, the inventors sought orthologues to this enzyme, which allowed identification of such an orthologue of this enzyme in the genome of the strain *L. citreum* LBAE E16 (SEQ ID NO: 13 and SEQ ID NO: 14 for the nucleic and protein sequences of this orthologue respectively).

A comparative analysis of the newly identified with the previous sequence has revealed that they share 98% identity for the complete sequence with an identity of 100% with respect to the patterns I to IV of the catalytic heart.

Example 7

Identification of an Ortholog in *L. fallax*

The identification of an orthologue opened the way to research on other orthologues in other species, which has allowed the inventors to identify at the strain KCTC 3537 *Leuconostoc fallax* a protein (SEQ ID NO: 16) having an overall identity of about 54% with the protein sequence of α-1,3 BrS, which rises to 68% when we focus on the catalytic domains A, B and C.

An analysis of the catalytic units I, II, III and IV shows a slight discrepancy regarding the pattern III In its implementation, the method is tested on a variable proportion of the two enzymes.

The products formed from the enzymatic reaction are analysed by chromatography (HPAEC-PAD, HPSEC to determine the size of the oligosaccharides produced) and NMR of the proton (determination of the proportion of α-1,3 bonds).

Example 9

Assessment of Physico-Chemical Properties of Very High Molecular Mass Glucans with Controlled Content of α-1,3 Bonds Different high molecular weight glucans are incubated in the presence of the α-1,3 BrS enzyme. The physicochemical properties of the resulting glucans are investigated, in particular by thermogravimetric analysis, by determining the glass transition temperature, and rheological analysis (see IRAGUE et al, *Biomacromolecules*, 2012).

Example 10

Assessment of Physico-Chemical Properties of Very High Molecular Mass Glucans with Controlled Content of α-1,2 and α-1.3 Bonds Different very high molecular mass glucans are incubated in the presence of the enzyme α-1,3 BrS and of the enzyme GBD-CD2 (BRISON and al., 2009) which shows a connecting activity in α-1,2. The physicochemical properties of

|  | Patter II (SEQ ID NO:) | Pattern III (SEQ ID NO:) | Pattern IV (SEQ ID NO:) | Pattern I (SEQ ID NO:) |
| --- | --- | --- | --- | --- |
| α-1,3 BrS | SMRIDAISFVD (18) | HISIVEAPKGE (19) | IVHAHDKDIQDTVIH (20) | ADFVANQ (17) |
| GH *L. fallax* | SIRIDAISFVD (22) | HVSIVEASADQ (23) | IVHAHDKDIQDAVSN (24) | ADYVANQ (21) |
| Identity (%) | 90 | 45.5 | 80 | 85 |

As above, the inventors conducted a cloning of this putative hydrolase glycoside and its recombinant expression in *E. coli*.

To do so, the inventors have previously made a synthetic gene (SEQ ID NO: 15) by codon optimisation of the wild-type gene, to facilitate recombinant expression of the protein in *E. coli* BL21 star DE3 as before. The production of the protein allowed to obtain an amount of protein for characterisation (output 2.5 times greater than that obtained for α-1,3 BrS).

Brought into contact with sucrose only, the enzyme revealed, as for the α-1,3 BrS, its inability to polymerise the glucosyl units. Now, as for the α-1,3 BrS, it showed its ability to make connections in α-1,3 on a dextran 1500 Da with a connection rate of 37%.

Example 8

Development of a Method in One Single Step for the Production of Oligosaccharides with Connections Controlled in α-1,3

This process involves the implementation of a polymerase of the family GH-70 coupled with the action of the enzyme α-1.3 BrS on sucrose alone.

the resulting glucans are investigated, in particular by thermogravimetric analysis, by determining the glass transition temperature, and rheological analysis (see IRAGUE et al, *Biomacromolecules*, 2012).

Example 11

Example 11

Assessment of Physico-Chemical and Prebiotic Properties of Oligosaccharides with a Controlled Content in α-1,2 and α-1.3 Bonds Isomaltooligosaccharides are incubated in the presence of the enzyme α-1,3 BrS and of the enzyme GBD-CD2 which shows a connecting activity in α-1,2. Prebiotics and physicochemical properties of the resulting glucans are investigated.

Example 12

Evaluation of the Prebiotic, Nutritional Properties and of the Metabolic Effects of Oligosaccharides Connected in α-1.3

These properties are tested for different oligosaccharides connected with the enzyme α-1,3 BrS.

Example 13

Screening of a Library Acceptor

The enzyme α-1,3 BrS is put in the presence of its natural substrate (sucrose) and a panel of different acceptors, including dextrans connected in α-1.2 (BRISON et al., 2009), of mutans, of alternans, of reuterans, of fructans and of fructooligosaccharides, of polyphenols, of flavonoids, of amino acids. The reaction products are analysed by various chromatographic techniques (mass spectrometry, HPAEC-PAD) and by NMR.

These experiments have already shown that this enzyme allows the glycosylation of oligosaccharides such as the fructoologosaccharides (FOS) and xylooligosaccharides (XOS)

Example 14

Screening of a Donor Library

The enzyme α-1,3 BrS is implemented on various analogues of sucrose (DAUDE et al, 2012) which can serve as donor of glucosyl units.

The invention claimed is:

1. Method for producing acceptors connected to glucosyl units in alpha 1,3 comprising a rate of connections of such glucosyl units in alpha 1,3 between 1 and 50%, said method comprising the steps of:
   (i) mixing in a reaction medium:
      an isolated polypeptide having the ability to specifically form connections of glucosyl units in alpha-1,3 on an acceptor having at least one hydroxyl moiety, said polypeptide having a sequence identity of at least 99% with SEQ ID NO:9, and wherein said polypeptide maintains an aspartic acid residue (D) at position 5 of the pattern II (SEQ ID NO: 2), a glutamic acid residue (E) at position 6 of the pattern III (SEQ ID NO: 3), and an aspartic acid residue (D) at position 6 of the pattern IV (SEQ ID NO: 4);
      a substrate of said polypeptide and;
      an acceptor comprising at least one hydroxyl moiety; and
   (ii) incubating said mixture obtained in step (i) so as to obtain connection of glucosyl units in alpha-1,3 on said acceptor,
      wherein the rate of connections of such glucosyl units in alpha 1,3 is controlled by varying the ratio between the substrate concentration and the acceptor concentration.

2. The method of claim 1, wherein the substrate is selected from the group consisting of α-D-glucopyranosyl fluoride, p-nitrophenyl α-D-glucopyranoside, α-D-glucopyranosyl, α-L-sorofuranoside, lactulosucrose and sucrose.

3. The method of claim 1, wherein the acceptor comprising at least one hydroxyl moiety is a thickener, an emulsifier, a texturing agent and/or a stabilizer.

* * * * *

```
                      SEQUENCE LISTING

<160> NUMBER OF SEQ ID NOS: 24

<210> SEQ ID NO 1
<211> LENGTH: 7
<212> TYPE: PRT
<213> ORGANISM: Artificial Sequence
<220> FEATURE:
<223> OTHER INFORMATION: enzymatic domain
<220> FEATURE:
<221> NAME/KEY: MISC_FEATURE
<222> LOCATION: (3)..(3)
<223> OTHER INFORMATION: X= F or Y

<400> SEQUENCE: 1

Ala Asp Xaa Val Ala Asn Gln
1               5

<210> SEQ ID NO 2
<211> LENGTH: 11
<212> TYPE: PRT
<213> ORGANISM: Artificial Sequence
<220> FEATURE:
<223> OTHER INFORMATION: enzymatic domain
<220> FEATURE:
<221> NAME/KEY: MISC_FEATURE
<222> LOCATION: (2)..(2)
<223> OTHER INFORMATION: X= M or I

<400> SEQUENCE: 2

Ser Xaa Arg Ile Asp Ala Ile Ser Phe Val Asp
1               5                   10

<210> SEQ ID NO 3
<211> LENGTH: 11
<212> TYPE: PRT
<213> ORGANISM: Artificial Sequence
<220> FEATURE:
<223> OTHER INFORMATION: enzymatic domain
<220> FEATURE:
<221> NAME/KEY: MISC_FEATURE
<222> LOCATION: (2)..(2)
<223> OTHER INFORMATION: X= I or V
<220> FEATURE:
<221> NAME/KEY: MISC_FEATURE
<222> LOCATION: (8)..(8)
<223> OTHER INFORMATION: X= P or S
<220> FEATURE:
<221> NAME/KEY: MISC_FEATURE
<222> LOCATION: (9)..(9)
<223> OTHER INFORMATION: X= K or A
<220> FEATURE:
<221> NAME/KEY: MISC_FEATURE
<222> LOCATION: (10)..(10)
<223> OTHER INFORMATION: X= G or D
<220> FEATURE:
<221> NAME/KEY: MISC_FEATURE
<222> LOCATION: (11)..(11)
<223> OTHER INFORMATION: X= E or Q
```

-continued

<400> SEQUENCE: 3

His Xaa Ser Ile Val Glu Ala Xaa Xaa Xaa Xaa
1               5                   10

<210> SEQ ID NO 4
<211> LENGTH: 15
<212> TYPE: PRT
<213> ORGANISM: Artificial Sequence
<220> FEATURE:
<223> OTHER INFORMATION: enzymatic domain
<220> FEATURE:
<221> NAME/KEY: MISC_FEATURE
<222> LOCATION: (12)..(12)
<223> OTHER INFORMATION: X= T or A
<220> FEATURE:
<221> NAME/KEY: MISC_FEATURE
<222> LOCATION: (14)..(14)
<223> OTHER INFORMATION: X= I or S
<220> FEATURE:
<221> NAME/KEY: MISC_FEATURE
<222> LOCATION: (15)..(15)
<223> OTHER INFORMATION: X= H or N

<400> SEQUENCE: 4

Ile Val His Ala His Asp Lys Asp Ile Gln Asp Xaa Val Xaa Xaa
1               5                   10                  15

<210> SEQ ID NO 5
<211> LENGTH: 635
<212> TYPE: PRT
<213> ORGANISM: Artificial Sequence
<220> FEATURE:
<223> OTHER INFORMATION: structural domain

<400> SEQUENCE: 5

Asn Pro Val Val Gln Ala Glu Gln Leu Asn Trp Leu Tyr Tyr Leu Met
1               5                   10                  15

Asn Phe Gly Gln Ile Thr Ala Asn Asp Ser Asn Ala Asn Phe Asp Ser
                20                  25                  30

Met Arg Ile Asp Ala Ile Ser Phe Val Asp Pro Gln Ile Ala Lys Lys
            35                  40                  45

Ala Tyr Asp Leu Leu Asp Lys Met Tyr Gly Leu Thr Asp Asn Glu Ala
        50                  55                  60

Val Ala Asn Gln His Ile Ser Ile Val Glu Ala Pro Lys Gly Glu Thr
65                  70                  75                  80

Pro Ile Thr Val Glu Lys Gln Ser Ala Leu Val Glu Ser Asn Trp Arg
                85                  90                  95

Asp Arg Met Lys Gln Ser Leu Ser Lys Asn Ala Thr Leu Asp Lys Leu
            100                 105                 110

Asp Pro Asp Pro Ala Ile Asn Ser Leu Glu Lys Leu Val Ala Asp Asp
        115                 120                 125

Leu Val Asn Arg Ser Gln Ser Ser Asp Lys Asp Ser Ser Thr Ile Pro
130                 135                 140

Asn Tyr Ser Ile Val His Ala His Asp Lys Asp Ile Gln Asp Thr Val
145                 150                 155                 160

Ile His Ile Met Lys Ile Val Asn Asn Pro Asn Ile Ser Met Ser
                165                 170                 175

Asp Phe Thr Met Gln Gln Leu Gln Asn Gly Leu Lys Ala Phe Tyr Glu
            180                 185                 190

Asp Gln His Gln Ser Val Lys Lys Tyr Asn Gln Tyr Asn Ile Pro Ser
        195                 200                 205

```
Ala Tyr Ala Leu Leu Leu Thr Asn Lys Asp Thr Val Pro Arg Val Phe
    210                 215                 220
Tyr Gly Asp Met Tyr Gln Asp Tyr Gly Asp Asp Leu Asp Gly Gly Gln
225                 230                 235                 240
Tyr Met Ala Thr Lys Ser Ile Tyr Tyr Asn Ala Ile Glu Gln Met Met
            245                 250                 255
Lys Ala Arg Leu Lys Tyr Val Ala Gly Gly Gln Ile Met Ala Val Thr
        260                 265                 270
Lys Ile Lys Asn Asp Gly Ile Asn Lys Asp Gly Thr Asn Lys Ser Gly
    275                 280                 285
Glu Val Leu Thr Ser Val Arg Phe Gly Lys Asp Ile Met Asp Ala Gln
    290                 295                 300
Gly Gln Gly Thr Ala Glu Ser Arg Asn Gln Gly Ile Gly Val Ile Val
305                 310                 315                 320
Ser Asn Ser Ser Gly Leu Glu Leu Lys Asn Ser Asp Ser Ile Thr Leu
            325                 330                 335
His Met Gly Ile Ala His Lys Asn Gln Ala Tyr Arg Ala Leu Met Leu
        340                 345                 350
Thr Asn Asp Lys Gly Ile Val Asn Tyr Asp Gln Asp Asn Asn Ala Pro
    355                 360                 365
Ile Ala Trp Thr Asn Asp His Gly Asp Leu Ile Phe Thr Asn Gln Met
    370                 375                 380
Ile Asn Gly Gln Ser Asp Thr Ala Val Lys Gly Tyr Leu Asn Pro Glu
385                 390                 395                 400
Val Ala Gly Tyr Leu Ala Val Trp Val Pro Val Gly Ala Asn Asp Asn
            405                 410                 415
Gln Asp Ala Arg Thr Val Thr Thr Asn Gln Lys Asn Thr Asp Gly Lys
        420                 425                 430
Val Leu His Thr Asn Ala Ala Leu Asp Ser Lys Leu Met Tyr Glu Gly
    435                 440                 445
Phe Ser Asn Phe Gln Lys Met Pro Thr Arg Gly Asn Gln Tyr Ala Asn
    450                 455                 460
Val Val Ile Thr Lys Asn Ile Asp Leu Phe Lys Ser Trp Gly Ile Thr
465                 470                 475                 480
Asp Phe Glu Leu Ala Pro Gln Tyr Arg Ser Ser Asp Gly Lys Asp Ile
            485                 490                 495
Thr Asp Arg Phe Leu Asp Ser Ile Val Gln Asn Gly Tyr Gly Leu Ser
        500                 505                 510
Asp Arg Tyr Asp Leu Gly Phe Lys Thr Pro Thr Lys Tyr Gly Thr Asp
    515                 520                 525
Gln Asp Leu Arg Lys Ala Ile Glu Arg Leu His Gln Ala Gly Met Ser
    530                 535                 540
Val Met Ala Asp Phe Val Ala Asn Gln Ile Tyr Gly Leu His Ala Asp
545                 550                 555                 560
Lys Glu Val Val Ser Ala Gln His Val Asn Ile Asn Gly Asp Thr Lys
            565                 570                 575
Leu Val Val Asp Pro Arg Tyr Gly Thr Gln Met Thr Val Val Asn Ser
        580                 585                 590
Val Gly Gly Gly Asp Tyr Gln Ala Lys Tyr Gly Gly Glu Tyr Leu Asp
    595                 600                 605
Thr Ile Ser Lys Leu Tyr Pro Gly Leu Leu Asp Ser Asn Gly Gln
    610                 615                 620
```

```
Lys Ile Asp Leu Ser Thr Lys Ile Lys Glu Trp
625                 630                 635
```

<210> SEQ ID NO 6
<211> LENGTH: 699
<212> TYPE: PRT
<213> ORGANISM: Artificial Sequence
<220> FEATURE:
<223> OTHER INFORMATION: structural domain

<400> SEQUENCE: 6

```
Asn Val Asp Ser Glu Tyr Pro Gly Gly Trp Phe Gln Gly Gly Tyr Leu
1               5                   10                  15

Ala Tyr Gln Asn Ser Asp Leu Thr Pro Tyr Ala Asn Thr Asn Pro Asp
            20                  25                  30

Tyr Arg Thr His Asn Gly Leu Glu Phe Leu Leu Ala Asn Asp Val Asp
                35                  40                  45

Asn Ser Asn Pro Val Val Gln Ala Glu Gln Leu Asn Trp Leu Tyr Tyr
        50                  55                  60

Leu Met Asn Phe Gly Gln Ile Thr Ala Asn Asp Ser Asn Ala Asn Phe
65                  70                  75                  80

Asp Ser Met Arg Ile Asp Ala Ile Ser Phe Val Asp Pro Gln Ile Ala
                85                  90                  95

Lys Lys Ala Tyr Asp Leu Leu Asp Lys Met Tyr Gly Leu Thr Asp Asn
            100                 105                 110

Glu Ala Val Ala Asn Gln His Ile Ser Ile Val Glu Ala Pro Lys Gly
                115                 120                 125

Glu Thr Pro Ile Thr Val Glu Lys Gln Ser Ala Leu Val Glu Ser Asn
        130                 135                 140

Trp Arg Asp Arg Met Lys Gln Ser Leu Ser Lys Asn Ala Thr Leu Asp
145                 150                 155                 160

Lys Leu Asp Pro Asp Pro Ala Ile Asn Ser Leu Glu Lys Leu Val Ala
                165                 170                 175

Asp Asp Leu Val Asn Arg Ser Gln Ser Ser Asp Lys Asp Ser Ser Thr
            180                 185                 190

Ile Pro Asn Tyr Ser Ile Val His Ala His Asp Lys Asp Ile Gln Asp
                195                 200                 205

Thr Val Ile His Ile Met Lys Ile Val Asn Asn Pro Asn Ile Ser
        210                 215                 220

Met Ser Asp Phe Thr Met Gln Gln Leu Gln Asn Gly Leu Lys Ala Phe
225                 230                 235                 240

Tyr Glu Asp Gln His Gln Ser Val Lys Lys Tyr Asn Gln Tyr Asn Ile
                245                 250                 255

Pro Ser Ala Tyr Ala Leu Leu Leu Thr Asn Lys Asp Thr Val Pro Arg
            260                 265                 270

Val Phe Tyr Gly Asp Met Tyr Gln Asp Tyr Gly Asp Asp Leu Asp Gly
                275                 280                 285

Gly Gln Tyr Met Ala Thr Lys Ser Ile Tyr Tyr Asn Ala Ile Glu Gln
        290                 295                 300

Met Met Lys Ala Arg Leu Lys Tyr Val Ala Gly Gly Gln Ile Met Ala
305                 310                 315                 320

Val Thr Lys Ile Lys Asn Asp Gly Ile Asn Lys Asp Gly Thr Asn Lys
                325                 330                 335

Ser Gly Glu Val Leu Thr Ser Val Arg Phe Gly Lys Asp Ile Met Asp
            340                 345                 350
```

Ala Gln Gly Gln Gly Thr Ala Glu Ser Arg Asn Gln Gly Ile Gly Val
            355                 360                 365

Ile Val Ser Asn Ser Ser Gly Leu Glu Leu Lys Asn Ser Asp Ser Ile
    370                 375                 380

Thr Leu His Met Gly Ile Ala His Lys Asn Gln Ala Tyr Arg Ala Leu
385                 390                 395                 400

Met Leu Thr Asn Asp Lys Gly Ile Val Asn Tyr Asp Gln Asp Asn Asn
            405                 410                 415

Ala Pro Ile Ala Trp Thr Asn Asp His Gly Asp Leu Ile Phe Thr Asn
            420                 425                 430

Gln Met Ile Asn Gly Gln Ser Asp Thr Ala Val Lys Gly Tyr Leu Asn
            435                 440                 445

Pro Glu Val Ala Gly Tyr Leu Ala Val Trp Val Pro Val Gly Ala Asn
            450                 455                 460

Asp Asn Gln Asp Ala Arg Thr Val Thr Thr Asn Gln Lys Asn Thr Asp
465                 470                 475                 480

Gly Lys Val Leu His Thr Asn Ala Ala Leu Asp Ser Lys Leu Met Tyr
            485                 490                 495

Glu Gly Phe Ser Asn Phe Gln Lys Met Pro Thr Arg Gly Asn Gln Tyr
            500                 505                 510

Ala Asn Val Val Ile Thr Lys Asn Ile Asp Leu Phe Lys Ser Trp Gly
            515                 520                 525

Ile Thr Asp Phe Glu Leu Ala Pro Gln Tyr Arg Ser Ser Asp Gly Lys
            530                 535                 540

Asp Ile Thr Asp Arg Phe Leu Asp Ser Ile Val Gln Asn Gly Tyr Gly
545                 550                 555                 560

Leu Ser Asp Arg Tyr Asp Leu Gly Phe Lys Thr Pro Thr Lys Tyr Gly
            565                 570                 575

Thr Asp Gln Asp Leu Arg Lys Ala Ile Glu Arg Leu His Gln Ala Gly
            580                 585                 590

Met Ser Val Met Ala Asp Phe Val Ala Asn Gln Ile Tyr Gly Leu His
            595                 600                 605

Ala Asp Lys Glu Val Val Ser Ala Gln His Val Asn Ile Asn Gly Asp
            610                 615                 620

Thr Lys Leu Val Val Asp Pro Arg Tyr Gly Thr Gln Met Thr Val Val
625                 630                 635                 640

Asn Ser Val Gly Gly Gly Asp Tyr Gln Ala Lys Tyr Gly Gly Glu Tyr
            645                 650                 655

Leu Asp Thr Ile Ser Lys Leu Tyr Pro Gly Leu Leu Leu Asp Ser Asn
            660                 665                 670

Gly Gln Lys Ile Asp Leu Ser Thr Lys Ile Lys Glu Trp Ser Ala Lys
            675                 680                 685

Tyr Leu Asn Gly Ser Asn Ile Pro Gln Val Gly
            690                 695

<210> SEQ ID NO 7
<211> LENGTH: 911
<212> TYPE: PRT
<213> ORGANISM: Artificial Sequence
<220> FEATURE:
<223> OTHER INFORMATION: structural domain

<400> SEQUENCE: 7

Val Lys Asp Val Tyr Ser Gln His Asn Ala Val Asn Asn Leu Ser Ala
1               5                   10                  15

```
Asn Asn Phe Lys Asn Leu Val Asp Gly Phe Leu Thr Ala Glu Thr Trp
            20                  25                  30

Tyr Arg Pro Ala Gln Ile Leu Ser His Gly Thr Asp Trp Val Ala Ser
        35                  40                  45

Thr Asp Lys Asp Phe Arg Pro Leu Ile Thr Val Trp Trp Pro Asn Lys
    50                  55                  60

Asp Ile Gln Val Asn Tyr Leu Lys Leu Met Gln Gln Ile Gly Ile Leu
65                  70                  75                  80

Asp Asn Ser Val Val Phe Asp Thr Asn Asn Asp Gln Leu Val Leu Asn
                85                  90                  95

Lys Gly Ala Glu Ser Ala Gln Ile Gly Ile Glu Lys Lys Val Ser Glu
            100                 105                 110

Thr Gly Asn Thr Asp Trp Leu Asn Glu Leu Leu Phe Ala Pro Asn Gly
        115                 120                 125

Asn Gln Pro Ser Phe Ile Lys Gln Gln Tyr Leu Trp Asn Val Asp Ser
    130                 135                 140

Glu Tyr Pro Gly Gly Trp Phe Gln Gly Gly Tyr Leu Ala Tyr Gln Asn
145                 150                 155                 160

Ser Asp Leu Thr Pro Tyr Ala Asn Thr Asn Pro Asp Tyr Arg Thr His
                165                 170                 175

Asn Gly Leu Glu Phe Leu Leu Ala Asn Asp Val Asp Asn Ser Asn Pro
            180                 185                 190

Val Val Gln Ala Glu Gln Leu Asn Trp Leu Tyr Tyr Leu Met Asn Phe
        195                 200                 205

Gly Gln Ile Thr Ala Asn Asp Ser Asn Ala Asn Phe Asp Ser Met Arg
    210                 215                 220

Ile Asp Ala Ile Ser Phe Val Asp Pro Gln Ile Ala Lys Lys Ala Tyr
225                 230                 235                 240

Asp Leu Leu Asp Lys Met Tyr Gly Leu Thr Asp Asn Glu Ala Val Ala
                245                 250                 255

Asn Gln His Ile Ser Ile Val Glu Ala Pro Lys Gly Glu Thr Pro Ile
            260                 265                 270

Thr Val Glu Lys Gln Ser Ala Leu Val Glu Ser Asn Trp Arg Asp Arg
        275                 280                 285

Met Lys Gln Ser Leu Ser Lys Asn Ala Thr Leu Asp Lys Leu Asp Pro
    290                 295                 300

Asp Pro Ala Ile Asn Ser Leu Glu Lys Leu Val Ala Asp Asp Leu Val
305                 310                 315                 320

Asn Arg Ser Gln Ser Ser Asp Lys Asp Ser Thr Ile Pro Asn Tyr
                325                 330                 335

Ser Ile Val His Ala His Asp Lys Asp Ile Gln Asp Thr Val Ile His
                340                 345                 350

Ile Met Lys Ile Val Asn Asn Pro Asn Ile Ser Met Ser Asp Phe
            355                 360                 365

Thr Met Gln Gln Leu Gln Asn Gly Leu Lys Ala Phe Tyr Glu Asp Gln
        370                 375                 380

His Gln Ser Val Lys Lys Tyr Asn Gln Tyr Asn Ile Pro Ser Ala Tyr
385                 390                 395                 400

Ala Leu Leu Leu Thr Asn Lys Asp Thr Val Pro Arg Val Phe Tyr Gly
                405                 410                 415

Asp Met Tyr Gln Asp Tyr Gly Asp Asp Leu Asp Gly Gly Gln Tyr Met
                420                 425                 430

Ala Thr Lys Ser Ile Tyr Tyr Asn Ala Ile Glu Gln Met Met Lys Ala
```

-continued

```
            435                 440                 445
Arg Leu Lys Tyr Val Ala Gly Gln Ile Met Ala Val Thr Lys Ile
            450                 455                 460
Lys Asn Asp Gly Ile Asn Lys Asp Gly Thr Asn Lys Ser Gly Glu Val
465                 470                 475                 480
Leu Thr Ser Val Arg Phe Gly Lys Asp Ile Met Asp Ala Gln Gly Gln
                    485                 490                 495
Gly Thr Ala Glu Ser Arg Asn Gln Gly Ile Gly Val Ile Val Ser Asn
            500                 505                 510
Ser Ser Gly Leu Glu Leu Lys Asn Ser Asp Ser Ile Thr Leu His Met
            515                 520                 525
Gly Ile Ala His Lys Asn Gln Ala Tyr Arg Ala Leu Met Leu Thr Asn
            530                 535                 540
Asp Lys Gly Ile Val Asn Tyr Asp Gln Asp Asn Asn Ala Pro Ile Ala
545                 550                 555                 560
Trp Thr Asn Asp His Gly Asp Leu Ile Phe Thr Asn Gln Met Ile Asn
                    565                 570                 575
Gly Gln Ser Asp Thr Ala Val Lys Gly Tyr Leu Asn Pro Glu Val Ala
            580                 585                 590
Gly Tyr Leu Ala Val Trp Val Pro Val Gly Ala Asn Asp Asn Gln Asp
            595                 600                 605
Ala Arg Thr Val Thr Thr Asn Gln Lys Asn Thr Asp Gly Lys Val Leu
            610                 615                 620
His Thr Asn Ala Ala Leu Asp Ser Lys Leu Met Tyr Glu Gly Phe Ser
625                 630                 635                 640
Asn Phe Gln Lys Met Pro Thr Arg Gly Asn Gln Tyr Ala Asn Val Val
                    645                 650                 655
Ile Thr Lys Asn Ile Asp Leu Phe Lys Ser Trp Gly Ile Thr Asp Phe
            660                 665                 670
Glu Leu Ala Pro Gln Tyr Arg Ser Ser Asp Gly Lys Asp Ile Thr Asp
            675                 680                 685
Arg Phe Leu Asp Ser Ile Val Gln Asn Gly Tyr Gly Leu Ser Asp Arg
            690                 695                 700
Tyr Asp Leu Gly Phe Lys Thr Pro Thr Lys Tyr Gly Thr Asp Gln Asp
705                 710                 715                 720
Leu Arg Lys Ala Ile Glu Arg Leu His Gln Ala Gly Met Ser Val Met
                    725                 730                 735
Ala Asp Phe Val Ala Asn Gln Ile Tyr Gly Leu His Ala Asp Lys Glu
                    740                 745                 750
Val Val Ser Ala Gln His Val Asn Ile Asn Gly Asp Thr Lys Leu Val
            755                 760                 765
Val Asp Pro Arg Tyr Gly Thr Gln Met Thr Val Val Asn Ser Val Gly
            770                 775                 780
Gly Gly Asp Tyr Gln Ala Lys Tyr Gly Gly Glu Tyr Leu Asp Thr Ile
785                 790                 795                 800
Ser Lys Leu Tyr Pro Gly Leu Leu Asp Ser Asn Gly Gln Lys Ile
                    805                 810                 815
Asp Leu Ser Thr Lys Ile Lys Glu Trp Ser Ala Lys Tyr Leu Asn Gly
                    820                 825                 830
Ser Asn Ile Pro Gln Val Gly Met Gly Tyr Val Leu Lys Asp Trp Asn
            835                 840                 845
Asn Gly Gln Tyr Phe His Ile Leu Asp Lys Glu Gly Gln Tyr Ser Leu
            850                 855                 860
```

```
Pro Thr Gln Leu Val Ser Asn Asp Pro Glu Thr Gln Ile Gly Glu Ser
865                 870                 875                 880

Val Asn Tyr Lys Tyr Phe Ile Gly Asn Ser Asp Ala Thr Tyr Asn Met
            885                 890                 895

Tyr His Asn Leu Pro Asn Thr Val Ser Leu Ile Asn Ser Gln Glu
            900                 905                 910
```

<210> SEQ ID NO 8
<211> LENGTH: 1204
<212> TYPE: PRT
<213> ORGANISM: Artificial Sequence
<220> FEATURE:
<223> OTHER INFORMATION: structural domain

<400> SEQUENCE: 8

```
Leu Asn Tyr Phe Asp Leu Ala Thr Gly Ile Gln Leu Lys Gly Gln Ala
1               5                   10                  15

Lys Asn Ile Asp Gly Ile Gly Tyr Tyr Phe Asp Gln Asn Asn Gly Asn
            20                  25                  30

Gly Glu Tyr Arg Tyr Ser Leu Thr Gly Pro Val Val Lys Asp Val Tyr
        35                  40                  45

Ser Gln His Asn Ala Val Asn Asn Leu Ser Ala Asn Asn Phe Lys Asn
50                  55                  60

Leu Val Asp Gly Phe Leu Thr Ala Glu Thr Trp Tyr Arg Pro Ala Gln
65                  70                  75                  80

Ile Leu Ser His Gly Thr Asp Trp Val Ala Ser Thr Asp Lys Asp Phe
                85                  90                  95

Arg Pro Leu Ile Thr Val Trp Trp Pro Asn Lys Asp Ile Gln Val Asn
            100                 105                 110

Tyr Leu Lys Leu Met Gln Gln Ile Gly Ile Leu Asp Asn Ser Val Val
            115                 120                 125

Phe Asp Thr Asn Asn Asp Gln Leu Val Leu Asn Lys Gly Ala Glu Ser
130                 135                 140

Ala Gln Ile Gly Ile Glu Lys Lys Val Ser Glu Thr Gly Asn Thr Asp
145                 150                 155                 160

Trp Leu Asn Glu Leu Leu Phe Ala Pro Asn Gly Asn Gln Pro Ser Phe
                165                 170                 175

Ile Lys Gln Gln Tyr Leu Trp Asn Val Asp Ser Glu Tyr Pro Gly Gly
            180                 185                 190

Trp Phe Gln Gly Gly Tyr Leu Ala Tyr Gln Asn Ser Asp Leu Thr Pro
        195                 200                 205

Tyr Ala Asn Thr Asn Pro Asp Tyr Arg Thr His Asn Gly Leu Glu Phe
210                 215                 220

Leu Leu Ala Asn Asp Val Asp Asn Ser Asn Pro Val Val Gln Ala Glu
225                 230                 235                 240

Gln Leu Asn Trp Leu Tyr Tyr Leu Met Asn Phe Gly Gln Ile Thr Ala
                245                 250                 255

Asn Asp Ser Asn Ala Asn Phe Asp Ser Met Arg Ile Asp Ala Ile Ser
            260                 265                 270

Phe Val Asp Pro Gln Ile Ala Lys Lys Ala Tyr Asp Leu Leu Asp Lys
            275                 280                 285

Met Tyr Gly Leu Thr Asp Asn Glu Ala Val Ala Asn Gln His Ile Ser
        290                 295                 300

Ile Val Glu Ala Pro Lys Gly Glu Thr Pro Ile Thr Val Glu Lys Gln
305                 310                 315                 320
```

-continued

Ser Ala Leu Val Glu Ser Asn Trp Arg Asp Arg Met Lys Gln Ser Leu
            325                 330                 335

Ser Lys Asn Ala Thr Leu Asp Lys Leu Asp Pro Asp Pro Ala Ile Asn
        340                 345                 350

Ser Leu Glu Lys Leu Val Ala Asp Asp Leu Val Asn Arg Ser Gln Ser
            355                 360                 365

Ser Asp Lys Asp Ser Ser Thr Ile Pro Asn Tyr Ser Ile Val His Ala
    370                 375                 380

His Asp Lys Asp Ile Gln Asp Thr Val Ile His Ile Met Lys Ile Val
385                 390                 395                 400

Asn Asn Asn Pro Asn Ile Ser Met Ser Asp Phe Thr Met Gln Gln Leu
                405                 410                 415

Gln Asn Gly Leu Lys Ala Phe Tyr Glu Asp Gln His Gln Ser Val Lys
            420                 425                 430

Lys Tyr Asn Gln Tyr Asn Ile Pro Ser Ala Tyr Ala Leu Leu Leu Thr
        435                 440                 445

Asn Lys Asp Thr Val Pro Arg Val Phe Tyr Gly Asp Met Tyr Gln Asp
    450                 455                 460

Tyr Gly Asp Asp Leu Asp Gly Gly Gln Tyr Met Ala Thr Lys Ser Ile
465                 470                 475                 480

Tyr Tyr Asn Ala Ile Glu Gln Met Met Lys Ala Arg Leu Lys Tyr Val
                485                 490                 495

Ala Gly Gly Gln Ile Met Ala Val Thr Lys Ile Lys Asn Asp Gly Ile
            500                 505                 510

Asn Lys Asp Gly Thr Asn Lys Ser Gly Glu Val Leu Thr Ser Val Arg
        515                 520                 525

Phe Gly Lys Asp Ile Met Asp Ala Gln Gly Gln Gly Thr Ala Glu Ser
    530                 535                 540

Arg Asn Gln Gly Ile Gly Val Ile Val Ser Asn Ser Ser Gly Leu Glu
545                 550                 555                 560

Leu Lys Asn Ser Asp Ser Ile Thr Leu His Met Gly Ile Ala His Lys
                565                 570                 575

Asn Gln Ala Tyr Arg Ala Leu Met Leu Thr Asn Asp Lys Gly Ile Val
            580                 585                 590

Asn Tyr Asp Gln Asp Asn Asn Ala Pro Ile Ala Trp Thr Asn Asp His
        595                 600                 605

Gly Asp Leu Ile Phe Thr Asn Gln Met Ile Asn Gly Gln Ser Asp Thr
    610                 615                 620

Ala Val Lys Gly Tyr Leu Asn Pro Glu Val Ala Gly Tyr Leu Ala Val
625                 630                 635                 640

Trp Val Pro Val Gly Ala Asn Asp Asn Gln Asp Ala Arg Thr Val Thr
                645                 650                 655

Thr Asn Gln Lys Asn Thr Asp Gly Lys Val Leu His Thr Asn Ala Ala
            660                 665                 670

Leu Asp Ser Lys Leu Met Tyr Glu Gly Phe Ser Asn Phe Gln Lys Met
        675                 680                 685

Pro Thr Arg Gly Asn Gln Tyr Ala Asn Val Val Ile Thr Lys Asn Ile
    690                 695                 700

Asp Leu Phe Lys Ser Trp Gly Ile Thr Asp Phe Glu Leu Ala Pro Gln
705                 710                 715                 720

Tyr Arg Ser Ser Asp Gly Lys Asp Ile Thr Asp Arg Phe Leu Asp Ser
                725                 730                 735

```
Ile Val Gln Asn Gly Tyr Gly Leu Ser Asp Arg Tyr Asp Leu Gly Phe
            740                 745                 750

Lys Thr Pro Thr Lys Tyr Gly Thr Asp Gln Asp Leu Arg Lys Ala Ile
            755                 760                 765

Glu Arg Leu His Gln Ala Gly Met Ser Val Met Ala Asp Phe Val Ala
            770                 775                 780

Asn Gln Ile Tyr Gly Leu His Ala Asp Lys Glu Val Val Ser Ala Gln
785                 790                 795                 800

His Val Asn Ile Asn Gly Asp Thr Lys Leu Val Val Asp Pro Arg Tyr
                805                 810                 815

Gly Thr Gln Met Thr Val Val Asn Ser Val Gly Gly Asp Tyr Gln
            820                 825                 830

Ala Lys Tyr Gly Gly Glu Tyr Leu Asp Thr Ile Ser Lys Leu Tyr Pro
            835                 840                 845

Gly Leu Leu Asp Ser Asn Gly Gln Lys Ile Asp Leu Ser Thr Lys
            850                 855                 860

Ile Lys Glu Trp Ser Ala Lys Tyr Leu Asn Gly Ser Asn Ile Pro Gln
865                 870                 875                 880

Val Gly Met Gly Tyr Val Leu Lys Asp Trp Asn Asn Gly Gln Tyr Phe
                885                 890                 895

His Ile Leu Asp Lys Glu Gly Gln Tyr Ser Leu Pro Thr Gln Leu Val
                900                 905                 910

Ser Asn Asp Pro Glu Thr Gln Ile Gly Glu Ser Val Asn Tyr Lys Tyr
                915                 920                 925

Phe Ile Gly Asn Ser Asp Ala Thr Tyr Asn Met Tyr His Asn Leu Pro
            930                 935                 940

Asn Thr Val Ser Leu Ile Asn Ser Gln Glu Gly Gln Ile Lys Thr Gln
945                 950                 955                 960

Gln Ser Gly Val Thr Ser Asp Tyr Glu Gly Gln Val Gln Val Thr
                965                 970                 975

Arg Gln Tyr Thr Asp Ser Lys Gly Val Ser Trp Asn Leu Ile Thr Phe
            980                 985                 990

Ala Gly Gly Asp Leu Gln Gly Gln  Lys Leu Trp Val Asp  Ser Arg Ala
            995                 1000                1005

Leu Thr  Met Thr Pro Phe Lys  Thr Met Asn Gln Ile  Ser Phe Ile
        1010                1015                1020

Ser Tyr  Ala Asn Arg Asn Asp  Gly Leu Phe Leu Asn  Ala Pro Tyr
        1025                1030                1035

Gln Val  Lys Gly Tyr Gln Leu  Ala Gly Met Ser Asn  Gln Tyr Lys
        1040                1045                1050

Gly Gln  Gln Val Thr Ile Ala  Gly Val Ala Asn Val  Ser Gly Lys
        1055                1060                1065

Asp Trp  Ser Leu Ile Ser Phe  Asn Gly Thr Gln Tyr  Trp Ile Asp
        1070                1075                1080

Ser Gln  Ala Leu Asn Thr Asn  Phe Thr His Asp Met  Asn Gln Lys
        1085                1090                1095

Val Phe  Val Asn Thr Thr Ser  Asn Leu Asp Gly Leu  Phe Leu Asn
        1100                1105                1110

Ala Pro  Tyr Arg Gln Pro Gly  Tyr Lys Leu Ala Gly  Leu Ala Lys
        1115                1120                1125

Asn Tyr  Asn Asn Gln Thr Val  Thr Val Ser Gln Gln  Tyr Phe Asp
        1130                1135                1140

Asp Gln  Gly Thr Val Trp Ser  Glu Val Val Leu Gly  Gly Gln Thr
```

-continued

```
           1145                1150                1155
Val Trp Val Asp Asn His Ala Leu Ala Gln Met Gln Val Ser Asp
           1160                1165                1170
Thr Ser Gln Gln Leu Tyr Val Asn Ser Asn Gly Arg Asn Asp Gly
           1175                1180                1185
Leu Phe Leu Asn Ala Pro Tyr Arg Gly Gln Gly Ser Gln Leu Ile
           1190                1195                1200
Gly

<210> SEQ ID NO 9
<211> LENGTH: 1888
<212> TYPE: PRT
<213> ORGANISM: Leuconostoc citreum

<400> SEQUENCE: 9

Met Glu Met Lys Glu Thr Ile Thr Arg Lys Lys Leu Tyr Lys Ser Gly
1               5                   10                  15
Lys Ser Trp Val Ala Ala Thr Ala Phe Ala Val Met Gly Val Ser
            20                  25                  30
Ala Val Thr Thr Val Ser Ala Asp Thr Gln Thr Pro Val Gly Thr Thr
            35                  40                  45
Gln Ser Gln Gln Asp Leu Thr Gly Gln Thr Gly Gln Asp Lys Pro Thr
        50                  55                  60
Thr Lys Glu Val Ile Asp Lys Lys Glu Pro Val Pro Gln Val Ser Ala
65                  70                  75                  80
Gln Asn Val Gly Asp Leu Ser Ala Asp Ala Lys Thr Pro Lys Ala Asp
                85                  90                  95
Asp Lys Gln Asp Thr Gln Pro Thr Asn Ala Gln Leu Pro Asp Gln Gly
            100                 105                 110
Asn Lys Gln Thr Asn Ser Asn Ser Asp Lys Gly Val Lys Glu Ser Thr
        115                 120                 125
Thr Ala Pro Val Lys Thr Thr Asp Val Pro Ser Lys Ser Val Ala Pro
    130                 135                 140
Glu Thr Asn Thr Ser Ile Asn Gly Gly Gln Tyr Val Glu Lys Asp Gly
145                 150                 155                 160
Gln Phe Val Tyr Ile Asp Gln Ser Gly Lys Gln Val Ser Gly Leu Gln
                165                 170                 175
Asn Ile Glu Gly His Thr Gln Tyr Phe Asp Pro Lys Thr Gly Tyr Gln
            180                 185                 190
Thr Lys Gly Glu Leu Lys Asn Ile Asp Asp Asn Ala Tyr Tyr Phe Asp
        195                 200                 205
Lys Asn Ser Gly Asn Gly Arg Thr Phe Thr Lys Ile Ser Asn Gly Ser
    210                 215                 220
Tyr Ser Glu Lys Asp Gly Met Trp Gln Tyr Val Asp Ser His Asp Lys
225                 230                 235                 240
Gln Pro Val Lys Gly Leu Tyr Asp Val Glu Gly Asn Leu Gln Tyr Phe
                245                 250                 255
Asp Leu Ser Thr Gly Asn Gln Ala Lys His Gln Ile Arg Ser Val Asp
            260                 265                 270
Gly Val Thr Tyr Tyr Phe Asp Ala Asp Ser Gly Asn Ala Thr Ala Phe
        275                 280                 285
Lys Ala Val Thr Asn Gly Arg Tyr Ala Glu Gln Thr Thr Lys Asp Lys
    290                 295                 300
Asp Gly Asn Glu Thr Ser Tyr Trp Ala Tyr Leu Asp Asn Gln Gly Asn
```

```
        305                 310                 315                 320
    Ala Ile Lys Gly Leu Asn Asp Val Asn Gly Glu Ile Gln Tyr Phe Asp
                    325                 330                 335

Glu His Thr Gly Glu Gln Leu Lys Gly His Thr Ala Thr Val Asp Gly
                    340                 345                 350

Thr Thr Tyr Tyr Phe Glu Gly Asn Lys Gly Asn Leu Val Ser Val Val
                    355                 360                 365

Asn Thr Ala Pro Thr Gly Gln Tyr Lys Ile Asn Gly Asp Asn Val Tyr
                    370                 375                 380

Tyr Leu Asp Asn Asn Glu Ala Ile Lys Gly Leu Tyr Gly Ile Asn
    385                 390                 395                 400

Gly Asn Leu Asn Tyr Phe Asp Leu Ala Thr Gly Ile Gln Leu Lys Gly
                    405                 410                 415

Gln Ala Lys Asn Ile Asp Gly Ile Gly Tyr Tyr Phe Gln Asn Asn
                    420                 425                 430

Gly Asn Gly Glu Tyr Arg Tyr Ser Leu Thr Gly Pro Val Val Lys Asp
                    435                 440                 445

Val Tyr Ser Gln His Asn Ala Val Asn Asn Leu Ser Ala Asn Asn Phe
                    450                 455                 460

Lys Asn Leu Val Asp Gly Phe Leu Thr Ala Glu Thr Trp Tyr Arg Pro
    465                 470                 475                 480

Ala Gln Ile Leu Ser His Gly Thr Asp Trp Val Ala Ser Thr Asp Lys
                    485                 490                 495

Asp Phe Arg Pro Leu Ile Thr Val Trp Trp Pro Asn Lys Asp Ile Gln
                    500                 505                 510

Val Asn Tyr Leu Lys Leu Met Gln Gln Ile Gly Ile Leu Asp Asn Ser
                    515                 520                 525

Val Val Phe Asp Thr Asn Asp Gln Leu Val Leu Asn Lys Gly Ala
                    530                 535                 540

Glu Ser Ala Gln Ile Gly Ile Glu Lys Lys Val Ser Glu Thr Gly Asn
    545                 550                 555                 560

Thr Asp Trp Leu Asn Glu Leu Leu Phe Ala Pro Asn Gly Asn Gln Pro
                    565                 570                 575

Ser Phe Ile Lys Gln Gln Tyr Leu Trp Asn Val Asp Ser Glu Tyr Pro
                    580                 585                 590

Gly Gly Trp Phe Gln Gly Gly Tyr Leu Ala Tyr Gln Asn Ser Asp Leu
                    595                 600                 605

Thr Pro Tyr Ala Asn Thr Asn Pro Asp Tyr Arg Thr His Asn Gly Leu
                    610                 615                 620

Glu Phe Leu Leu Ala Asn Asp Val Asp Asn Ser Asn Pro Val Val Gln
    625                 630                 635                 640

Ala Glu Gln Leu Asn Trp Leu Tyr Tyr Leu Met Asn Phe Gly Gln Ile
                    645                 650                 655

Thr Ala Asn Asp Ser Asn Ala Asn Phe Asp Ser Met Arg Ile Asp Ala
                    660                 665                 670

Ile Ser Phe Val Asp Pro Gln Ile Ala Lys Lys Ala Tyr Asp Leu Leu
                    675                 680                 685

Asp Lys Met Tyr Gly Leu Thr Asp Asn Glu Ala Val Ala Asn Gln His
                    690                 695                 700

Ile Ser Ile Val Glu Ala Pro Lys Gly Glu Thr Pro Ile Thr Val Glu
    705                 710                 715                 720

Lys Gln Ser Ala Leu Val Glu Ser Asn Trp Arg Asp Arg Met Lys Gln
                    725                 730                 735
```

```
Ser Leu Ser Lys Asn Ala Thr Leu Asp Lys Leu Asp Pro Asp Pro Ala
                740                 745                 750

Ile Asn Ser Leu Glu Lys Leu Val Ala Asp Asp Leu Val Asn Arg Ser
            755                 760                 765

Gln Ser Ser Asp Lys Asp Ser Ser Thr Ile Pro Asn Tyr Ser Ile Val
770                 775                 780

His Ala His Asp Lys Asp Ile Gln Asp Thr Val Ile His Ile Met Lys
785                 790                 795                 800

Ile Val Asn Asn Asn Pro Asn Ile Ser Met Ser Asp Phe Thr Met Gln
                805                 810                 815

Gln Leu Gln Asn Gly Leu Lys Ala Phe Tyr Glu Asp Gln His Gln Ser
            820                 825                 830

Val Lys Lys Tyr Asn Gln Tyr Asn Ile Pro Ser Ala Tyr Ala Leu Leu
        835                 840                 845

Leu Thr Asn Lys Asp Thr Val Pro Arg Val Phe Tyr Gly Asp Met Tyr
850                 855                 860

Gln Asp Tyr Gly Asp Asp Leu Asp Gly Gly Gln Tyr Met Ala Thr Lys
865                 870                 875                 880

Ser Ile Tyr Tyr Asn Ala Ile Glu Gln Met Met Lys Ala Arg Leu Lys
                885                 890                 895

Tyr Val Ala Gly Gly Gln Ile Met Ala Val Thr Lys Ile Lys Asn Asp
            900                 905                 910

Gly Ile Asn Lys Asp Gly Thr Asn Lys Ser Gly Glu Val Leu Thr Ser
        915                 920                 925

Val Arg Phe Gly Lys Asp Ile Met Asp Ala Gln Gly Gln Gly Thr Ala
930                 935                 940

Glu Ser Arg Asn Gln Gly Ile Gly Val Ile Val Ser Asn Ser Ser Gly
945                 950                 955                 960

Leu Glu Leu Lys Asn Ser Asp Ser Ile Thr Leu His Met Gly Ile Ala
                965                 970                 975

His Lys Asn Gln Ala Tyr Arg Ala Leu Met Leu Thr Asn Asp Lys Gly
            980                 985                 990

Ile Val Asn Tyr Asp Gln Asp Asn Ala Pro Ile Ala Trp Thr Asn
        995                 1000                1005

Asp His Gly Asp Leu Ile Phe Thr Asn Gln Met Ile Asn Gly Gln
    1010                1015                1020

Ser Asp Thr Ala Val Lys Gly Tyr Leu Asn Pro Glu Val Ala Gly
    1025                1030                1035

Tyr Leu Ala Val Trp Val Pro Val Gly Ala Asn Asn Gln Asp
    1040                1045                1050

Ala Arg Thr Val Thr Thr Asn Gln Lys Asn Thr Asp Gly Lys Val
    1055                1060                1065

Leu His Thr Asn Ala Ala Leu Asp Ser Lys Leu Met Tyr Glu Gly
    1070                1075                1080

Phe Ser Asn Phe Gln Lys Met Pro Thr Arg Gly Asn Gln Tyr Ala
    1085                1090                1095

Asn Val Val Ile Thr Lys Asn Ile Asp Leu Phe Lys Ser Trp Gly
    1100                1105                1110

Ile Thr Asp Phe Glu Leu Ala Pro Gln Tyr Arg Ser Ser Asp Gly
    1115                1120                1125

Lys Asp Ile Thr Asp Arg Phe Leu Asp Ser Ile Val Gln Asn Gly
    1130                1135                1140
```

```
Tyr Gly Leu Ser Asp Arg Tyr Asp Leu Gly Phe Lys Thr Pro Thr
1145                1150                1155

Lys Tyr Gly Thr Asp Gln Asp Leu Arg Lys Ala Ile Glu Arg Leu
1160                1165                1170

His Gln Ala Gly Met Ser Val Met Ala Asp Phe Val Ala Asn Gln
1175                1180                1185

Ile Tyr Gly Leu His Ala Asp Lys Glu Val Val Ser Ala Gln His
1190                1195                1200

Val Asn Ile Asn Gly Asp Thr Lys Leu Val Val Asp Pro Arg Tyr
1205                1210                1215

Gly Thr Gln Met Thr Val Val Asn Ser Val Gly Gly Asp Tyr
1220                1225                1230

Gln Ala Lys Tyr Gly Gly Glu Tyr Leu Asp Thr Ile Ser Lys Leu
1235                1240                1245

Tyr Pro Gly Leu Leu Leu Asp Ser Asn Gly Gln Lys Ile Asp Leu
1250                1255                1260

Ser Thr Lys Ile Lys Glu Trp Ser Ala Lys Tyr Leu Asn Gly Ser
1265                1270                1275

Asn Ile Pro Gln Val Gly Met Gly Tyr Val Leu Lys Asp Trp Asn
1280                1285                1290

Asn Gly Gln Tyr Phe His Ile Leu Asp Lys Glu Gly Gln Tyr Ser
1295                1300                1305

Leu Pro Thr Gln Leu Val Ser Asn Asp Pro Glu Thr Gln Ile Gly
1310                1315                1320

Glu Ser Val Asn Tyr Lys Tyr Phe Ile Gly Asn Ser Asp Ala Thr
1325                1330                1335

Tyr Asn Met Tyr His Asn Leu Pro Asn Thr Val Ser Leu Ile Asn
1340                1345                1350

Ser Gln Glu Gly Gln Ile Lys Thr Gln Ser Gly Val Thr Ser
1355                1360                1365

Asp Tyr Glu Gly Gln Gln Val Gln Val Thr Arg Gln Tyr Thr Asp
1370                1375                1380

Ser Lys Gly Val Ser Trp Asn Leu Ile Thr Phe Ala Gly Gly Asp
1385                1390                1395

Leu Gln Gly Gln Lys Leu Trp Val Asp Ser Arg Ala Leu Thr Met
1400                1405                1410

Thr Pro Phe Lys Thr Met Asn Gln Ile Ser Phe Ile Ser Tyr Ala
1415                1420                1425

Asn Arg Asn Asp Gly Leu Phe Leu Asn Ala Pro Tyr Gln Val Lys
1430                1435                1440

Gly Tyr Gln Leu Ala Gly Met Ser Asn Gln Tyr Lys Gly Gln Gln
1445                1450                1455

Val Thr Ile Ala Gly Val Ala Asn Val Ser Gly Lys Asp Trp Ser
1460                1465                1470

Leu Ile Ser Phe Asn Gly Thr Gln Tyr Trp Ile Asp Ser Gln Ala
1475                1480                1485

Leu Asn Thr Asn Phe Thr His Asp Met Asn Gln Lys Val Phe Val
1490                1495                1500

Asn Thr Thr Ser Asn Leu Asp Gly Leu Phe Leu Asn Ala Pro Tyr
1505                1510                1515

Arg Gln Pro Gly Tyr Lys Leu Ala Gly Leu Ala Lys Asn Tyr Asn
1520                1525                1530

Asn Gln Thr Val Thr Val Ser Gln Gln Tyr Phe Asp Asp Gln Gly
```

```
                    1535                1540                1545

Thr Val Trp Ser Glu Val Val Leu Gly Gly Gln Thr Val Trp Val
    1550                1555                1560

Asp Asn His Ala Leu Ala Gln Met Gln Val Ser Asp Thr Ser Gln
    1565                1570                1575

Gln Leu Tyr Val Asn Ser Asn Gly Arg Asn Asp Gly Leu Phe Leu
    1580                1585                1590

Asn Ala Pro Tyr Arg Gly Gln Gly Ser Gln Leu Ile Gly Met Thr
    1595                1600                1605

Ala Asp Tyr Asn Gly Gln His Val Gln Val Thr Lys Gln Gly Gln
    1610                1615                1620

Asp Ala Tyr Gly Ala Gln Trp Arg Leu Ile Thr Leu Asn Asn Gln
    1625                1630                1635

Gln Val Trp Val Asp Ser Arg Ala Leu Ser Thr Thr Ile Val Gln
    1640                1645                1650

Ala Met Asn Asp Asp Met Tyr Val Asn Ser Asn Gln Arg Thr Asp
    1655                1660                1665

Gly Leu Trp Leu Asn Ala Pro Tyr Thr Met Ser Gly Ala Lys Trp
    1670                1675                1680

Ala Gly Asp Thr Arg Ser Ala Asn Gly Arg Tyr Val His Ile Ser
    1685                1690                1695

Lys Ala Tyr Ser Asn Glu Val Gly Asn Thr Tyr Tyr Leu Thr Asn
    1700                1705                1710

Leu Asn Gly Gln Ser Thr Trp Ile Asp Lys Arg Ala Phe Thr Ala
    1715                1720                1725

Thr Phe Asp Gln Val Val Ala Leu Asn Ala Thr Ile Val Ala Arg
    1730                1735                1740

Gln Arg Pro Asp Gly Met Phe Lys Thr Ala Pro Tyr Gly Glu Ala
    1745                1750                1755

Gly Ala Gln Phe Val Asp Tyr Val Thr Asn Tyr Asn Gln Gln Thr
    1760                1765                1770

Val Pro Val Thr Lys Gln His Ser Asp Ala Gln Gly Asn Gln Trp
    1775                1780                1785

Tyr Leu Ala Thr Val Asn Gly Thr Gln Tyr Trp Ile Asp Gln Arg
    1790                1795                1800

Ser Phe Ser Pro Val Val Thr Lys Val Asp Tyr Gln Ala Lys
    1805                1810                1815

Ile Val Pro Arg Thr Thr Arg Asp Gly Val Phe Ser Gly Ala Pro
    1820                1825                1830

Tyr Gly Glu Val Asn Ala Lys Leu Val Asn Met Ala Thr Ala Tyr
    1835                1840                1845

Gln Asn Gln Val Val His Ala Thr Gly Glu Tyr Thr Asn Ala Ser
    1850                1855                1860

Gly Ile Thr Trp Ser Gln Phe Ala Leu Ser Gly Gln Glu Asp Lys
    1865                1870                1875

Leu Trp Ile Asp Lys Arg Ala Leu Gln Ala
    1880                1885

<210> SEQ ID NO 10
<211> LENGTH: 5667
<212> TYPE: DNA
<213> ORGANISM: Leuconostoc citreum

<400> SEQUENCE: 10
```

-continued

| | | |
|---|---|---|
| atggaaatga aagaaacaat cactcgaaaa aagctgtaca agtcaggtaa aagctgggtt | 60 | |
| gcggctgcta cagcatttgc cgttatgggg gtatctgcgg taacaactgt cagtgccgat | 120 | |
| acacaaacgc cggttggtac aacacagagc caacaggatt tgactggtca gacagggcaa | 180 | |
| gacaagccaa caacgaaaga agttatcgac aaaaaggaac cggttcctca agtatcagca | 240 | |
| caaaacgttg gtgacttgtc agcagatgca aagactccaa aagctgatga taagcaagat | 300 | |
| acgcagccaa caaatgcaca gttacctgat caaggtaaca agcaaacgaa tagtaacagt | 360 | |
| gataagggag taaggagtc aacaacagct cctgttaaaa cgactgatgt accaagcaag | 420 | |
| tcagtcgcac cagaaaccaa tactagtatt aatggtggcc aatatgtaga aaagatggc | 480 | |
| caatttgttt atattgatca atctggtaag caggtaagtg gattacaaaa tattgaaggt | 540 | |
| catacgcaat attttgatcc gaaaacaggt tatcaaacta aaggtgaatt aaagaatatt | 600 | |
| gatgataatg cttattattt tgataaaaat agtggcaatg gtcgtacatt tacaaaaatt | 660 | |
| agtaatggta gctattctga aaaagatggc atgtggcagt atgttgatag ccatgacaag | 720 | |
| caaccagtaa agggtctata tgatgttgaa gggaatttac agtattttga cctgtcaaca | 780 | |
| ggtaatcagg ctaaacatca aatacgttca gttgatggtg tcacttatta ttttgacgca | 840 | |
| gacagtggta acgctacggc atttaaagcg gttaccaatg gccgttatgc tgagcagaca | 900 | |
| acgaaagata agatggcaa tgagacaagt tattgggctt atcttgataa tcaggggaat | 960 | |
| gctatcaaag gtctaaatga cgttaatggc gaaatacaat attttgatga acatactgga | 1020 | |
| gaacaactaa aaggccatac agctacggtt gatgggacaa cgtactattt tgaaggcaat | 1080 | |
| aaaggtaatc tcgtcagtgt tgttaacaca gcaccaacag gtcaatataa aattaacgga | 1140 | |
| gacaatgttt attatcttga caacaataat gaagcaataa agggattata tggcatcaat | 1200 | |
| ggcaatctga attactttga tttagcaacg gggatacaac tcaagggcca agcaaaaaat | 1260 | |
| attgatggta ttggttatta ttttgatcaa aataatggca atggtgagta taggtacagt | 1320 | |
| ttaacaggtc cagtggttaa agacgtttat tctcaacaca atgctgtgaa taatttgagc | 1380 | |
| gcaaataatt ttaagaatct tgtggatggt tttttaacag cagagacctg gtatcgtcca | 1440 | |
| gcacaaattt tgtctcatgg tacagactgg gtagcctcaa ctgataaaga tttcagacca | 1500 | |
| cttattacag tctggtggcc aaacaaggat attcaggtca actatctaaa gttaatgcaa | 1560 | |
| caaatcggta tactagataa ctcagtagta tttgatacaa ataatgatca actagtgtta | 1620 | |
| aataaaggtg ctgagagcgc acaaattggc atcgaaaaaa aggttagtga gacaggcaat | 1680 | |
| acagattggt taaatgagtt gcttttttgct cctaacggaa accaaccatc gtttatcaaa | 1740 | |
| caacaatatc tttggaatgt tgattctgaa tatcctggtg gttggtttca gggaggttat | 1800 | |
| ctagcttatc aaaatagtga tttaacacca tgctaata caaatcctga ttatcgaaca | 1860 | |
| cataatgggt tagagttctt actagccaat gatgttgaca actccaatcc agtcgtacag | 1920 | |
| gctgagcaac tgaactggct atattatttg atgaattttg ccaaattac agcaaatgat | 1980 | |
| tcaaatgcca attttgatag tatgagaatt gatgcaattt catttgttga tccacaaatt | 2040 | |
| gctaaaaaag cttatgacct gttagataaa atgtatggat taactgacaa tgaggcagtt | 2100 | |
| gccaatcaac atatttcaat tgttgaagct ccaaagggggg aaacgccaat taccgttgaa | 2160 | |
| aagcagagtg ccctagttga atcgaactgg cgtgatagga tgaagcaatc attatcaaaa | 2220 | |
| aatgccactc tagataagct agatcctgac cctgctatca attctttgga aaagcttgtc | 2280 | |
| gcagatgatt tagtaaaccg ttcccaaagt tcagataaag acagttcaac gataccaaac | 2340 | |
| tactcgatag ttcatgcaca tgataaagac attcaagaca ctgttattca tatcatgaaa | 2400 | |

```
atagttaata acaatccaaa catatctatg agtgacttca caatgcagca attgcaaaat    2460
gggttgaaag cattttacga agatcaacac cagtctgtga aaaatataa ccaatacaat     2520 attcctagtg catatgcttt gttgttaacc aataaagata ccgtaccacg agttttttat    2580
ggtgacatgt accaagacta tggtgatgat ttagatggtg gtcagtatat ggctacaaaa    2640
tcaatttatt ataatgccat tgagcaaatg atgaaggcgc gtttgaagta cgttgctggt    2700
ggtcaaataa tggccgtgac aaaaataaaa atgatggta tcaacaaaga tggtaccaat     2760
aagtcaggtg aggttcttac aagcgttcga tttggaaaag atatcatgga cgcacagggc    2820
cagggcacag ctgagagtag aaatcagggc attggtgtca tcgtatccaa tagtagcggt    2880
cttgagttaa agaatagtga cagtatcacc ttgcatatgg ggattgcaca taaaaatcaa    2940
gcataccgag cattaatgct taccaatgat aaagggattg ttaactacga tcaagataat    3000
aatgctccga ttgcttggac taatgaccac ggtgatttaa ttttcacgaa tcaaatgatt    3060
aacggtcaaa gtgatacggc agttaagggt tatcttaatc ctgaagtcgc aggctactta    3120
gccgtttggg taccagttgg cgccaatgac aaccaagatg cgagaactgt gacaacgaat    3180
caaaaaaata ctgatggaaa ggtgttgcac acgaatgctg cgcttgattc taaattaatg    3240
tatgaagggt tctccaattt ccagaaaatg ccgacacgtg gtaatcagta cgctaatgtg    3300
gttattacta aaaatattga tttatttaaa tcatggggaa ttactgattt tgaattagca    3360
cctcaatatc gttcaagcga cggaaaagat attaccgacc gttttcttga ctcaattgtt    3420
caaaatggtt acggattgag cgatcgctat gacctgggat ttaagacacc cactaagtat    3480
ggcacggacc aagacttgcg aaaagcaatt gaaagattac accaggctgg tatgtcagta    3540
atggcagatt ttgtagccaa tcaaatttat ggcctacatg ctgataaaga agttgtgtcg    3600
gctcagcatg tgaatattaa tggtgataca aagttagtag tagatccacg ctacggcaca    3660
caaatgactg ttgttaattc cgttggtggt ggtgattatc aagctaaata tggtggtgag    3720
tacttagata ctataagtaa gctttacccct gggttactct tagatagtaa tgggcaaaaa    3780
atagatttgt ctacaaaaat taaagaatgg tcagcaaaat atctaaacgg gagcaacatt    3840
cctcaagtgg gtatgggtta tgtcttaaaa gattggaaca atggccagta cttccacatt    3900
cttgataaag aagggcaata tagcctacca acacaactcg tttctaatga tccagaaaca    3960
caaataggtg agagtgtaaa ttataaatac tttattggta actctgatgc aacttataat    4020
atgtatcata atctgcctaa taccgttagc cttattaatt ctcaagaagg tcagattaag    4080
acacaacagt cgggtgtaac atctgattac gaagggcaac aagtgcaagt cacgcgtcaa    4140
tacactgaca gtaagggtgt gagttggaac ttaattacct ttgctggtgg tgatttacaa    4200
ggacaaaagc tttgggtgga tagtcgtgcg ttaactatga caccatttaa aacgatgaat    4260
caaataagct tcattagtta tgctaaccgc aatgatgggt tgttcttgaa tgcgccatac    4320
caagtcaagg ggtatcaatt agctgggatg tccaaccaat acaagggcca acaagtgacc    4380
attgccgggg tggcgaacgt ttctggtaaa gactggagtc tgattagttt taatgggaca    4440
cagtactgga ttgatagtca ggcattgaat accaatttca cacatgacat gaaccaaaag    4500
gtctttgtca atacaactag taatcttgat gggttattct taaatgcgcc ataccgtcaa    4560
ccaggttata agttagccgg tttggctaaa aattacaaca accaaacggt taccgttagt    4620
caacagtact ttgatgatca aggcacggtc tggagtgagg ttgttcttgg gggtcagacg    4680 gtctggggttg ataaccatgc attggcacag atgcaagtca gtgatacaag ccaacagctc    4740
```

| | |
|---|---|
| tatgtgaata gcaatggtcg taatgatggg ttattcttga atgcgccata tcgtggtcaa | 4800 |
| gggtcacaac tcataggcat gacggcagat tataatgggc aacatgtaca agtgaccaag | 4860 |
| caagggcaag atgcctacgg tgcacaatgg cgtcttatta cgctaaataa tcaacaggtc | 4920 |
| tgggttgata gtcgcgcttt gagcacaaca atcgtgcaag ccatgaatga tgatatgtat | 4980 |
| gtgaatagca accaacggac agatggtttg tggttaaacg caccttatac gatgagtggg | 5040 |
| gctaaatggg ctggtgatac gcgttcagct aatgggcgct atgtccatat ttcaaaagct | 5100 |
| tattcaaacg aagtcggcaa cacatattac ttgacgaatt tgaatggtca aagcacatgg | 5160 |
| attgacaagc gggcgtttac tgcgaccttt gaccaggtgg tggcattaaa tgcaacgatt | 5220 |
| gtggcacgcc aacgaccaga tgggatgttt aagacagcac catatggtga agcggggcg | 5280 |
| cagtttgtcg attatgtgac aaactataac cagcaaaccg tgccagtaac aaagcaacat | 5340 |
| tcagatgctc agggtaatca atggtactta gcgacagtga atgggacaca atactggatt | 5400 |
| gatcaacggt cattttcacc agtagtaacg aaggtggttg attatcaagc taagattgtg | 5460 |
| ccacggacaa cacgtgatgg tgtgtttagt ggcgcaccct atggggaagt gaatgctaag | 5520 |
| ctagttaaca tggcaactgc gtatcaaaat caagttgtcc atgcgacagg agaatatacg | 5580 |
| aatgcttcag ggatcacatg gagtcagttc gcgttaagtg ggcaagaaga caagctatgg | 5640 |
| attgataagc gtgctttgca agcttaa | 5667 |

<210> SEQ ID NO 11
<211> LENGTH: 3822
<212> TYPE: DNA
<213> ORGANISM: Artificial Sequence
<220> FEATURE:
<223> OTHER INFORMATION: delta PS delta C-1313

<400> SEQUENCE: 11

| | |
|---|---|
| gatacacaaa cgccggttgg tacaacacag agccaacagg atttgactgg tcagacaggg | 60 |
| caagacaagc caacaacgaa agaagttatc gacaaaaagg aaccggttcc tcaagtatca | 120 |
| gcacaaaacg ttggtgactt gtcagcagat gcaaagactc caaaagctga tgataagcaa | 180 |
| gatacgcagc caacaaatgc acagttacct gatcaaggta acaagcaaac gaatagtaac | 240 |
| agtgataagg gagtaaagga gtcaacaaca gctcctgtta aaacgactga tgtaccaagc | 300 |
| aagtcagtcg caccagaaac caatactagt attaatggtg gccaatatgt agaaaaagat | 360 |
| ggccaatttg tttatattga tcaatctggt aagcaggtaa gtggattaca aaatattgaa | 420 |
| ggtcatacgc aatattttga tccgaaaaca ggttatcaaa ctaaaggtga attaaagaat | 480 |
| attgatgata atgcttatta ttttgataaa aatagtggca atggtcgtac atttacaaaa | 540 |
| attagtaatg gtagctattc tgaaaaagat ggcatgtggc agtatgttga tagccatgac | 600 |
| aagcaaccag taaagggtct atatgatgtt gaagggaatt tacagtattt tgacctgtca | 660 |
| acaggtaatc aggctaaaca tcaaatacgt tcagttgatg gtgtcactta ttatttttgac | 720 |
| gcagacagtg gtaacgctac ggcatttaaa gcggttacca atggccgtta tgctgagcag | 780 |
| acaacgaaag ataaagatgg caatgagaca agttattggg cttatcttga taatcagggg | 840 |
| aatgctatca aaggtctaaa tgacgttaat ggcgaaatac aatatttga tgaacatact | 900 |
| ggagaacaac taaaaggcca tacagctacg gttgatggga caacgtacta ttttgaaggc | 960 |
| aataaaggta atctcgtcag tgttgttaac acagcaccaa caggtcaata taaaattaac | 1020 |
| ggagacaatg tttattatct tgacaacaat aatgaagcaa taaagggatt atatggcatc | 1080 |
| aatggcaatc tgaattactt tgatttagca acggggatac aactcaaggg ccaagcaaaa | 1140 |

```
aatattgatg gtattggtta ttattttgat caaaataatg gcaatggtga gtataggtac    1200
agtttaacag gtccagtggt taaagacgtt tattctcaac acaatgctgt gaataatttg    1260
agcgcaaata attttaagaa tcttgtggat ggttttttaa cagcagagac ctggtatcgt    1320
ccagcacaaa ttttgtctca tggtacagac tgggtagcct caactgataa agatttcaga    1380
ccacttatta cagtctggtg gccaaacaag gatattcagg tcaactatct aaagttaatg    1440
caacaaatcg gtatactaga taactcagta gtatttgata caaataatga tcaactagtg    1500
ttaaataaag gtgctgagag cgcacaaatt ggcatcgaaa aaaggttag tgagacaggc     1560 aatacagatt ggttaaatga gttgcttttt gctcctaacg gaaaccaacc atcgtttatc    1620
aaacaacaat atctttggaa tgttgattct gaatatcctg gtggttggtt tcagggaggt    1680
tatctagctt atcaaaatag tgatttaaca ccatatgcta atacaaatcc tgattatcga    1740
acacataatg ggttagagtt cttactagcc aatgatgttg acaactccaa tccagtcgta    1800
caggctgagc aactgaactg gctatattat ttgatgaatt ttggccaaat tacagcaaat    1860
gattcaaatg ccaattttga tagtatgaga attgatgcaa tttcatttgt tgatccacaa    1920
attgctaaaa aagcttatga cctgttagat aaaatgtatg gattaactga caatgaggca    1980
gttgccaatc aacatatttc aattgttgaa gctccaaagg gggaaacgcc aattaccgtt    2040
gaaaagcaga gtgccctagt tgaatcgaac tggcgtgata ggatgaagca atcattatca    2100
aaaaatgcca ctctagataa gctagatcct gaccctgcta tcaattcttt ggaaaagctt    2160
gtcgcagatg atttagtaaa ccgttcccaa agttcagata agacagttc aacgatacca      2220 aactactcga tagttcatgc acatgataaa gacattcaag acactgttat tcatatcatg    2280
aaaatagtta ataacaatcc aaacatatct atgagtgact tcacaatgca gcaattgcaa    2340
aatgggttga agcattta cgaagatcaa caccagtctg tgaaaaaata taccaatac       2400 aatattccta gtgcatatgc tttgttgtta accaataaag ataccgtacc acgagttttt    2460
tatggtgaca tgtaccaaga ctatggtgat gatttagatg gtggtcagta tatggctaca    2520
aaatcaattt attataatgc cattgagcaa atgatgaagg cgcgtttgaa gtacgttgct    2580
ggtggtcaaa taatggccgt gacaaaaata aaaaatgatg gtatcaacaa agatggtacc    2640
aataagtcag gtgaggttct tacaagcgtt cgatttggaa aagatatcat ggacgcacag    2700
ggccagggca cagctgagag tagaaatcag ggcattggtg tcatcgtatc caatagtagc    2760
ggtcttgagt taaagaatag tgacagtatc accttgcata tggggattgc acataaaaat    2820
caagcatacc gagcattaat gcttaccaat gataaaggga ttgttaacta cgatcaagat    2880
aataatgctc cgattgcttg gactaatgac cacggtgatt taattttcac gaatcaaatg    2940
attaacggtc aaagtgatac ggcagttaag ggttatctta atcctgaagt cgcaggctac    3000
ttagccgttt gggtaccagt tggcgccaat gacaaccaag atgcgagaac tgtgacaacg    3060
aatcaaaaaa atactgatgg aaaggtgttg cacacgaatg ctgcgcttga ttctaaatta    3120
atgtatgaag ggttctccaa tttccagaaa atgccgacac gtggtaatca gtacgctaat    3180
gtggttatta ctaaaaatat tgatttattt aaatcatggg gaattactga ttttgaatta    3240
gcacctcaat atcgttcaag cgacggaaaa gatattaccg accgttttct tgactcaatt    3300
gttcaaaatg gttacggatt gagcgatcgc tatgacctgg gatttaagac acccactaag    3360
tatggcacgg accaagactt gcgaaaagca attgaaagat tacaccaggc tggtatgtca    3420
gtaatggcag attttgtagc caatcaaatt tatggcctac atgctgataa agaagttgtg    3480
```

-continued

```
tcggctcagc atgtgaatat taatggtgat acaaagttag tagtagatcc acgctacggc    3540
acacaaatga ctgttgttaa ttccgttggt ggtggtgatt atcaagctaa atatggtggt    3600
gagtacttag atactataag taagctttac cctgggttac tcttagatag taatgggcaa    3660
aaaatagatt tgtctacaaa aattaaagaa tggtcagcaa atatctaaa cgggagcaac     3720 attcctcaag tgggtatggg ttatgtctta aaagattgga caatggcca gtacttccac     3780 attcttgata agaagggca atatagccta ccaacacaac tc                       3822
```

<210> SEQ ID NO 12
<211> LENGTH: 1274
<212> TYPE: PRT
<213> ORGANISM: Artificial Sequence
<220> FEATURE:
<223> OTHER INFORMATION: Delta PS, delta C-1313

<400> SEQUENCE: 12

```
Asp Thr Gln Thr Pro Val Gly Thr Thr Gln Ser Gln Gln Asp Leu Thr
1               5                   10                  15

Gly Gln Thr Gly Gln Asp Lys Pro Thr Thr Lys Glu Val Ile Asp Lys
            20                  25                  30

Lys Glu Pro Val Pro Gln Val Ser Ala Gln Asn Val Gly Asp Leu Ser
        35                  40                  45

Ala Asp Ala Lys Thr Pro Lys Ala Asp Lys Gln Asp Thr Gln Pro
    50                  55                  60

Thr Asn Ala Gln Leu Pro Asp Gln Gly Asn Lys Gln Thr Asn Ser Asn
65                  70                  75                  80

Ser Asp Lys Gly Val Lys Glu Ser Thr Thr Ala Pro Val Lys Thr Thr
                85                  90                  95

Asp Val Pro Ser Lys Ser Val Ala Pro Glu Thr Asn Thr Ser Ile Asn
            100                 105                 110

Gly Gly Gln Tyr Val Glu Lys Asp Gly Gln Phe Val Tyr Ile Asp Gln
        115                 120                 125

Ser Gly Lys Gln Val Ser Gly Leu Gln Asn Ile Glu Gly His Thr Gln
    130                 135                 140

Tyr Phe Asp Pro Lys Thr Gly Tyr Gln Thr Lys Gly Glu Leu Lys Asn
145                 150                 155                 160

Ile Asp Asp Asn Ala Tyr Tyr Phe Asp Lys Asn Ser Gly Asn Gly Arg
                165                 170                 175

Thr Phe Thr Lys Ile Ser Asn Gly Ser Tyr Ser Glu Lys Asp Gly Met
            180                 185                 190

Trp Gln Tyr Val Asp Ser His Asp Lys Gln Pro Val Lys Gly Leu Tyr
        195                 200                 205

Asp Val Glu Gly Asn Leu Gln Tyr Phe Asp Leu Ser Thr Gly Asn Gln
    210                 215                 220

Ala Lys His Gln Ile Arg Ser Val Asp Gly Val Thr Tyr Tyr Phe Asp
225                 230                 235                 240

Ala Asp Ser Gly Asn Ala Thr Ala Phe Lys Ala Val Thr Asn Gly Arg
                245                 250                 255

Tyr Ala Glu Gln Thr Thr Lys Asp Lys Asp Gly Asn Glu Thr Ser Tyr
            260                 265                 270

Trp Ala Tyr Leu Asp Asn Gln Gly Asn Ala Ile Lys Gly Leu Asn Asp
        275                 280                 285

Val Asn Gly Glu Ile Gln Tyr Phe Asp Glu His Thr Gly Glu Gln Leu
    290                 295                 300
```

-continued

```
Lys Gly His Thr Ala Thr Val Asp Gly Thr Thr Tyr Phe Glu Gly
305                 310                 315                 320

Asn Lys Gly Asn Leu Val Ser Val Asn Thr Ala Pro Thr Gly Gln
            325                 330                 335

Tyr Lys Ile Asn Gly Asp Asn Val Tyr Tyr Leu Asp Asn Asn Glu
            340                 345                 350

Ala Ile Lys Gly Leu Tyr Gly Ile Asn Gly Asn Leu Asn Tyr Phe Asp
            355                 360                 365

Leu Ala Thr Gly Ile Gln Leu Lys Gly Gln Ala Lys Asn Ile Asp Gly
            370                 375                 380

Ile Gly Tyr Tyr Phe Asp Gln Asn Asn Gly Asn Gly Glu Tyr Arg Tyr
385                 390                 395                 400

Ser Leu Thr Gly Pro Val Val Lys Asp Val Tyr Ser Gln His Asn Ala
            405                 410                 415

Val Asn Asn Leu Ser Ala Asn Asn Phe Lys Asn Leu Val Asp Gly Phe
            420                 425                 430

Leu Thr Ala Glu Thr Trp Tyr Arg Pro Ala Gln Ile Leu Ser His Gly
            435                 440                 445

Thr Asp Trp Val Ala Ser Thr Asp Lys Asp Phe Arg Pro Leu Ile Thr
450                 455                 460

Val Trp Trp Pro Asn Lys Asp Ile Gln Val Asn Tyr Leu Lys Leu Met
465                 470                 475                 480

Gln Gln Ile Gly Ile Leu Asp Asn Ser Val Phe Asp Thr Asn Asn
                485                 490                 495

Asp Gln Leu Val Leu Asn Lys Gly Ala Glu Ser Ala Gln Ile Gly Ile
            500                 505                 510

Glu Lys Lys Val Ser Glu Thr Gly Asn Thr Asp Trp Leu Asn Glu Leu
            515                 520                 525

Leu Phe Ala Pro Asn Gly Asn Gln Pro Ser Phe Ile Lys Gln Gln Tyr
            530                 535                 540

Leu Trp Asn Val Asp Ser Glu Tyr Pro Gly Gly Trp Phe Gln Gly Gly
545                 550                 555                 560

Tyr Leu Ala Tyr Gln Asn Ser Asp Leu Thr Pro Tyr Ala Asn Thr Asn
            565                 570                 575

Pro Asp Tyr Arg Thr His Asn Gly Leu Glu Phe Leu Leu Ala Asn Asp
            580                 585                 590

Val Asp Asn Ser Asn Pro Val Val Gln Ala Glu Gln Leu Asn Trp Leu
            595                 600                 605

Tyr Tyr Leu Met Asn Phe Gly Gln Ile Thr Ala Asn Asp Ser Asn Ala
            610                 615                 620

Asn Phe Asp Ser Met Arg Ile Asp Ala Ile Ser Phe Val Asp Pro Gln
625                 630                 635                 640

Ile Ala Lys Lys Ala Tyr Asp Leu Leu Asp Lys Met Tyr Gly Leu Thr
            645                 650                 655

Asp Asn Glu Ala Val Ala Asn Gln His Ile Ser Ile Val Glu Ala Pro
            660                 665                 670

Lys Gly Glu Thr Pro Ile Thr Val Glu Lys Gln Ser Ala Leu Val Glu
            675                 680                 685

Ser Asn Trp Arg Asp Arg Met Lys Gln Ser Leu Ser Lys Asn Ala Thr
            690                 695                 700

Leu Asp Lys Leu Asp Pro Asp Pro Ala Ile Asn Ser Leu Glu Lys Leu
705                 710                 715                 720

Val Ala Asp Asp Leu Val Asn Arg Ser Gln Ser Ser Asp Lys Asp Ser
```

```
                        725                 730                 735
Ser Thr Ile Pro Asn Tyr Ser Ile Val His Ala His Asp Lys Asp Ile
                    740                 745                 750
Gln Asp Thr Val Ile His Ile Met Lys Ile Val Asn Asn Asn Pro Asn
                755                 760                 765
Ile Ser Met Ser Asp Phe Thr Met Gln Gln Leu Gln Asn Gly Leu Lys
            770                 775                 780
Ala Phe Tyr Glu Asp Gln His Gln Ser Val Lys Lys Tyr Asn Gln Tyr
785                 790                 795                 800
Asn Ile Pro Ser Ala Tyr Ala Leu Leu Leu Thr Asn Lys Asp Thr Val
                805                 810                 815
Pro Arg Val Phe Tyr Gly Asp Met Tyr Gln Asp Tyr Gly Asp Asp Leu
                820                 825                 830
Asp Gly Gly Gln Tyr Met Ala Thr Lys Ser Ile Tyr Tyr Asn Ala Ile
                835                 840                 845
Glu Gln Met Met Lys Ala Arg Leu Lys Tyr Val Ala Gly Gly Gln Ile
            850                 855                 860
Met Ala Val Thr Lys Ile Lys Asn Asp Gly Ile Asn Lys Asp Gly Thr
865                 870                 875                 880
Asn Lys Ser Gly Glu Val Leu Thr Ser Val Arg Phe Gly Lys Asp Ile
                885                 890                 895
Met Asp Ala Gln Gly Gln Gly Thr Ala Glu Ser Arg Asn Gln Gly Ile
                900                 905                 910
Gly Val Ile Val Ser Asn Ser Ser Gly Leu Glu Leu Lys Asn Ser Asp
            915                 920                 925
Ser Ile Thr Leu His Met Gly Ile Ala His Lys Asn Gln Ala Tyr Arg
930                 935                 940
Ala Leu Met Leu Thr Asn Asp Lys Gly Ile Val Asn Tyr Asp Gln Asp
945                 950                 955                 960
Asn Asn Ala Pro Ile Ala Trp Thr Asn Asp His Gly Asp Leu Ile Phe
                965                 970                 975
Thr Asn Gln Met Ile Asn Gly Gln Ser Asp Thr Ala Val Lys Gly Tyr
                980                 985                 990
Leu Asn Pro Glu Val Ala Gly Tyr Leu Ala Val Trp Val Pro Val Gly
            995                 1000                1005
Ala Asn Asp Asn Gln Asp Ala Arg Thr Val Thr Thr Asn Gln Lys
        1010                1015                1020
Asn Thr Asp Gly Lys Val Leu His Thr Asn Ala Ala Leu Asp Ser
        1025                1030                1035
Lys Leu Met Tyr Glu Gly Phe Ser Asn Phe Gln Lys Met Pro Thr
        1040                1045                1050
Arg Gly Asn Gln Tyr Ala Asn Val Val Ile Thr Lys Asn Ile Asp
        1055                1060                1065
Leu Phe Lys Ser Trp Gly Ile Thr Asp Phe Glu Leu Ala Pro Gln
        1070                1075                1080
Tyr Arg Ser Ser Asp Gly Lys Asp Ile Thr Asp Arg Phe Leu Asp
        1085                1090                1095
Ser Ile Val Gln Asn Gly Tyr Gly Leu Ser Asp Arg Tyr Asp Leu
        1100                1105                1110
Gly Phe Lys Thr Pro Thr Lys Tyr Gly Thr Asp Gln Asp Leu Arg
        1115                1120                1125
Lys Ala Ile Glu Arg Leu His Gln Ala Gly Met Ser Val Met Ala
        1130                1135                1140
```

Asp Phe Val Ala Asn Gln Ile Tyr Gly Leu His Ala Asp Lys Glu
    1145                1150                1155

Val Val Ser Ala Gln His Val Asn Ile Asn Gly Asp Thr Lys Leu
    1160                1165                1170

Val Val Asp Pro Arg Tyr Gly Thr Gln Met Thr Val Val Asn Ser
    1175                1180                1185

Val Gly Gly Gly Asp Tyr Gln Ala Lys Tyr Gly Gly Glu Tyr Leu
    1190                1195                1200

Asp Thr Ile Ser Lys Leu Tyr Pro Gly Leu Leu Leu Asp Ser Asn
    1205                1210                1215

Gly Gln Lys Ile Asp Leu Ser Thr Lys Ile Lys Glu Trp Ser Ala
    1220                1225                1230

Lys Tyr Leu Asn Gly Ser Asn Ile Pro Gln Val Gly Met Gly Tyr
    1235                1240                1245

Val Leu Lys Asp Trp Asn Asn Gly Gln Tyr Phe His Ile Leu Asp
    1250                1255                1260

Lys Glu Gly Gln Tyr Ser Leu Pro Thr Gln Leu
    1265                1270

<210> SEQ ID NO 13
<211> LENGTH: 4244
<212> TYPE: DNA
<213> ORGANISM: Leuconostoc citreum

<400> SEQUENCE: 13

```
atggaaatga aagaaacaat cactcgaaaa aagctgtaca agtcaggtaa aagctgggtt      60
gcggctgcta cagcatttgc cgttatgggg gtatctgcgg taacaactgt cagtgccgat     120
acacaaacgc cggttggtac aacacagagc caacagaatt tgactggtca gacagggcaa     180
gacaagccaa caacgaaaga agttatcgac aaaaaggaac cggttcccca ggtatcagca     240
caaaatgctg gtgacttgtc agcagatgca aagactccaa aagctgatga taagcaagat     300
acgcagccaa caaatgcaca gttacctgat caaggtaaca agcaaacgaa tagtaacagt     360
gataagggag taaaggagtc aacaacagct cctgttaaaa cgactgatgt accaagcaag     420
tcagtcacac cagaaacaaa tactagtatt aatggtggac aatatgtaga aaaagatggc     480
caatttgttt atattgatca atctggtaag caggtaagtg gattacaaaa tattgaaggt     540
catacgcaat attttgatcc gaaaacaggt tatcaaacta aaggtgaatt aaagaatatt     600
gatgataatg cttattattt tgataaaaat agtggcaatg tcgtacatt tacaaaaatt     660 agtaatggta gctattctga aaaagatggc atgtggcagt atgttgatag ccatgacaag     720
caaccagtaa agggtctata tgatgttgaa gggaatttac agtattttga cctgtcaaca     780
ggtaatcagg ctaaacatca aatacgttca gttgatggtg tcacttatta tttcgacgca     840
gacagtggta acgctacggc atttaaagcg gttaccaatg ccgttatgc tgagcagaca     900 acgaaagata aagatggcaa tgagacaagt tattgggctt atcttgataa tcaggggaat     960
gctgtcaaag gtctaaatga cgtcaatggt gaaatacagt actttgatga aatcgctggc    1020
gcacagctaa aagtcacaca gctacggtt gatggtgtca cttactatttt tgaaagcaat    1080 aaaggaaatc tcgtaagtgt tgttaacgca gcgccgacag acaatataaa aatagatggt    1140
gataaagtat actatcttga taatcaaaat caaccattaa agggattgta tagtatcaat    1200
ggcaatctga attactttga tttagccacg gggatacaat caaaggtca ggcagaaaac    1260 atcaatggta ttggttatta ttttgatcaa aataatggca atggtgagta taggtacagt    1320
```

```
ttaacaggtc cagtggttaa agacgtttat tctcaacaca atgctgtgaa taatttgagc    1380
gcaaataatt ttaggaatct tgtggatggt ttcttaacag cagagacctg gtatcgtcca    1440
gcacaaattt tgtctcaggg taaagactgg gtagcctcaa ctgataaaga tttcagacca    1500
cttattacag tctggtggcc aaacaaggat attcaggtca actatctaaa gttaatgcaa    1560
caaatcggta tagtagataa ctcagtagta tttgatacaa ataatgatca actagtgtta    1620
aataaaggtg ctgagagcgc acaaattggc atcgaaaaaa aggttagcga gacaggcaat    1680
acagattggt taaatgagtt gcttttttgct cctaacggaa accaaccatc gtttatcaaa    1740
caacaatatc tttggaatgt tgattctgaa tatcctggtg gttggtttca gggaggttat    1800
ctatcttatc aaaatagtga tttaacacca tatgctaata caaatcctga ttatcgaaca    1860
cataatgggt tagagttctt actagccaat gatgttgaca actccaatcc agtcgtacag    1920
gctgagcaac tgaactggct atattatttg atgaattttg ccaaattac agcaaatgat     1980
tcaaatgcca attttgatag tatgagaatt gatgcaattt catttgttga tccacaaatt    2040
gctaaaaaag cttatgacct gttagataaa atgtatggat taactgacaa tgaggcagtt    2100
gccaatcaac atatttcaat tgttgaagct ccaaaggggg aaacgccaat taccgttgaa    2160
aagcagagtg ccctagttga atcgaactgg cgtgatagga tgaagcaatc attatcaaaa    2220
aatgccactc tagataagct agatcctgac cctgctatca attctttgga aaagcttgtc    2280
gcagatgatt tagtaaaccg ttcccaaagt tcagataaag acagttcaac gataccaaac    2340
tactcgatag ttcatgcaca tgataaagac attcaagaca ctgttattca tatcatgaaa    2400
atagttaata acaatccaaa catatctatg agtgacttca aatgcagca attgcaaaat     2460
gggttgaaag cattttacga agatcaacac cagtctgtga aaaaatataa ccaatacaat    2520
attcctagtg catatgcttt gttgttaacc aataaagata ccgtaccacg agttttttat    2580
ggtgacatgt accaagacta tggtgatgat ttagatggtg gtcagtatat ggctacaaaa    2640
tcaatttatt ataatgccat tgagcaaatg atgaaggcgc gtttgaagta cgttgctggt    2700
ggtcaaataa tggccgtgac aaaaatataaa aatgatggta tcaacaaaga tggtaccaat    2760
aagtcaggtg aggttcttac aagcgttcga tttggaaaag atatcatgga cgcacagggc    2820
cagggcacag ctgagagtag aaatcagggc attggtgtca tcgtatccaa tagtagcggt    2880
cttgagttaa agaatagtga cagtatcacc ttgcatatgg ggattgcaca taaaaatcaa    2940
gcataccgag cattaatgct taccaatgat aaagggattg ttaactacga tcaagataat    3000
aatgctccga ttgcttggac taatgaccac ggtgatttaa ttttcacgaa tcaaatgatt    3060
aacggtcaaa gtgatacggc agttaagggt tatcttaatc ctgaagtcgc aggctactta    3120
gccgtttggg taccagttgg cgccaatgac aaccaagatg cgagaactgt gacaacgaat    3180
caaaaaaata ctgatggaaa ggtgttgcac acgaatgctg cgcttgattc taaattaatg    3240
tatgaagggt tctccaattt ccagaaaatg ccgacacgtg gtaatcagta cgctaatgtg    3300
attattgcta aaaatattga tttatttaaa tcatgggaa ttactgattt tgaattagca     3360
cctcaatatc gttcaagcga cggaaaagat attaccgacc gttttcttga ctcaattgtt    3420
caaaatggtt acggattgag cgatcgctat gacctgggat ttaagacacc cactaagtat    3480
ggcacggacc aagacttgcg aaaagcaatt gaaagattac accaggctgg tatgtcagta    3540
atggcagatt ttgtagccaa tcaaatttat ggcctacatg ctgataaaga agttgtgtcg    3600
gctcagcatg tgaatattaa tggtgataca aagttagtag tagatccacg ctacggcaca    3660
```

-continued

```
caaatgactg ttgttaattc cgttggtggt ggtgattatc aagctaaata tggtggtgag    3720
tacttagata ctataagtaa gctttaccct gggttactct tagatagtaa tgggcaaaaa    3780
atagatttgt ctacaaaaat taaagaatgg tcagcaaaat atctaaacgg gagcaatatt    3840
cctcaagtgg gtatgggtta tgtcttaaaa gattggaaca atggccagta cttccacatt    3900
cttgataaag aagggcaata tagcctacca acacaactcg tttctaatga tccagaaaca    3960
caaataggtg agagtgtaaa ttataaatac tttattggta actctgatgc aacttataat    4020
atgtatcata atctgcctaa taccgttagc cttattaatt ctcaagaagg tcagattaag    4080
acacaacagt cgggtgtaac atctgattac gaagggcaac aagtgcaagt cacgcgccag    4140
tacacagata gtaagggtgt gagttggaac ttaattaccT ttgctggtgg tgatttacaa    4200
ggacaaaagc tttgggtgga tagtcgtgcg ttaactatga cacc                    4244
```

<210> SEQ ID NO 14
<211> LENGTH: 1611
<212> TYPE: PRT
<213> ORGANISM: Leuconostoc citreum

<400> SEQUENCE: 14

```
Met Glu Met Lys Glu Thr Ile Thr Arg Lys Lys Leu Tyr Lys Ser Gly
1               5                   10                  15

Lys Ser Trp Val Ala Ala Thr Ala Phe Ala Val Met Gly Val Ser
            20                  25                  30

Ala Val Thr Thr Val Ser Ala Asp Thr Gln Thr Pro Val Gly Thr Thr
        35                  40                  45

Gln Ser Gln Gln Asn Leu Thr Gly Gln Thr Gly Gln Asp Lys Pro Thr
    50                  55                  60

Thr Lys Glu Val Ile Asp Lys Lys Glu Pro Val Pro Gln Val Ser Ala
65                  70                  75                  80

Gln Asn Ala Gly Asp Leu Ser Ala Asp Ala Lys Thr Pro Lys Ala Asp
                85                  90                  95

Asp Lys Gln Asp Thr Gln Pro Thr Asn Ala Gln Leu Pro Asp Gln Gly
            100                 105                 110

Asn Lys Gln Thr Asn Ser Asn Ser Asp Lys Gly Val Lys Glu Ser Thr
        115                 120                 125

Thr Ala Pro Val Lys Thr Thr Asp Val Pro Ser Lys Ser Val Thr Pro
    130                 135                 140

Glu Thr Asn Thr Ser Ile Asn Gly Gly Gln Tyr Val Glu Lys Asp Gly
145                 150                 155                 160

Gln Phe Val Tyr Ile Asp Gln Ser Gly Lys Gln Val Ser Gly Leu Gln
                165                 170                 175

Asn Ile Glu Gly His Thr Gln Tyr Phe Asp Pro Lys Thr Gly Tyr Gln
            180                 185                 190

Thr Lys Gly Glu Leu Lys Asn Ile Asp Asp Asn Ala Tyr Tyr Phe Asp
        195                 200                 205

Lys Asn Ser Gly Asn Gly Arg Thr Phe Thr Lys Ile Ser Asn Gly Ser
    210                 215                 220

Tyr Ser Glu Lys Asp Gly Met Trp Gln Tyr Val Asp Ser His Asp Lys
225                 230                 235                 240

Gln Pro Val Lys Gly Leu Tyr Asp Val Glu Gly Asn Leu Gln Tyr Phe
                245                 250                 255

Asp Leu Ser Thr Gly Asn Gln Ala Lys His Gln Ile Arg Ser Val Asp
            260                 265                 270
```

```
Gly Val Thr Tyr Tyr Phe Asp Ala Asp Ser Gly Asn Ala Thr Ala Phe
            275                 280                 285

Lys Ala Val Thr Asn Gly Arg Tyr Ala Glu Gln Thr Thr Lys Asp Lys
290                 295                 300

Asp Gly Asn Glu Thr Ser Tyr Trp Ala Tyr Leu Asp Asn Gln Gly Asn
305                 310                 315                 320

Ala Val Lys Gly Leu Asn Asp Val Asn Gly Glu Ile Gln Tyr Phe Asp
                325                 330                 335

Glu Ile Ala Gly Ala Gln Leu Lys Gly His Thr Ala Thr Val Asp Gly
            340                 345                 350

Val Thr Tyr Tyr Phe Glu Ser Asn Lys Gly Asn Leu Val Ser Val Val
        355                 360                 365

Asn Ala Ala Pro Thr Gly Gln Tyr Lys Ile Asp Gly Asp Lys Val Tyr
370                 375                 380

Tyr Leu Asp Asn Gln Asn Gln Pro Leu Lys Gly Leu Tyr Ser Ile Asn
385                 390                 395                 400

Gly Asn Leu Asn Tyr Phe Asp Leu Ala Thr Gly Ile Gln Val Lys Gly
                405                 410                 415

Gln Ala Glu Asn Ile Asn Gly Ile Gly Tyr Tyr Phe Asp Gln Asn Asn
            420                 425                 430

Gly Asn Gly Glu Tyr Arg Tyr Ser Leu Thr Gly Pro Val Val Lys Asp
        435                 440                 445

Val Tyr Ser Gln His Asn Ala Val Asn Asn Leu Ser Ala Asn Asn Phe
    450                 455                 460

Arg Asn Leu Val Asp Gly Phe Leu Thr Ala Glu Thr Trp Tyr Arg Pro
465                 470                 475                 480

Ala Gln Ile Leu Ser Gln Gly Lys Asp Trp Val Ala Ser Thr Asp Lys
                485                 490                 495

Asp Phe Arg Pro Leu Ile Thr Val Trp Trp Pro Asn Lys Asp Ile Gln
            500                 505                 510

Val Asn Tyr Leu Lys Leu Met Gln Gln Ile Gly Ile Val Asp Asn Ser
        515                 520                 525

Val Val Phe Asp Thr Asn Asn Asp Gln Leu Val Leu Asn Lys Gly Ala
    530                 535                 540

Glu Ser Ala Gln Ile Gly Ile Glu Lys Lys Val Ser Glu Thr Gly Asn
545                 550                 555                 560

Thr Asp Trp Leu Asn Glu Leu Leu Phe Ala Pro Asn Gly Asn Gln Pro
                565                 570                 575

Ser Phe Ile Lys Gln Gln Tyr Leu Trp Asn Val Asp Ser Glu Tyr Pro
            580                 585                 590

Gly Gly Trp Phe Gln Gly Gly Tyr Leu Ser Tyr Gln Asn Ser Asp Leu
        595                 600                 605

Thr Pro Tyr Ala Asn Thr Asn Pro Asp Tyr Arg Thr His Asn Gly Leu
    610                 615                 620

Glu Phe Leu Leu Ala Asn Asp Val Asp Asn Ser Asn Pro Val Val Gln
625                 630                 635                 640

Ala Glu Gln Leu Asn Trp Leu Tyr Tyr Leu Met Asn Phe Gly Gln Ile
                645                 650                 655

Thr Ala Asn Asp Ser Asn Ala Asn Phe Asp Ser Met Arg Ile Asp Ala
            660                 665                 670

Ile Ser Phe Val Asp Pro Gln Ile Ala Lys Lys Ala Tyr Asp Leu Leu
        675                 680                 685

Asp Lys Met Tyr Gly Leu Thr Asp Asn Glu Ala Val Ala Asn Gln His
```

```
            690             695             700
Ile Ser Ile Val Glu Ala Pro Lys Gly Glu Thr Pro Ile Thr Val Glu
705             710             715             720
Lys Gln Ser Ala Leu Val Glu Ser Asn Trp Arg Asp Arg Met Lys Gln
                725             730             735
Ser Leu Ser Lys Asn Ala Thr Leu Asp Lys Leu Asp Pro Asp Pro Ala
            740             745             750
Ile Asn Ser Leu Glu Lys Leu Val Ala Asp Asp Leu Val Asn Arg Ser
        755             760             765
Gln Ser Ser Asp Lys Asp Ser Ser Thr Ile Pro Asn Tyr Ser Ile Val
    770             775             780
His Ala His Asp Lys Asp Ile Gln Asp Thr Val Ile His Ile Met Lys
785             790             795             800
Ile Val Asn Asn Asn Pro Asn Ile Ser Met Ser Asp Phe Thr Met Gln
                805             810             815
Gln Leu Gln Asn Gly Leu Lys Ala Phe Tyr Glu Asp Gln His Gln Ser
                820             825             830
Val Lys Lys Tyr Asn Gln Tyr Asn Ile Pro Ser Ala Tyr Ala Leu Leu
            835             840             845
Leu Thr Asn Lys Asp Thr Val Pro Arg Val Phe Tyr Gly Asp Met Tyr
        850             855             860
Gln Asp Tyr Gly Asp Asp Leu Asp Gly Gly Gln Tyr Met Ala Thr Lys
865             870             875             880
Ser Ile Tyr Tyr Asn Ala Ile Glu Gln Met Met Lys Ala Arg Leu Lys
            885             890             895
Tyr Val Ala Gly Gly Gln Ile Met Ala Val Thr Lys Ile Lys Asn Asp
        900             905             910
Gly Ile Asn Lys Asp Gly Thr Asn Lys Ser Gly Glu Val Leu Thr Ser
    915             920             925
Val Arg Phe Gly Lys Asp Ile Met Asp Ala Gln Gly Gln Gly Thr Ala
930             935             940
Glu Ser Arg Asn Gln Gly Ile Gly Val Ile Val Ser Asn Ser Ser Gly
945             950             955             960
Leu Glu Leu Lys Asn Ser Asp Ser Ile Thr Leu His Met Gly Ile Ala
                965             970             975
His Lys Asn Gln Ala Tyr Arg Ala Leu Met Leu Thr Asn Asp Lys Gly
            980             985             990
Ile Val Asn Tyr Asp Gln Asp Asn Asn Ala Pro Ile Ala Trp Thr Asn
        995             1000            1005
Asp His  Gly Asp Leu Ile Phe  Thr Asn Gln Met Ile  Asn Gly Gln
1010             1015             1020
Ser Asp  Thr Ala Val Lys Gly  Tyr Leu Asn Pro Glu  Val Ala Gly
1025             1030             1035
Tyr Leu  Ala Val Trp Val Pro  Val Gly Ala Asn Asp  Asn Gln Asp
1040             1045             1050
Ala Arg  Thr Val Thr Thr Asn  Gln Lys Asn Thr Asp  Gly Lys Val
1055             1060             1065
Leu His  Thr Asn Ala Ala Leu  Asp Ser Leu Met  Tyr Glu Gly
1070             1075             1080
Phe Ser  Asn Phe Gln Lys Met  Pro Thr Arg Gly Asn  Gln Tyr Ala
1085             1090             1095
Asn Val  Ile Ile Ala Lys Asn  Ile Asp Leu Phe Lys  Ser Trp Gly
1100             1105             1110
```

-continued

```
Ile Thr Asp Phe Glu Leu Ala Pro Gln Tyr Arg Ser Ser Asp Gly
1115                1120                1125

Lys Asp Ile Thr Asp Arg Phe Leu Asp Ser Ile Val Gln Asn Gly
1130                1135                1140

Tyr Gly Leu Ser Asp Arg Tyr Asp Leu Gly Phe Lys Thr Pro Thr
1145                1150                1155

Lys Tyr Gly Thr Asp Gln Asp Leu Arg Lys Ala Ile Glu Arg Leu
1160                1165                1170

His Gln Ala Gly Met Ser Val Met Ala Asp Phe Val Ala Asn Gln
1175                1180                1185

Ile Tyr Gly Leu His Ala Asp Lys Glu Val Val Ser Ala Gln His
1190                1195                1200

Val Asn Ile Asn Gly Asp Thr Lys Leu Val Val Asp Pro Arg Tyr
1205                1210                1215

Gly Thr Gln Met Thr Val Val Asn Ser Val Gly Gly Asp Tyr
1220                1225                1230

Gln Ala Lys Tyr Gly Gly Glu Tyr Leu Asp Thr Ile Ser Lys Leu
1235                1240                1245

Tyr Pro Gly Leu Leu Leu Asp Ser Asn Gly Gln Lys Ile Asp Leu
1250                1255                1260

Ser Thr Lys Ile Lys Glu Trp Ser Ala Lys Tyr Leu Asn Gly Ser
1265                1270                1275

Asn Ile Pro Gln Val Gly Met Gly Tyr Val Leu Lys Asp Trp Asn
1280                1285                1290

Asn Gly Gln Tyr Phe His Ile Leu Asp Lys Glu Gly Gln Tyr Ser
1295                1300                1305

Leu Pro Thr Gln Leu Val Ser Asn Asp Pro Glu Thr Gln Ile Gly
1310                1315                1320

Glu Ser Val Asn Tyr Lys Tyr Phe Ile Gly Asn Ser Asp Ala Thr
1325                1330                1335

Tyr Asn Met Tyr His Asn Leu Pro Asn Thr Val Ser Leu Ile Asn
1340                1345                1350

Ser Gln Glu Gly Gln Ile Lys Thr Gln Ser Gly Val Thr Ser
1355                1360                1365

Asp Tyr Glu Gly Gln Gln Val Gln Val Thr Arg Gln Tyr Thr Asp
1370                1375                1380

Ser Lys Gly Val Ser Trp Asn Leu Ile Thr Phe Ala Gly Gly Asp
1385                1390                1395

Leu Gln Gly Gln Lys Leu Trp Val Asp Ser Arg Ala Leu Thr Met
1400                1405                1410

Thr Pro Phe Lys Thr Met Asn Gln Ile Ser Phe Ile Ser Tyr Ala
1415                1420                1425

Asn Arg Asn Asp Gly Leu Phe Leu Asn Ala Pro Tyr Gln Val Lys
1430                1435                1440

Gly Tyr Gln Leu Ala Gly Met Ser Asn Gln Tyr Lys Gly Gln Gln
1445                1450                1455

Val Thr Ile Ala Gly Val Ala Asn Val Ser Gly Lys Asp Trp Ser
1460                1465                1470

Leu Ile Ser Phe Asn Gly Thr Gln Tyr Trp Ile Asp Ser Gln Ala
1475                1480                1485

Leu Asn Thr Asn Phe Thr His Asp Met Asn Gln Lys Val Phe Val
1490                1495                1500
```

```
Asn Thr Thr Ser Asn Leu Asp Gly Leu Phe Leu Asn Ala Pro Tyr
    1505                1510                1515

Arg Gln Pro Gly Tyr Lys Leu Ala Gly Leu Ala Lys Asn Tyr Asn
    1520                1525                1530

Asn Gln Thr Val Thr Val Ser Gln Gln Tyr Phe Asp Asp Gln Gly
    1535                1540                1545

Thr Val Trp Ser Gln Val Val Leu Gly Gly Gln Thr Val Trp Val
    1550                1555                1560

Asp Asn His Ala Leu Ala Gln Met Gln Val Ser Asp Thr Ser Gln
    1565                1570                1575

Gln Leu Tyr Val Asn Ser Asn Gly Arg Asn Asp Gly Leu Phe Leu
    1580                1585                1590

Asn Ala Pro Tyr Arg Gly Gln Gly Ser Gln Leu Ile Gly Met Thr
    1595                1600                1605

Ala Asp Tyr
    1610

<210> SEQ ID NO 15
<211> LENGTH: 5322
<212> TYPE: DNA
<213> ORGANISM: Artificial Sequence
<220> FEATURE:
<223> OTHER INFORMATION: optimised Leuconostoc fallax AN optimised
      sequence

<400> SEQUENCE: 15
atgaagcagc aagagagcat cactcgtaag aagctgtaca aggcgggcaa aagctgggta      60
gtcgcagcaa ctctgttcgc tgcaactctg tttgctgcaa tgggtgctgc tggtgcaact     120
actgttgcat ctgcagacgt acaaaaggat actgtagtgg taaccgcaga taagaacacc     180
accgataagg acaaggagcc aatcaagacc gcaggtgcta acgtagtcga taagggtgta     240
gcacaaacta ccgataccaa caccaccgac aaaaagacca tcgaggtcgg taaaagcgtc     300
gatatgagcg caactgacaa gaaggtgacc gagactgtca gagcgtaga cactagcgct     360
actgacaaga aaacgacgga ggcagttaag cctgtcgata ctaacgctac cgataagaag     420
gctaccgagg ctgttaagcc tgtagatact aacgcaaccg ataagaaaac caccgaggca     480
gtgaagcctg tcgacactaa cactacggac aagaaggtca ctgaggcaat caaaccggtc     540
aacactaacg cagacgataa aaccgccgag cctgttaaga ctatcagcgc aactaaagac     600
acggtcaaaa ccatcgcgaa caaacagaaa ggtgccacgg aggagcaagc agtcatcact     660
gagggtcatt acgaggcaca aggtgacggt tttgtctaca tcactaaaga cggcaaacag     720
ctgaccggtc tgcaaaacat caacggtaac acccagtact cgatccggc  aactggtcaa     780
caactgaaag cgatatcaa agccgtggct ggtactgtct actacttcga caaaaacagc     840
ggcaacgcac gtgtctacca aaagtcgcc  gatggtactt acagcgagaa caacgaacac     900
tggcaataca tcagcaaagt cgacaacaaa ccagtggaag gtctgtacaa cgtgcagggt     960
aacctgcagt acttcgacat gagcaccggt aaccaggtca aaaacgacat ccgtagcgtg    1020
gacggtgtga cttactactt tgacaaagac agcggtaacg ctccgctttt caacgcactg    1080
agcgcaggtg aatacgttga gaaaaagaa  ccgacgcac  agggtaacca aaacagctac    1140
tggacgtaca gcggtctgga tggtaaccct gttaagggtc tgtacgatat caacggttcc    1200
ctgcaatact cgacgagaa  aaacggcgca cagctgaaag gtggtactgc aactgtgaac    1260
ggtgtgacgt actacttcga acaggataaa ggcaacctga tcagcgtggt caacagcgtg    1320
```

```
gaaagcggtc aatacaaaat cgacaacgac aacgtgtact acatcgacaa ccagggcaac    1380
accctgaaag gtctgtacgc tatcaacggt cagctgaact atttcgacat gtccacgggt    1440
gtgcaactga aggtgcaag cgaaaacgct aacggtgtgg gttactattt cgataaagac    1500
aaaggcaacg gccagtacca gtacagcctg atcacgtcca ccctggcaaa cgctttcagc    1560
aaacacaacg cagcaaacga ttacacgcag agcagcttca ctcataccgt ggatggtttc    1620
ctgactgctg atacttggta ccgtccaact gaaatcctga aaacggcac cacctgggtg    1680 gcatctacta gccaagatct gcgtccaatg atcactgtgt ggtggccaaa caaaaacgtg    1740
caactgaact acctgaaact gatgcagacc gaaggtctgc tggattctgg tcaagtgtac    1800
gacctgaact ctgaccaagc actgctgaac caggctgctc agactgttca ggtaaacatc    1860
gaaaaacgta tcaccaaagc cggtaactcc gactggctga cgatctgct gtacaactct    1920 cacggtgaaa ctccatcttt cgtgaaacag caggctatct ggaacgctga ctctgaatac    1980
cacggtggtt ggttccaggg tggttatctg gcttaccgta actctgacct gactccgtat    2040
gctaactctt cttaccgtca ttacgggt atggaatttc tgctggccaa cgacgtggac    2100
aactctaacc cgatcgtgca ggctgaagat ctgaactggc tgtattacct gatgaacttc    2160
ggcactgaaa cgggtaacga cccgcaagct aatttcgact ctatccgtat cgacgctatc    2220
tctttcgtgg acaaacaggt ggctaaaaaa gcgtacgaac tgctgcacga catgtacggt    2280
ctgtctgctt ctgacgctgt ggctaacaaa acgtgtcta tcgtggaagc ttctgctgac    2340
cagactccgg ttactactga aaaccacgac gctctgatcg aatcttactg gcgtgacact    2400
atgaaaaact ccctgtccaa agacgcgtct atcgactcct ctgctggttc tctgtctgct    2460
atgatcaacg acggtaacgt ggaccgtgct aatgactcta ctactgaatc ctccatcttc    2520
ccgaactaca ccatcgtgca tgctcatgac aaagacatcc aggacgctgt gtctaacgtg    2580
atgaaaatcg tgaacaacga cccgtccatc tccctggacg gtttcactat ggaacagctg    2640
gaaaaaggcc tgtctgcttt ctacgcggat cagcgttctg ctgtaaaaca gtacaaccag    2700
tacaacatcc cgtccgcgta tgcggttatg ctgactaaca aagacaccgt gccgcgtact    2760
ttctacggcg atatgtacca ggatgacggt cagtatatgg cgaacaaatc cctgtactac    2820
gacgcgatcg ataccatgat gaaagcccgt ctgaaatacg tttccggtgg tcagaccatg    2880
tctgttacga aaatcaacaa tgccaactcc cagaaatccg cgaagttct gacctccgtt    2940 cgtttcggta aaggcgttat ggacgcgacc gatgccggtt ctgcggaatc tcgtacccag    3000
ggtattggtg ttgttgtatc taactcttct ggtctgcagc tgaatgacaa cgacaaaatc    3060
gttctgcaca tgggtgccgc gcataaaaac caggaatacc gtgcgctgat gctgaccacg    3120
aatgatggta ttaagtcttt caacaacgac gaagcgccga tcaactacac cgacgacaac    3180
ggcgatctga ttttcgacgg tcataacatc gacggtcagg aaaacaccgc gattcgtggt    3240
tacctgaacc gcaggttgc cggttatctg gcggtttggg ttccgacggg tgccaaagat    3300
gatcaggatg cgcgtaccca gccgtctaat gaaaaatcta ccgatggtaa agttctgcat    3360
accaatgcgg ccctggattc tgaactgatc tatgaaggtt tttctaattt ccagccgatg    3420
ccgaccacca aagatgaata taccaacgtt atgatcgcga aaaacattga cctgttcaaa    3480
tcctggggca ttaccaactt cgaactggcg ccgcagtacc gttcttccga cggtaaaaac    3540
attaacgacc gcttcattga ctccctggtg cagaacggtt acggtctgtc cgatcgttac    3600
gacctgggtt ttgaaccccc gaccaaatac ggcaccgatc aggatctgcg taccgccatt    3660
aagaccctgc accaggcggg catgaccgta atggccgatt atgttgcgaa tcagatctat    3720
```

```
ggcctgaata cctctcagga agttgtagat gcccagcgtg taaattctga taataatgcg    3780
gtagaagtac gttacggcca gcacctgaat gttgtaaact ctattggcgg tggcgaatat    3840
cagaacctgt acggcggcaa atatctggaa attctgaaca aactgtaccc ggacctgctg    3900
gtagacgaaa acggcaacaa gattgacatt gacaccaaaa tcaaacagtg gtccgcgaaa    3960
tacctgaacg gctccaacgt gaccggcctg gcatgggct atgttctgaa agattggtct    4020
aacggccagt atttcaacat ctccaacacc gacggcaaag ttatgctgcc ggaacagctg    4080
gtaaaacaca tgccggcggt tgaaatcggc acccagacca attataccgc gtatatttct    4140
tccaccattc gtcgtgacgg cctgtataac aacatgccgt ggggcgttac ggcgaccggc    4200
caggatggca atgaaattaa gtgggaacgt cagggctcta cctccgatta taatcaccag    4260
aaagttcagg ttaatcgtca gtatgttgac aaacagggcg tagtttggaa cctgattaac    4320
ttcgatgata agatctgtg ggttgactcc aacgcgctgg tgacggtaaa cttcacctcc    4380
cagaaaccga ccaaacactt cgtacagttc ggcatgcgtc agggcaaata cgatggcttt    4440
tacctgagcg cgccgtacaa acagaccgaa tctaaatggg ttgcgtctac ccgtacccac    4500
cagggccagc tgctggaagt tgttggccag tataccaccg gctccggcag ccgcaaagtt    4560
acctggtatc tggttggcct ggatggcaaa caggtttggg ttgatagccg cgccgttggc    4620 acgaattta gccacaaaac caatattaat ctgctgatta ttccgcgac ccgcaatgat    4680 ggcatgtatc tgaatgcccc gtatggccag aaaggctaca acgcgaaac cagctcccgc    4740 ttttataatg aaaaactggt taccgtttcc cagcagtatt atgataacaa aggcgttatt    4800
tggaatctga ttaccctgaa cggcaaaaaa ctgtgggttg attcccgcgc ctttgcgacg    4860
gttattgata aaaagttaa ccagtccctg tacattaaca gccgcaacga tggtatgtat    4920
ctgaacgccc gtatcgcgc gcagggcgcg aaacgctatg cgtccaccaa aacctatacc    4980
ggccagcgcg tacaggtaac cctgcagcgc aaagatacc cacggcgttac gtggtatctg    5040 accaaagttg atagcaaaca gctgtgggta gattcccacg cgtttgcgcc gacgtttacc    5100
cgcaacgtta gcctgaacgt taaagttaac tccagcaaac gcaacgatgg catctatctg    5160
aacgcgccgt atggcaacaa aaaagcgaaa cgcattgcga gcaccaaagc gtataacggc    5220
aaacgcgtta agcctccaa agaatacaaa gatgcgaaag gcgtaacctg gtacctggtt    5280
aacctgaaca caaacaggt atggattgat aaacgtgcgt tt                       5322
```

<210> SEQ ID NO 16
<211> LENGTH: 1774
<212> TYPE: PRT
<213> ORGANISM: Leuconostoc fallax

<400> SEQUENCE: 16

```
Met Lys Gln Gln Glu Ser Ile Thr Arg Lys Lys Leu Tyr Lys Ala Gly
1               5                   10                  15

Lys Ser Trp Val Val Ala Ala Thr Leu Phe Ala Ala Thr Leu Phe Ala
            20                  25                  30

Ala Met Gly Ala Ala Gly Ala Thr Thr Val Ala Ser Ala Asp Val Gln
        35                  40                  45

Lys Asp Thr Val Val Val Thr Ala Asp Lys Asn Thr Asp Lys Asp
    50                  55                  60

Lys Glu Pro Ile Lys Thr Ala Gly Ala Asn Val Val Asp Lys Gly Val
65                  70                  75                  80

Ala Gln Thr Thr Asp Thr Asn Thr Thr Asp Lys Lys Thr Ile Glu Val
```

-continued

```
                85                  90                  95
Gly Lys Ser Val Asp Met Ser Ala Thr Asp Lys Lys Val Thr Glu Thr
                100                 105                 110

Val Lys Ser Val Asp Thr Ser Ala Thr Asp Lys Lys Thr Thr Glu Ala
                115                 120                 125

Val Lys Pro Val Asp Thr Asn Ala Thr Asp Lys Lys Ala Thr Glu Ala
                130                 135                 140

Val Lys Pro Val Asp Thr Asn Ala Thr Asp Lys Lys Thr Thr Glu Ala
145                 150                 155                 160

Val Lys Pro Val Asp Thr Asn Thr Thr Asp Lys Lys Val Thr Glu Ala
                165                 170                 175

Ile Lys Pro Val Asn Thr Asn Ala Asp Asp Lys Thr Ala Glu Pro Val
                180                 185                 190

Lys Thr Ile Ser Ala Thr Lys Asp Thr Val Lys Thr Ile Ala Asn Lys
                195                 200                 205

Gln Lys Gly Ala Thr Glu Glu Gln Ala Val Ile Thr Glu Gly His Tyr
                210                 215                 220

Glu Ala Gln Gly Asp Gly Phe Val Tyr Ile Thr Lys Asp Gly Lys Gln
225                 230                 235                 240

Leu Thr Gly Leu Gln Asn Ile Asn Gly Asn Thr Gln Tyr Phe Asp Pro
                245                 250                 255

Ala Thr Gly Gln Gln Leu Lys Gly Asp Ile Lys Ala Val Ala Gly Thr
                260                 265                 270

Val Tyr Tyr Phe Asp Lys Asn Ser Gly Asn Ala Arg Val Tyr Gln Lys
                275                 280                 285

Val Ala Asp Gly Thr Tyr Ser Glu Asn Asn Glu His Trp Gln Tyr Ile
                290                 295                 300

Ser Lys Val Asp Asn Lys Pro Val Glu Gly Leu Tyr Asn Val Gln Gly
305                 310                 315                 320

Asn Leu Gln Tyr Phe Asp Met Ser Thr Gly Asn Gln Val Lys Asn Asp
                325                 330                 335

Ile Arg Ser Val Asp Gly Val Thr Tyr Tyr Phe Asp Lys Asp Ser Gly
                340                 345                 350

Asn Gly Ser Ala Phe Asn Ala Leu Ser Ala Gly Glu Tyr Val Glu Lys
                355                 360                 365

Lys Glu Thr Asp Ala Gln Gly Asn Gln Asn Ser Tyr Trp Thr Tyr Ser
                370                 375                 380

Gly Leu Asp Gly Asn Pro Val Lys Gly Leu Tyr Asp Ile Asn Gly Ser
385                 390                 395                 400

Leu Gln Tyr Phe Asp Glu Lys Asn Gly Ala Gln Leu Lys Gly Gly Thr
                405                 410                 415

Ala Thr Val Asn Gly Val Thr Tyr Tyr Phe Glu Gln Asp Lys Gly Asn
                420                 425                 430

Leu Ile Ser Val Asn Ser Val Glu Ser Gly Gln Tyr Lys Ile Asp
                435                 440                 445

Asn Asp Asn Val Tyr Tyr Ile Asp Asn Gln Gly Asn Thr Leu Lys Gly
                450                 455                 460

Leu Tyr Ala Ile Asn Gly Gln Leu Asn Tyr Phe Asp Met Ser Thr Gly
465                 470                 475                 480

Val Gln Leu Lys Gly Ala Ser Glu Asn Ala Asn Gly Val Gly Tyr Tyr
                485                 490                 495

Phe Asp Lys Asp Lys Gly Asn Gly Gln Tyr Gln Tyr Ser Leu Ile Thr
                500                 505                 510
```

```
Ser Thr Leu Ala Asn Ala Phe Ser Lys His Asn Ala Ala Asn Asp Tyr
    515                 520                 525

Thr Gln Ser Ser Phe Thr His Thr Val Asp Gly Phe Leu Thr Ala Asp
    530                 535                 540

Thr Trp Tyr Arg Pro Thr Glu Ile Leu Lys Asn Gly Thr Thr Trp Val
545                 550                 555                 560

Ala Ser Thr Ser Gln Asp Leu Arg Pro Met Ile Thr Val Trp Trp Pro
                565                 570                 575

Asn Lys Asn Val Gln Leu Asn Tyr Leu Lys Leu Met Gln Thr Glu Gly
                580                 585                 590

Leu Leu Asp Ser Gly Gln Val Tyr Asp Leu Asn Ser Asp Gln Ala Leu
            595                 600                 605

Leu Asn Gln Ala Ala Gln Thr Val Gln Val Asn Ile Glu Lys Arg Ile
            610                 615                 620

Thr Lys Ala Gly Asn Ser Asp Trp Leu Asn Asp Leu Leu Tyr Asn Ser
625                 630                 635                 640

His Gly Glu Thr Pro Ser Phe Val Lys Gln Gln Ala Ile Trp Asn Ala
                645                 650                 655

Asp Ser Glu Tyr His Gly Gly Trp Phe Gln Gly Tyr Leu Ala Tyr
                660                 665                 670

Arg Asn Ser Asp Leu Thr Pro Tyr Ala Asn Ser Ser Tyr Arg His Tyr
                675                 680                 685

Thr Gly Met Glu Phe Leu Leu Ala Asn Asp Val Asp Asn Ser Asn Pro
690                 695                 700

Ile Val Gln Ala Glu Asp Leu Asn Trp Leu Tyr Tyr Leu Met Asn Phe
705                 710                 715                 720

Gly Thr Glu Thr Gly Asn Asp Pro Gln Ala Asn Phe Asp Ser Ile Arg
                725                 730                 735

Ile Asp Ala Ile Ser Phe Val Asp Lys Gln Val Ala Lys Lys Ala Tyr
                740                 745                 750

Glu Leu Leu His Asp Met Tyr Gly Leu Ser Ala Ser Asp Ala Val Ala
        755                 760                 765

Asn Lys His Val Ser Ile Val Glu Ala Ser Ala Asp Gln Thr Pro Val
        770                 775                 780

Thr Thr Glu Asn His Asp Ala Leu Ile Glu Ser Tyr Trp Arg Asp Thr
785                 790                 795                 800

Met Lys Asn Ser Leu Ser Lys Asp Ala Ser Ile Asp Ser Ser Ala Gly
                805                 810                 815

Ser Leu Ser Ala Met Ile Asn Asp Gly Asn Val Asp Arg Ala Asn Asp
                820                 825                 830

Ser Thr Thr Glu Ser Ser Ile Phe Pro Asn Tyr Thr Ile Val His Ala
            835                 840                 845

His Asp Lys Asp Ile Gln Asp Ala Val Ser Asn Val Met Lys Ile Val
        850                 855                 860

Asn Asn Asp Pro Ser Ile Ser Leu Asp Gly Phe Thr Met Glu Gln Leu
865                 870                 875                 880

Glu Lys Gly Leu Ser Ala Phe Tyr Ala Asp Gln Arg Ser Ala Val Lys
                885                 890                 895

Gln Tyr Asn Gln Tyr Asn Ile Pro Ser Ala Tyr Ala Val Met Leu Thr
            900                 905                 910

Asn Lys Asp Thr Val Pro Arg Thr Phe Tyr Gly Asp Met Tyr Gln Asp
            915                 920                 925
```

-continued

```
Asp Gly Gln Tyr Met Ala Asn Lys Ser Leu Tyr Tyr Asp Ala Ile Asp
    930                 935                 940

Thr Met Met Lys Ala Arg Leu Lys Tyr Val Ser Gly Gln Thr Met
945                 950                 955                 960

Ser Val Thr Lys Ile Asn Asn Ala Asn Ser Gln Lys Ser Gly Glu Val
                965                 970                 975

Leu Thr Ser Val Arg Phe Gly Lys Gly Val Met Asp Ala Thr Asp Ala
                980                 985                 990

Gly Ser Ala Glu Ser Arg Thr Gln Gly Ile Gly Val Val Ser Asn
            995                 1000                 1005

Ser Ser Gly Leu Gln Leu Asn Asp Asn Asp Lys Ile Val Leu His
    1010                1015                1020

Met Gly Ala Ala His Lys Asn Gln Glu Tyr Arg Ala Leu Met Leu
    1025                1030                1035

Thr Thr Asn Asp Gly Ile Lys Ser Phe Asn Asn Asp Glu Ala Pro
    1040                1045                1050

Ile Asn Tyr Thr Asp Asp Asn Gly Asp Leu Ile Phe Asp Gly His
    1055                1060                1065

Asn Ile Asp Gly Gln Glu Asn Thr Ala Ile Arg Gly Tyr Leu Asn
    1070                1075                1080

Pro Gln Val Ala Gly Tyr Leu Ala Val Trp Val Pro Thr Gly Ala
    1085                1090                1095

Lys Asp Asp Gln Asp Ala Arg Thr Gln Pro Ser Asn Glu Lys Ser
    1100                1105                1110

Thr Asp Gly Lys Val Leu His Thr Asn Ala Ala Leu Asp Ser Glu
    1115                1120                1125

Leu Ile Tyr Glu Gly Phe Ser Asn Phe Gln Pro Met Pro Thr Thr
    1130                1135                1140

Lys Asp Glu Tyr Thr Asn Val Met Ile Ala Lys Asn Ile Asp Leu
    1145                1150                1155

Phe Lys Ser Trp Gly Ile Thr Asn Phe Glu Leu Ala Pro Gln Tyr
    1160                1165                1170

Arg Ser Ser Asp Gly Lys Asn Ile Asn Asp Arg Phe Ile Asp Ser
    1175                1180                1185

Leu Val Gln Asn Gly Tyr Gly Leu Ser Asp Arg Tyr Asp Leu Gly
    1190                1195                1200

Phe Glu Thr Pro Thr Lys Tyr Gly Thr Asp Gln Asp Leu Arg Thr
    1205                1210                1215

Ala Ile Lys Thr Leu His Gln Ala Gly Met Thr Val Met Ala Asp
    1220                1225                1230

Tyr Val Ala Asn Gln Ile Tyr Gly Leu Asn Thr Ser Gln Glu Val
    1235                1240                1245

Val Asp Ala Gln Arg Val Asn Ser Asp Asn Asn Ala Val Glu Val
    1250                1255                1260

Arg Tyr Gly Gln His Leu Asn Val Val Asn Ser Ile Gly Gly Gly
    1265                1270                1275

Glu Tyr Gln Asn Leu Tyr Gly Gly Lys Tyr Leu Glu Ile Leu Asn
    1280                1285                1290

Lys Leu Tyr Pro Asp Leu Leu Val Asp Glu Asn Gly Asn Lys Ile
    1295                1300                1305

Asp Ile Asp Thr Lys Ile Lys Gln Trp Ser Ala Lys Tyr Leu Asn
    1310                1315                1320

Gly Ser Asn Val Thr Gly Leu Gly Met Gly Tyr Val Leu Lys Asp
```

-continued

```
              1325                1330                1335
Trp Ser Asn Gly Gln Tyr Phe Asn Ile Ser Asn Thr Asp Gly Lys
          1340                1345                1350
Val Met Leu Pro Glu Gln Leu Val Lys His Met Pro Ala Val Glu
          1355                1360                1365
Ile Gly Thr Gln Thr Asn Tyr Thr Ala Tyr Ile Ser Ser Thr Ile
          1370                1375                1380
Arg Arg Asp Gly Leu Tyr Asn Asn Met Pro Trp Gly Val Thr Ala
          1385                1390                1395
Thr Gly Gln Asp Gly Asn Glu Ile Lys Trp Glu Arg Gln Gly Ser
          1400                1405                1410
Thr Ser Asp Tyr Asn His Gln Lys Val Gln Val Asn Arg Gln Tyr
          1415                1420                1425
Val Asp Lys Gln Gly Val Val Trp Asn Leu Ile Asn Phe Asp Asp
          1430                1435                1440
Lys Asp Leu Trp Val Asp Ser Asn Ala Leu Val Thr Val Asn Phe
          1445                1450                1455
Thr Ser Gln Lys Pro Thr Lys His Phe Val Gln Phe Gly Met Arg
          1460                1465                1470
Gln Gly Lys Tyr Asp Gly Phe Tyr Leu Ser Ala Pro Tyr Lys Gln
          1475                1480                1485
Thr Glu Ser Lys Trp Val Ala Ser Thr Arg Thr His Gln Gly Gln
          1490                1495                1500
Leu Leu Glu Val Val Gly Gln Tyr Thr Thr Gly Ser Gly Ser Arg
          1505                1510                1515
Lys Val Thr Trp Tyr Leu Val Gly Leu Asp Gly Lys Gln Val Trp
          1520                1525                1530
Val Asp Ser Arg Ala Val Gly Thr Asn Phe Ser His Lys Thr Asn
          1535                1540                1545
Ile Asn Leu Leu Ile Asn Ser Ala Thr Arg Asn Asp Gly Met Tyr
          1550                1555                1560
Leu Asn Ala Pro Tyr Gly Gln Lys Gly Tyr Lys Arg Glu Thr Ser
          1565                1570                1575
Ser Arg Phe Tyr Asn Glu Lys Leu Val Thr Val Ser Gln Gln Tyr
          1580                1585                1590
Tyr Asp Asn Lys Gly Val Ile Trp Asn Leu Ile Thr Leu Asn Gly
          1595                1600                1605
Lys Lys Leu Trp Val Asp Ser Arg Ala Phe Ala Thr Val Ile Asp
          1610                1615                1620
Lys Lys Val Asn Gln Ser Leu Tyr Ile Asn Ser Arg Asn Asp Gly
          1625                1630                1635
Met Tyr Leu Asn Ala Pro Tyr Arg Ala Gln Gly Ala Lys Arg Tyr
          1640                1645                1650
Ala Ser Thr Lys Thr Tyr Thr Gly Gln Arg Val Gln Val Thr Leu
          1655                1660                1665
Gln Arg Lys Asp Thr His Gly Val Thr Trp Tyr Leu Thr Lys Val
          1670                1675                1680
Asp Ser Lys Gln Leu Trp Val Asp Ser His Ala Phe Ala Pro Thr
          1685                1690                1695
Phe Thr Arg Asn Val Ser Leu Asn Val Lys Val Asn Ser Ser Lys
          1700                1705                1710
Arg Asn Asp Gly Ile Tyr Leu Asn Ala Pro Tyr Gly Asn Lys Lys
          1715                1720                1725
```

```
Ala Lys Arg Ile Ala Ser Thr Lys Ala Tyr Asn Gly Lys Arg Val
    1730                1735                1740

Lys Ala Ser Lys Glu Tyr Lys Asp Ala Lys Gly Val Thr Trp Tyr
    1745                1750                1755

Leu Val Asn Leu Asn Asn Lys Gln Val Trp Ile Asp Lys Arg Ala
    1760                1765                1770

Phe

<210> SEQ ID NO 17
<211> LENGTH: 7
<212> TYPE: PRT
<213> ORGANISM: Artificial Sequence
<220> FEATURE:
<223> OTHER INFORMATION: enzymatic domain

<400> SEQUENCE: 17

Ala Asp Phe Val Ala Asn Gln
1               5

<210> SEQ ID NO 18
<211> LENGTH: 11
<212> TYPE: PRT
<213> ORGANISM: Artificial Sequence
<220> FEATURE:
<223> OTHER INFORMATION: Enzymatic domain

<400> SEQUENCE: 18

Ser Met Arg Ile Asp Ala Ile Ser Phe Val Asp
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Enzymatic domain

<400> SEQUENCE: 19

His Ile Ser Ile Val Glu Ala Pro Lys Gly Glu
1               5                   10

<210> SEQ ID NO 20
<211> LENGTH: 15
<212> TYPE: PRT
<213> ORGANISM: Artificial Sequence
<220> FEATURE:
<223> OTHER INFORMATION: Enzymatic domain

<400> SEQUENCE: 20

Ile Val His Ala His Asp Lys Asp Ile Gln Asp Thr Val Ile His
1               5                   10                  15

<210> SEQ ID NO 21
<211> LENGTH: 7
<212> TYPE: PRT
<213> ORGANISM: Artificial Sequence
<220> FEATURE:
<223> OTHER INFORMATION: Enzymatic domain

<400> SEQUENCE: 21

Ala Asp Tyr Val Ala Asn Gln
1               5

<210> SEQ ID NO 22
```

```
<211> LENGTH: 11
<212> TYPE: PRT
<213> ORGANISM: Artificial Sequence
<220> FEATURE:
<223> OTHER INFORMATION: Enzymatic domain

<400> SEQUENCE: 22

Ser Ile Arg Ile Asp Ala Ile Ser Phe Val Asp
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Enzymatic domain

<400> SEQUENCE: 23

His Val Ser Ile Val Glu Ala Ser Ala Asp Gln
1               5                   10

<210> SEQ ID NO 24
<211> LENGTH: 15
<212> TYPE: PRT
<213> ORGANISM: Artificial Sequence
<220> FEATURE:
<223> OTHER INFORMATION: Enzymatic domain

<400> SEQUENCE: 24

Ile Val His Ala His Asp Lys Asp Ile Gln Asp Ala Val Ser Asn
1               5                   10                  15
```